United States Patent
Wu et al.

(10) Patent No.: US 8,530,712 B2
(45) Date of Patent: Sep. 10, 2013

(54) PROCESS FOR PRODUCING NOVEL SYNTHETIC BASESTOCKS

(75) Inventors: Margaret M. Wu, Skillman, NJ (US); Steven P. Rucker, Warren, NJ (US); Jo Ann M. Canich, Houston, TX (US)

(73) Assignee: Exxonmobil Chemical Patents Inc., Houston, TX (US)

( * ) Notice: Subject to any disclaimer, the term of this patent is extended or adjusted under 35 U.S.C. 154(b) by 15 days.

(21) Appl. No.: 12/971,546

(22) Filed: Dec. 17, 2010

(65) Prior Publication Data

US 2011/0160502 A1    Jun. 30, 2011

Related U.S. Application Data

(60) Provisional application No. 61/284,833, filed on Dec. 24, 2009.

(51) Int. Cl.
*C07C 9/22* (2006.01)
*C07C 11/00* (2006.01)
*C10M 107/02* (2006.01)

(52) U.S. Cl.
USPC ............ 585/18; 585/10; 585/12; 585/16; 585/17; 508/591

(58) Field of Classification Search
USPC ............ 585/10, 12, 13, 16–18; 508/591
See application file for complete search history.

(56) References Cited

U.S. PATENT DOCUMENTS

| | | | |
|---|---|---|---|
| 2,978,442 | A | 4/1961 | Brightbill et al. |
| 3,149,178 | A | 9/1964 | Hamilton et al. |

(Continued)

FOREIGN PATENT DOCUMENTS

| | | |
|---|---|---|
| EP | 0 277 004 | 8/1988 |
| EP | 0 277 007 | 8/1988 |

(Continued)

OTHER PUBLICATIONS

J. Brennan, "*Wide-Temperature Range Synthetic Hydrocarbon Fluids*", Ind. Eng. Chem. Prod. Res. Dev., 1980, vol. 19, pp. 2-6.

(Continued)

*Primary Examiner* — Ellen McAvoy
(74) *Attorney, Agent, or Firm* — Nancy T. Krawczyk; Leandro Arechederra, III; Kristina M. Leavitt

(57) ABSTRACT

This disclosure relates to a liquid syndiotactic polyalphaolefin, sPAO, comprising one or more $C_4$ to $C_{24}$ monomers, said sPAO having: a) an rr triad content of 5 to 50% as measured by $^{13}C$ NMR; b) an mr triad content of 25 to 60% as measured by $^{13}C$ NMR, where the mr to mm triad ratio is at least 1.0; c) a pour point of Z ° C. or less, where $Z=0.0648X-51.2$, where X=kinematic viscosity at 100° C. as reported in centistokes (cSt); d) a kinematic viscosity at 100° C. of 100 cSt or more (alternatively 200 cSt or more); e) a ratio of mr triads to rr triad (as determined by $^{13}C$ NMR) of less than 9; f) a ratio of vinylidene to 1,2-disubstituted olefins (as determined by $^1H$ NMR) of less than 8; g) a viscosity index of 120 or more; and h) an Mn of 40,000 or less. This disclosure further relates to processes to make and use sPAOs, including those having any combination of characteristics a) to h).

8 Claims, 3 Drawing Sheets

(56) References Cited

U.S. PATENT DOCUMENTS

| | | |
|---|---|---|
| 3,164,578 A | 1/1965 | Baker et al. |
| 3,382,291 A | 5/1968 | Brennan |
| 3,742,082 A | 6/1973 | Brennan |
| 3,769,363 A | 10/1973 | Brennan |
| 3,780,128 A | 12/1973 | Shubkin |
| 3,876,720 A | 4/1975 | Heilman et al. |
| 3,883,417 A | 5/1975 | Woo et al. |
| 4,016,349 A | 4/1977 | McKenna |
| 4,132,663 A | 1/1979 | Heilman et al. |
| 4,149,178 A | 4/1979 | Estes |
| 4,172,855 A | 10/1979 | Shubkin et al. |
| 4,180,575 A | 12/1979 | Rochling et al. |
| 4,239,930 A | 12/1980 | Allphin et al. |
| 4,263,465 A | 4/1981 | Sheng et al. |
| 4,263,712 A | 4/1981 | Schroder |
| 4,367,352 A | 1/1983 | Watts, Jr. et al. |
| 4,413,156 A | 11/1983 | Watts, Jr. et al. |
| 4,434,408 A | 2/1984 | Baba et al. |
| 4,451,684 A | 5/1984 | Pasky |
| 4,469,912 A | 9/1984 | Blewett et al. |
| 4,587,368 A | 5/1986 | Pratt |
| 4,701,489 A | 10/1987 | Hughes et al. |
| 4,704,491 A | 11/1987 | Tsutsui et al. |
| 4,827,064 A | 5/1989 | Wu |
| 4,827,073 A | 5/1989 | Wu |
| 4,892,851 A | 1/1990 | Ewen et al. |
| 4,910,355 A | 3/1990 | Shubkin et al. |
| 4,912,272 A | 3/1990 | Wu |
| 4,914,254 A | 4/1990 | Pelrine |
| 4,926,004 A | 5/1990 | Pelrine et al. |
| 4,950,822 A | 8/1990 | Dileo et al. |
| 4,956,122 A | 9/1990 | Watts et al. |
| 4,962,262 A | 10/1990 | Winter et al. |
| 4,967,032 A | 10/1990 | Ho et al. |
| 4,990,709 A | 2/1991 | Wu |
| 4,990,771 A | 2/1991 | Minoura et al. |
| 5,012,020 A | 4/1991 | Jackson et al. |
| 5,017,299 A | 5/1991 | Gutierrez et al. |
| 5,017,714 A | 5/1991 | Welborn, Jr. |
| 5,068,487 A | 11/1991 | Theriot |
| 5,087,788 A | 2/1992 | Wu |
| 5,177,276 A | 1/1993 | Beach et al. |
| 5,186,851 A | 2/1993 | Gutierrez et al. |
| 5,188,724 A | 2/1993 | Heilman et al. |
| 5,220,100 A | 6/1993 | Massie et al. |
| 5,264,642 A | 11/1993 | Wu |
| 5,334,677 A * | 8/1994 | Razavi et al. ............. 526/114 |
| 5,369,196 A | 11/1994 | Matsumoto et al. |
| 5,382,739 A | 1/1995 | Atkins et al. |
| 5,462,995 A | 10/1995 | Hosaka et al. |
| 5,498,815 A | 3/1996 | Schaerfl, Jr. et al. |
| 5,552,504 A | 9/1996 | Bennett et al. |
| 5,637,400 A | 6/1997 | Brekner et al. |
| 5,679,812 A | 10/1997 | Winter et al. |
| 5,688,887 A | 11/1997 | Bagheri et al. |
| 5,690,832 A | 11/1997 | Tavlarides et al. |
| 5,705,577 A | 1/1998 | Rossi et al. |
| 5,731,254 A | 3/1998 | Winter et al. |
| 5,811,379 A | 9/1998 | Rossi et al. |
| 5,846,896 A | 12/1998 | Ewen |
| 5,852,143 A | 12/1998 | Sishta et al. |
| 5,859,159 A | 1/1999 | Rossi et al. |
| 6,043,401 A | 3/2000 | Bagheri et al. |
| 6,087,307 A | 7/2000 | Kaminski et al. |
| 6,133,209 A | 10/2000 | Rath et al. |
| 6,147,271 A | 11/2000 | Strebel et al. |
| 6,180,575 B1 | 1/2001 | Nipe |
| 6,388,032 B1 | 5/2002 | Yamaura et al. |
| 6,414,090 B2 | 7/2002 | Minami et al. |
| 6,414,091 B2 | 7/2002 | Moritomi et al. |
| 6,479,722 B1 | 11/2002 | De Wet et al. |
| 6,548,723 B2 | 4/2003 | Bagheri et al. |
| 6,548,724 B2 | 4/2003 | Bagheri et al. |
| 6,642,169 B2 | 11/2003 | Weatherhead |
| 6,646,174 B2 | 11/2003 | Clarembeau |
| 6,706,828 B2 | 3/2004 | DiMaio |
| 6,713,438 B1 | 3/2004 | Baillargeon et al. |
| 6,824,671 B2 | 11/2004 | Goze et al. |
| 6,858,767 B1 | 2/2005 | DiMaio et al. |
| 6,960,700 B1 | 11/2005 | Sethna et al. |
| 7,060,768 B2 | 6/2006 | Brookhart et al. |
| 7,129,197 B2 | 10/2006 | Song et al. |
| 7,473,815 B2 | 1/2009 | Lambert et al. |
| 7,544,850 B2 | 6/2009 | Goze et al. |
| 7,547,811 B2 | 6/2009 | Kramer et al. |
| 7,589,145 B2 * | 9/2009 | Brant et al. ............. 524/515 |
| 7,592,497 B2 | 9/2009 | Yang et al. |
| 7,601,256 B2 | 10/2009 | Beall |
| 7,880,047 B2 * | 2/2011 | Knowles et al. ............. 585/523 |
| 8,071,687 B2 * | 12/2011 | Jiang et al. ............. 525/240 |
| 8,227,392 B2 * | 7/2012 | Wu et al. ............. 508/591 |
| 8,389,780 B2 * | 3/2013 | Knowles et al. ............. 585/18 |
| 2001/0041817 A1 | 11/2001 | Bagheri et al. |
| 2001/0041818 A1 | 11/2001 | Bagheri et al. |
| 2003/0055184 A1 | 3/2003 | Song et al. |
| 2004/0022508 A1 | 2/2004 | Belardi et al. |
| 2004/0033908 A1 | 2/2004 | Deckman et al. |
| 2004/0087746 A1 | 5/2004 | Razavi |
| 2004/0097772 A1 | 5/2004 | Deckers et al. |
| 2004/0147693 A1 | 7/2004 | DiMaio |
| 2004/0220359 A1 | 11/2004 | Abhari et al. |
| 2004/0230016 A1 | 11/2004 | Blackbrow et al. |
| 2005/0059563 A1 | 3/2005 | Sullivan et al. |
| 2005/0101761 A1 | 5/2005 | Lambert et al. |
| 2005/0183988 A1 | 8/2005 | Freerks et al. |
| 2007/0000807 A1 | 1/2007 | Wu et al. |
| 2007/0011832 A1 | 1/2007 | Keidel et al. |
| 2007/0043248 A1 | 2/2007 | Wu et al. |
| 2007/0208151 A1 | 9/2007 | Okada et al. |
| 2009/0005279 A1 * | 1/2009 | Wu et al. ............. 508/591 |
| 2009/0036725 A1 * | 2/2009 | Wu et al. ............. 585/521 |
| 2009/0156874 A1 | 6/2009 | Patil et al. |
| 2009/0281360 A1 * | 11/2009 | Knowles et al. ............. 585/12 |
| 2010/0069687 A1 | 3/2010 | Kosover et al. |
| 2010/0317904 A1 * | 12/2010 | Small et al. ............. 585/18 |
| 2010/0323937 A1 * | 12/2010 | Wu et al. ............. 508/591 |
| 2011/0092752 A1 * | 4/2011 | Knowles et al. ............. 585/18 |

FOREIGN PATENT DOCUMENTS

| | | |
|---|---|---|
| EP | 0 284 708 | 10/1988 |
| EP | 0 321 852 | 6/1989 |
| EP | 0 349 276 | 1/1990 |
| EP | 0 377 306 | 7/1990 |
| EP | 0 403 866 | 12/1990 |
| EP | 0 513 380 | 11/1992 |
| EP | 0 613 873 | 9/1994 |
| EP | 0 680 942 | 11/1995 |
| EP | 0 930 320 | 7/1999 |
| EP | 0 992 517 | 4/2000 |
| EP | 1 028 128 | 8/2000 |
| EP | 1 309 633 | 5/2003 |
| EP | 1 342 707 | 9/2003 |
| EP | 1 607 415 | 12/2005 |
| EP | 1661921 | 5/2006 |
| GB | 938069 | 9/1963 |
| IN | 191553 | 12/2003 |
| JP | 6336590 | 12/1994 |
| JP | 2005-200446 | 7/2005 |
| WO | 96/23751 | 8/1996 |
| WO | 99/67347 | 12/1999 |
| WO | 00/58423 | 10/2000 |
| WO | 02/14384 | 2/2002 |
| WO | 03/009136 | 1/2003 |
| WO | 03/051943 | 6/2003 |
| WO | 03/071369 | 8/2003 |
| WO | 03/104292 | 12/2003 |
| WO | 2004/046214 | 6/2004 |
| WO | 2007/011459 | 1/2007 |
| WO | 2007/011462 | 1/2007 |
| WO | 2007/011832 | 1/2007 |
| WO | 2007/011973 | 1/2007 |
| WO | 2007/145924 | 12/2007 |
| WO | 2007/146081 | 12/2007 |
| WO | 2008/010862 | 1/2008 |

| WO | 2008/010865 | 1/2008 |
| WO | WO2008/042037 | 4/2008 |
| WO | 2009/017953 | 2/2009 |
| WO | 2009/137264 | 11/2009 |

OTHER PUBLICATIONS

K. Denbigh, "*The Kinetics of Continuous Reaction Processes: Application to Polymerization*", J. Applied Chem, 1951, vol. 1, pp. 227-236.

K. Denbigh, "*Continuous Reactions: Part II. The Kinetics of Steady State Polymerisation*", Trans Faraday Soc., 1947, vol. 43, pp. 648-660.

A. Munoz-Escalona et al., "*Single-Site Supported Catalysts for Ethylene Polymerization*", Metallocene Tech., 1999, pp. 2242-2246.

Z. Fan et al., "*Effect of Ethoxy- and Methoxysilane Donors in Propene/1-Hexene Copolymerization With High-Yield Supported Ziegler-Natta Catalysts*", Macromolecular Chemistry and Physics, 1994, vol. 195, pp. 3889-3899.

G. Gokel ed, Dean's Handbook of Organic Chemistry, 2nd Edition, McGraw-Hill, 2004, available on-line at hhtp://knovel.com.

M. LeVan et al. "*Adsorption and Ion Exchange*" Perry's Chemical Engineer's Handbook, 7th ed. 1997 pp. 16-1-16-66.

O. Levenspiel, "*Ch. 7 Design for Multiple Reactions*", Chemical Reaction Engineering, 2nd ed., 1972, pp. 196-209.

N. Naga et al., "*Effect of Co-Catalyst System on a-Olefin Polymerization With Rac- and Meso-[Dimethylsilylenebis(2,3,5-Trimethyl-Cyclopentadienyl)]Zirconium Dichloride*", Macromol. Rapid Commun., 1997, vol. 18, pp. 581-589.

N. Naga et al, "*Polymerization Behavior of a-Olefins With Rac- and Meso-Type Ansa-Metallocene Catalysts: Effects of Cocatalyst and Metallocene Ligand*", Macromolecular Chemistry Physics, 1999, vol. 200, pp. 1587-1594.

F. Rodriguez, "*The Molecular Weight of Polymers*", Principles of Polymer Systems, 1970, Chapter 6, pp. 115-144.

M. Sacchi et al., "*Use of Different Alkoxysilanes as External Donors in $MgCl_2$-Supported Ziegler-Natta Catalysts to Obtain Propene/1-Butene Copolymers With Different Microstructure*", Macromolecular Chemistry and Physics, 1994, vol. 195, pp. 2805-2816.

T. Seraidaris et al., "*High-Molar-Mass Polypropene with Tunable Elastic Properties by Hafnocene/Borate Catalysts*", Journal of Polymer Science: Part A: Polymer Chemistry, 2006, vol. 44, pp. 4743-4751.

J. Wills, "*Synthetic Lubricants*", Lubrication Fundamentals, Marcel Dekker Inc., New York, 1980, pp. 75-80.

"*Mobil Releases SuperSyn PAOs*", Lubrication Engineers, 1999, vol. 55, Part 8, pp. 45.

TIBA data, "*TIBA datasheet*" available on-line at www.albermarle.com on Aug. 26, 2010.

\* cited by examiner

PROCESS FOR PRODUCING NOVEL SYNTHETIC BASESTOCKS

CROSS REFERENCE TO RELATED APPLICATIONS

This application claims priority to U.S. Provisional Application Ser. No. 61/284,833 filed Dec. 24, 2009, the disclosure of which is fully incorporated herein by reference.

FIELD

This disclosure relates to novel synthetic polyalphaolefin liquids useful as lubricant basestocks, preferably in their as-polymerized state.

BACKGROUND

The viscosity-temperature relationship of a lubricating oil is one of the critical criteria which must be considered when selecting a lubricant for a particular application. Viscosity index (VI) is an empirical, unitless number which indicates the rate of change in the viscosity of an oil within a given temperature range and is related to kinematic viscosities measured at 40° C. and 100° C. (typically using ASTM Method D445). Fluids exhibiting a relatively large change in viscosity with temperature are said to have a low viscosity index. A low VI oil, for example, will thin out at elevated temperatures faster than a high VI oil. Usually, the high VI oil is more desirable because it has higher viscosity at higher temperature, which translates into better or thicker lubrication film and better protection of the contacting machine elements. In another aspect, as the oil operating temperature decreases, the viscosity of a high VI oil will not increase as much as the viscosity of a low VI oil. This is advantageous because the excessive high viscosity of the low VI oil will decrease the efficiency of the operating machine. Thus high VI (HVI) oil has performance advantages in both high and low temperature operation. VI is determined according to ASTM method D2270.

Polyalphaolefins (PAOs) comprise a class of hydrocarbons manufactured by the catalytic oligomerization (polymerization to low molecular weight products) of linear alpha-olefins (LAOS) typically ranging from 1-hexene to 1-octadecene, more typically from 1-octene to 1-dodecene, with 1-decene as the most common and often preferred material. Such fluids are described, for example, in U.S. Pat. No. 6,824,671 and patents referenced therein.

Polyalphaolefins produced by conventional Friedel-Crafts catalysts, however are usually characterized by having extra relatively short branches, such as methyl and ethyl short side chains, even though the feed olefins do not contain these short branches. This is thought to be because Friedel-Crafts catalysts partially isomerize the starting alpha-olefins and the intermediates formed during the oligomerization process. The presence of short chain branches typically is less desirable for superior lubricant properties, including VI and volatility.

High viscosity index polyalpha-olefin (HVI-PAO) prepared by, for instance, polymerization of alpha-olefins using reduced metal oxide catalysts (e.g., chromium) are described, for instance, in U.S. Pat. Nos. 4,827,064; 4,827,073; 4,990,771; 5,012,020; and 5,264,642. These HVI-PAOs are characterized by having a high viscosity index of 130 and above, a branch ratio of less than 0.19, a weight average molecular weight (Mw) of between 300 and 45,000, a number average molecular weight (Mn) of between 300 and 18,000, a molecular weight distribution (MWD=Mw/Mn) of between 1 and 5, and pour point below −15° C. Measured in carbon number, these molecules typically range from $C_{30}$ to $C_{1300}$.

In the production of PAOs and HVI-PAOs, the feed may be limited to one specific alpha-olefin, usually 1-decene. Occasionally, when 1-decene is not available in large enough quantity, small to moderate amounts of 1-octene or 1-dodecene are added to make up the quantity. When mixtures of feed are used, the products tend to be blocky copolymers rather than random copolymers and/or products produced at the beginning of the process are different than that produced at the end of the process, and the inhomogeneous polymer product will be characterized by poor viscosity indices and poor low temperature properties. Thus, in the past, PAOs and HVI-PAOs have typically been made using pure $C_{10}$ feeds. Although, U.S. Pat. No. 7,547,811 discloses mixed feed PAO's made using $AlCl_3$ type catalysts.

One successful example of utilizing mixed feed alpha-olefins to produce HVI-PAOs is the process disclosed in WO 2007/011462 which discloses an improved process wherein mixed alpha-olefin feedstocks are polymerized over an activated metallocene catalyst to provide essentially random liquid polymers particularly useful in lubricant components or as functional fluids. The activated metallocene catalyst can be simple metallocenes, substituted metallocenes or bridged metallocene catalysts activated or promoted by, for instance MAO or a non-coordinating anion.

One problem facing producers of HVI-PAOs is that of reducing the unsaturation of the as-polymerized carbon chains of the PAO products, which can be quantified by Bromine number (ASTM D1159). A PAO fluid cannot be satisfactorily used as a lubricant basestock if its Bromine number exceeds 2. The unsaturation indicated by higher Bromine number can result in poor high temperature stability of the PAO molecules. Accordingly, it is typical to hydrogenate these as-polymerized PAO products in order to reduce the level of unsaturation in the molecules, so as to render them suitable for use as lubricant basestocks. WO 2007/011462 discloses post-oligomerization hydrogenation in order to produce a polyalphaolefin having a Bromine number of less than 1.8.

However, it has been suggested that the oligomerization reaction can be conducted in the presence of low levels of hydrogen, so as to improve catalyst productivity (see, for example, WO 2007/011462 at paragraph [0115]).

U.S. Pat. No. 6,858,767 discloses a process for producing liquid PAO polymer by contacting 1-decene with a particular type of metallocene catalyst, activated with an alkylaluminoxane, in the presence of hydrogen. The resulting product is disclosed to possess a unique combination of properties, such as low molecular weight, low polydispersity index, controllable kinematic viscosity, low Iodine Number and low glass transition temperature. The resulting product is disclosed to be suitable as a viscosity modifier.

Efforts have been made to prepare various PAOs using metallocene catalyst systems. Examples include U.S. Pat. No. 6,706,828 (equivalent to US 2004/0147693), where PAOs are produced from meso-forms of certain metallocene catalysts under high hydrogen pressure. Comparative example D of U.S. Pat. No. 6,706,828, however, uses rac-dimethylsilylbis (2-methyl-indenyl)zirconium dichloride in combination with methylalumoxane (MAO) at 100° C. in the presence of hydrogen to produce polydecene having a reported Kinematic Viscosity at 100° C. ($KV_{100}$) of 116 cSt, a Kinematic Viscosity at 40° C. ($KV_{40}$) of 1039 cSt, a VI of 214, an iodine number of 2.8, an Mw of 7084, an Mn of 2906, an Mw/Mn of 2.4, and a Tg of −72.4° C. Likewise, WO 02/14384 discloses, among other things, in examples J and K the use of rac-ethyl-bis (indenyl)zirconium dichloride or rac-dimethylsilyl-bis(2-methyl-indenyl) zirconium dichloride in combination with MAO at 40° C. (at 200 psi hydrogen or 1 mole of hydrogen) to produce isotactic polydecene reportedly having a Tg of −73.8° C., a $KV_{100}$ of 702 cSt, and a VI of 296; or to produce polydecene reportedly having a Tg of −66° C., a $KV_{100}$ of 1624, and a VI of 341, respectively. Further WO 99/67347 discloses in example 1 the use of ethylidene bis(tetrahydroindenyl)zirconium dichloride in combination with MAO at 50° C. to produce a polydecene having an Mn of 11,400 and 94% vinylidene double bond content.

Others have made various PAOs, such as polydecene, using various metallocene catalysts not typically known to produce polymers or oligomers with any specific tacticity. Examples include WO 96/23751, EP 0 613 873, U.S. Pat. Nos. 5,688,887, 6,043,401, WO 03/020856 (equivalent to US 2003/0055184), U.S. Pat. Nos. 5,087,788, 6,414,090, 6,414,091, 4,704,491, 6,133,209, and U.S. Pat. No. 6,713,438.

U.S. Pat. No. 6,548,724 (equivalent to US 2001/0041817 and U.S. Pat. No. 6,548,723) disclose production of oligomer oils using certain metallocene catalysts, typically in combination with methylalumoxane. Column, 20, line 40 to 44 of U.S. Pat. No. 6,548,724 indicates that Examples, 10-11 indicate that di, tri or tetra substitutions on the cyclopentadienyl rings of the metallocenes are useful for production of high viscosity polyalphaolefins, (viscosities in the range of 20 to 5000 cSt at 100° C.) with improved yields whereas penta alkyl substituted cyclopentadienyl rings are reported as poor.

WO 2007/011459 describes the production of isotactic polyalphaolefins from monomers having 5 to 24 carbon atoms using racemic metallocenes and non-coordinating anion activators.

WO 2007/011973 discloses a process to produce lower viscosity, higher Bromine number polyalphaolefins in the presence of an unbridged substituted metallocene catalyst, a non-coordinating anion activator, and optional hydrogen.

WO 2008/010865 discloses a process to produce high viscosity, atactic PAO fluids in the presence of a metallocene catalyst, a non-coordinating anion activator, and hydrogen.

WO 2009/017953 discloses a process to produce liquid, atactic poly-alphaolefin in the presence of a meso-metallocene catalyst with a non-coordinating anion activator.

WO 2009/137264 and US 2009/0281360 disclose a process to produce a PAO composition having from 0.5 to 5 mole % of mm triads and from 40 to 58 mole % of rr triads, and preferably having from 37 to 59.5 mole % of mr triads. The PAO composition ideally is substantially free of peaks in a region of from 27.0 to 29.0 ppm, and/or in a region of 20.0 ppm and/or in a region of 42.5 ppm in a $^{13}$C NMR spectrum. The PAO composition preferably has a high degree of saturation, and ideally has an Iodine Number of from 0.2 to 5. The PAO composition preferably is formed by polymerizing an olefin monomer, e.g., a $C_8$-$C_{12}$ olefin, preferably 1-decene, in the presence of a metallocene catalyst, preferably a bridged metallocene, and hydrogen.

Other references of interest include: U.S. Pat. Nos. 7,129,197 , 5,177,276, 5,731,254 , 4,892,851, 6,706,828, EP0284708, U.S. Pat. Nos. 5,846,896, 5,679,812, EP0321852, U.S. Pat. No. 4,962,262, EP0513380, US2004/0230016, and U.S. Pat. No. 6,642,169.

To date however, PAO's made with metallocenes have not found wide applicability in the marketplace, particularly the lubricant marketplace, due to inefficient process, cost and property deficits. The instant disclosure address such and other needs by providing new PAO's and or HVI-PAO's having excellent property combinations and an improved process to produce them.

Further, despite recent advances, there remains an unmet need in the art to optimize the polymerization reaction process for producing PAOs, so as to avoid the need for expensive, post-polymerization hydrogen finishing, such that the as-polymerized product is suitable for use as a lubricant basestock. Also, there is a need to improve catalyst productivity, so that the cost for the total catalyst system can be reduced and the catalyst system removal can be simplified. This improved productivity can improve the overall process economics.

SUMMARY

This disclosure relates to liquid syndiotactic polyalphaolefins (sPAO) comprising one or more $C_4$ to $C_{24}$ (preferably $C_6$ to $C_{24}$; preferably $C_8$ to $C_{24}$) monomers, said sPAO having:

a) a rr triad content of 5 to 50% as measured by $^{13}$C NMR;

b) a mr triad content of 25 to 60% as measured by $^{13}$C NMR, where the mr to mm triad ratio is at least 1.0;

c) a pour point of Z° C. or less, where Z=0.0648X-51.2, where X=kinematic viscosity at 100° C. as reported in centistokes (cSt);

d) a kinematic viscosity at 100° C. of 100 cSt or more (alternatively 200 cSt or more);

e) a ratio of mr triads to rr triad (as determined by $^{13}$C NMR) of less than 9;

f) a ratio of vinylidene to 1,2-disubstituted olefins (as determined by $^1$H NMR) of less than 8;

g) a viscosity index of 120 or more; and h) a Mn of 40,000 or less.

This disclosure further relates to process to make and use such sPAO's. The productivity of the process described herein is typically greater than 200 kg of sPAO per gram of transition metal compound, alternatively greater than 250 kg of transition metal compound, alternatively greater than 500 kg/g of transition metal compound, alternatively greater than 1000 g/g of transition metal compound, and/or greater than 10 kg of sPAO per gram of activator, alternatively greater than 50 kg/g of activator, alternatively greater than 100 kg/g of activator, alternatively greater than 500 kg/g of activator.

DETAILED DESCRIPTION

Figure 1:
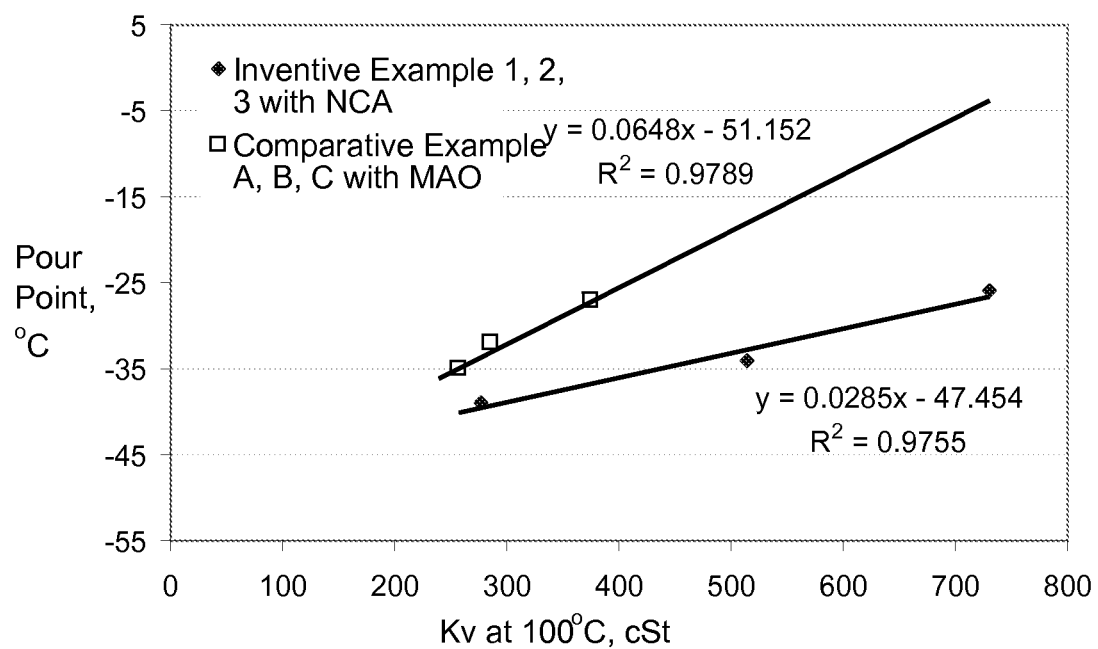
FIG. 1 is a graph of pour point vs. kinematic viscosity at 100° C. for Inventive Examples 1, 2, and 3 vs. Comparative Examples A and B.

All numerical values within the detailed description and the claims herein are modified by "about" or "approximately" the indicated value, and take into account experimental error and variations that would be expected by a person having ordinary skill in the art.

As used herein, the new numbering scheme for the Periodic Table of the Elements is used as set out in CHEMICAL AND ENGINEERING NEWS, 63 (5), 27 (1985).

Unless otherwise stated all pressures in psi are psig and all molecular weights are g/mol.

For purposes of this disclosure and the claims thereto, when a polymer or oligomer is referred to as comprising an olefin, the olefin present in the polymer or oligomer is the polymerized or oligomerized form of the olefin, respectively. Likewise the use of the term polymer is meant to encompass homopolymers and copolymers, where copolymers include any polymer having two or more chemically distinct monomers. Likewise the use of the term oligomer is meant to encompass homooligomers and cooligomers, where cooligomers include any oligomer or having two or more chemically distinct monomers.

For purposes of this disclosure, the term oligomer refers to compositions having 2-75 mer units and the term polymer refers to compositions having 76 or more mer units. A mer is defined as a unit of an oligomer or polymer that originally corresponded to the olefin(s) used in the oligomerization or polymerization reaction. For example, the mer of polydecene would be decene.

For the purposes of this disclosure and the claims thereto the term "Polyalpha-olefin," "polyalphaolefin," or "PAO" includes homooligomers, cooligomers, homopolymers and copolymers of $C_3$ or greater alpha-olefin monomers.

For the purposes of this disclosure and the claims thereto the active species in a catalytic cycle may comprise the neutral or ionic forms of the catalyst.

The term "catalyst system" is defined to mean a catalyst precursor/activator pair, such as a metallocene/activator pair, optionally with co-activator. When "catalyst system" is used to describe such a pair before activation, it means the unactivated catalyst (precatalyst) together with an activator and, optionally, a co-activator (such as a trialkylaluminum compound). When it is used to describe such a pair after activation, it means the activated transition metal catalyst including the charge-balancing moiety if the activated catalyst carries a charge. Additionally, the catalyst system may optionally comprise a co-activator.

"Catalyst precursor" is also often referred to as precatalyst, catalyst, precursor, metallocene, transition metal compound, precatalyst compound, unactivated catalyst, or transition metal complex. These words are used interchangeably. Activator and catalyst are also used interchangeably. A scavenger is a compound that is typically added to facilitate oligomerization or polymerization by scavenging impurities. Some scavengers may also act as activators and may be referred to as co-activators. A co-activator which is not a scavenger may also be used in conjunction with an activator in order to form an active catalyst with a transition metal compound. In some embodiments, a co-activator can be pre-mixed with the transition metal compound to form an alkylated transition metal compound, also referred to as an alkylated catalyst compound or alkylated metallocene. Co-activators are often aluminum alkyls, also referred to as alkyl-aluminums, alkylaluminum compounds, alkylaluminums, or alkylaluminum compounds.

For purposes of this disclosure and the claims thereto non-coordinating anion (NCA) is defined to mean an anion which either does not coordinate to the catalyst metal cation or that coordinates only weakly to the metal cation. An NCA coordinates weakly enough that a neutral Lewis base, such as an olefinically or acetylenically unsaturated monomer, can displace it from the catalyst center. Any metal or metalloid that can form a compatible, weakly coordinating complex with the catalyst metal cation may be used or contained in the non-coordinating anion. Suitable metals include, but are not limited to, aluminum, gold, and platinum. Suitable metalloids include, but are not limited to, boron, aluminum, phosphorus, and silicon. A subclass of non-coordinating anions comprises stoichiometric activators, which can be either neutral or ionic. The terms ionic activator, stoichiometric ionic activator, discrete ionic activator, non-coordinating anion activator, and NCA activator can be used interchangeably. Likewise, the terms neutral stoichiometric activator and Lewis acid activator can be used interchangeably.

In addition, a reactor is any container(s) in which a chemical reaction occurs.

"Isoolefin" is a branched alkene having at least one tertiary or quaternary carbon atom and which possess at least one $C_1$ to $C_{18}$ alkyl branch along at least a portion of each chain. Preferably the alkyl branch is $C_1$ to $C_{12}$.

A "liquid" is defined to be a material that flows at room temperature, having a pour point of less than +20° C. and a kinematic viscosity at 25° C. of 30,000 cSt or less.

Herein this invention, a designated fraction of the product obtained as a PAO, or sPAO, may be referred to as 'lube', 'lube fluid' or 'lube fraction'.

Polyalpha-olefins

This disclosure relates to liquid syndiotactic polyalphaolefins (sPAO) comprising one or more $C_6$ to $C_{24}$ monomers (alternatively $C_6$ to $C_{18}$, alternatively $C_8$ to $C_{14}$, alternatively $C_8$ to $C_{12}$), said sPAO having:

a) an rr triad content of 5 to 50% as measured by $^{13}$C NMR (alternatively from 5 to 45%, alternatively from 5 to 40%);

b) an mr triad content of 25 to 60% as measured by $^{13}$C NMR, where the mr to mm triad ratio is at least 1.0 (alternatively at 1.20, alternatively at 1.5);

c) a pour point of Z ° C. or less, where Z=0.0648X-51.2, (alternatively Z=0.0648-56.2, alternatively Z=0.0648-60.2, alternatively Z=0.0285X-47.5), where X=kinematic viscosity at 100° C. as reported in centistokes (cSt);

d) a kinematic viscosity at 100° C. of 100 cSt or more (alternatively 150 cSt or more, 200 cSt or more, 300 cSt or more, 500 cSt or more, alternatively 600 cSt or more, alternatively 1000 cSt or more, alternatively from 200 cSt to 2000 cSt or from 300 cSt to 2000 cSt, or from 1000 to 2000 cSt);

e) a ratio of mr triads to rr triad (as determined by $^{13}$C NMR) of less than 9 (alternatively from 1 to 8, alternatively from 3 to 7);

f) a ratio of vinylidene to 1,2-disubstituted olefins (as determined by $^1$H NMR) of less than 8 (alternatively from 0.1 to 7, alternatively from 0.1 to 6, alternatively 0.25 to 5, alternatively 0.5 to 4);

g) a viscosity index of 120 or more; and h) an Mn of 40,000 g/mol or less (alternatively from 280 to 35,000 g/mol, alternatively 400 to 30,000 g/mol).

In another embodiment any of the PAO's described herein may have a viscosity index of 150 or more, alternatively, 200 or more, alternatively 300 or more.

In another embodiment, the PAOs described herein, when blended with other basestocks have Brookfield viscosity at −40° C. of less than 150,000 cP.

In another embodiment, the PAOs described herein, when blended with other basestocks have Brookfield viscosity at −55° C. of less than 150,000 cP.

In another embodiment, the sPAOs of this disclosure have excellent low temperature flowability properties, when used as neat base stock or when blended with other base stocks and additives. When tested as a neat base stock, the sPAO produced herein flows readily at room temperature in a simple freeze-thaw cycle test. In this test, approximately 4 ml sPAO in a small test tube of 1.2 cm radius and 5 cm length are cooled with liquid nitrogen down to −70° C. quickly (e.g., less than 1 minute). Nitrogen is removed and the frozen liquid is slowly warmed to room temperature (23° C.). Many fluids with crystallizable fractions of polymers will not fully recover the flowable liquid state when warmed up to room temperature, but instead remain frozen, in this test. While not wishing to be bound by theory, if is believed that this effect is likely due to the cold-crystallization behavior of the fluid. sPAO made in this disclosure, after being frozen at low temperature, will recover its readily flowable state when warmed up to room temperature. This test can be repeated many times (such as 100 times) without affecting the flowability of the sPAO when warmed up to room temperature.

In another embodiment the sPAO described herein, particularly when used in blend stock with other low viscosity base stocks, may also have a Brookfield viscosity of 150,000 cP or less, alternatively 100,000 cP or less, preferably 60,000 cP or less, alternatively 10,000 cP or less, alternatively 7500 cP or less, alternatively 5000 cP or less at −40° C. Typically, for a given 40° C. or 100° C. kinematic viscosity, it is desirable to have lower Brookfield viscosity at −40° C. Brookfield viscosity is determined by the ASTM D2983 test method.

In another embodiment the sPAO described herein particularly when used in blend stock with other low viscosity base stocks, may also have a Brookfield viscosity of 150,000 cP or less, alternatively 100,000 cP or less, alternatively 70,000 cP or less, alternatively 35,000 cP or less at −55° C. For a given 40° C. or 100° C. kinematic viscosity, it is preferable to have lower Brookfield viscosity at −55° C. Lubricants with lower Brookfield viscosity at lower temperature usually have better energy efficiency.

In a preferred embodiment the Brookfield viscosity of the PAO at −40° C. is at least 5,000 cP lower than the Brookfield viscosity of the same PAO at −55° C., alternatively at least 10,000 cP lower, alternatively at least 15,000 lower.

In another embodiment the sPAO described herein has a narrow molecular weight distribution of greater than 1 and less than 5, alternatively less than 4, alternatively less than 3, alternatively less than 2.6. The Mn and Mw are measured by gel permeation chromatography (GPC) using a column for medium to low molecular weight polymers, tetrahydrofuran as solvent and narrow molecular weight distribution polystyrene as calibration standard, correlated with the fluid viscosity according to a power equation. The MWD of sPAO is a function of fluid viscosity. Alternatively any of the polyalphaolefins described herein preferably have an Mw/Mn of between 1 and 2.6, alternatively between 1 and 3.5, depending on fluid viscosity.

The viscosity loss by mechanical shear down of a lubricant or lubricant base stock can be measured by several methods, including Tapered Roller Bearing (TRB) test according to CEC L-45-T-93 procedure, Orbahn (ASTM D3945) or Sonic Shear Tests (ASTM D2603). The TRB test is believed to correlate better to the actual field shear stability performance of viscous fluids than the other shear tests and in event of conflict between the test data, the TRB test shall be used. In one embodiment, the sPOA's produced herein have a 100° C. Kv loss (Tapered Roller Bearing (TRB) test according to CEC L-45-T-93 procedure) of 10% or less, alternatively 5% or less, alternatively 2% or less.

Figure 2:
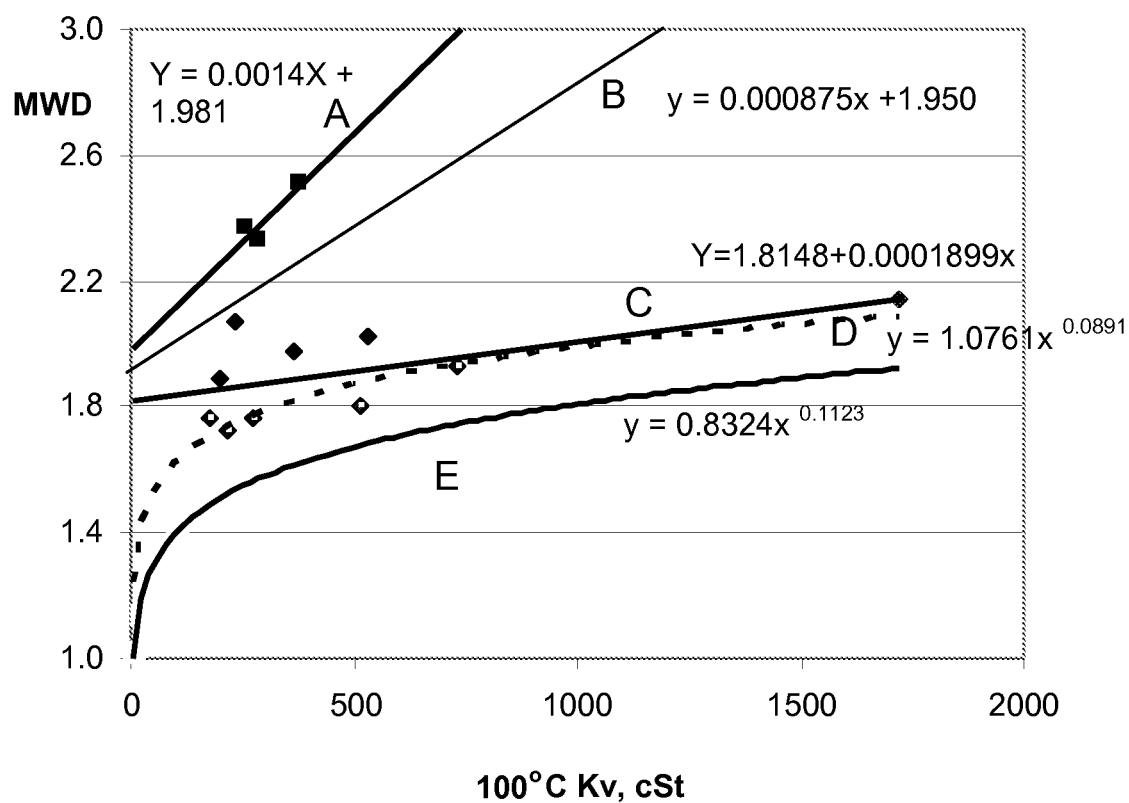
FIG. 2 is a graph showing various Mw/Mn limits for sPAO's of this disclosure and comparative PAO's.

The sPAOs produced herein consistently have lower MWDs than PAOs produced in the art, using different catalyst compositions. In one embodiment the sPAOs described herein have an MWD of equal to or less than $1.950 + 0.000875 \times (100° C. Kv, cSt)$, as depicted by Line B in FIG. 2. The MWD of the PAOs made in this disclosure have values less than Line B. In one embodiment, the PAO's disclosed herein have an MWD value below a value of $1.8148 + 0.0001899 \times (100° C. Kv, cSt)$ as depicted by Line C of FIG. 2. The average lower limit MWD of the sPAOs made in this disclosure is equal or approximately equal to $1.0761 \times (100° C. Kv, cSt)^{(0.0891)}$ as depicted by Line D of FIG. 2. The lowest limit of MWD of fluids made in this disclosure is greater than or equal to $0.83242 \times (100° C. Kv, cSt)^{(0.11231)}$ as depicted by Line E of FIG. 2. In another option, the lower the MWD value, the better the sPAO is for lube applications. Generally, any lube with MWD of lower than the value defined by line B will be more desirable. The comparative Example A to C products, discussed later herein and represented in FIG. 2 by the solid squares, generally have higher MWDs having values greater than or equal to $1.981 + 0.0013816 \times (100° C. Kv, cSt)$, as depicted by Line A of FIG. 2. This is indicative of broader molecular weight distribution, which is less desirable.

Figure 3:
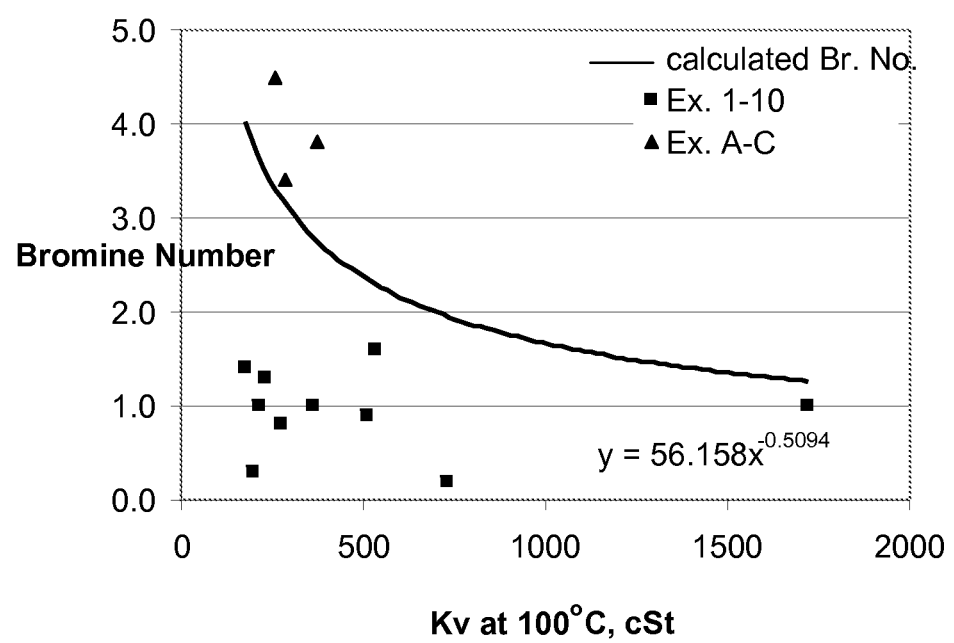
FIG. 3 is a graph of Bromine numbers for examples 1 to 10 and comparative examples A to C.

In another aspect, the disclosure relates to a high (greater than 200) viscosity index syndiotactic polyalphaolefin (HVI-sPAO) liquid comprising polymers or oligomers of one or more $C_6$ to $C_{14}$ alpha-olefins having an as-polymerized Bromine number of less than 2, preferably between 0.2 to 1.6. The 'as-polymerized' Bromine number is the Bromine number of the material exiting the polymerization reactor and before contact with a hydrogenation catalyst. When a polymer is synthesized from 1-decene with any pre-hydrogenation, each polymer or oligomer will contain one unsaturated double bond. In this completely un-hydrogenated polyalphaolefin, the lube product Bromine number can be predicted by the following equation: Bromine number=$56.158 \times (100° C. Kv$ in $cSt)^{(-0.50939)}$. When un-expected hydrogenation occurs, the product Bromine number will be significantly less than this amount. FIG. 3 shows that Example 1 to 10 have significantly lower Bromine number than calculated based on viscosity. In contrast, the comparative Examples A to C have higher Bromine number.

The Bromine numbers of our inventive sPAO's usually are less than the calculated Bromine number of $56.158 \times (100° C. Kv$ in $cSt)^{(-0.50939)}$. In a preferred embodiment, the Bromine number of the sPAOs of this disclosure are at least 10% lower than the calculated Bromine number ($56.158 \times (100° C. Kv$ in $cSt)^{(-0.50939)}$), preferably at least 25% lower, preferably at least 50% lower. It is preferable to have a Bromine number of less than 3 or more preferably less than 2. Lower Bromine number indicates higher degree of saturation, which is usually indicative of higher oxidative stability and high quality of base stock. Bromine number is measured by ASTM D1159.

In another embodiment, any of the polyalpha-olefins produced herein preferably have a Bromine number of 1.8 or less as measured by ASTM D1159, preferably 1.7 or less, preferably 1.6 or less, preferably 1.5 or less, preferably 1.4 or less, preferably 1.3 or less, preferably 1.2 or less, preferably 1.1 or less, preferably 1.0 or less, preferably 0.5 or less, preferably 0.1 or less.

In another embodiment, the sPAO is a high viscosity index sPAO (HVI-sPAO) and has a $KV_{100}$ of 100 cSt or more, alternatively 600 cSt or more, alternatively 1000 cSt or more, with a VI of 170 or more, alternatively 250 or more, alternatively 500 or more. Usually base stock VI is a function of fluid viscosity, as shown in Examples 1 to 10. Usually, the higher the VI, the better it is for lube application. Base Stock VI also depends on feed composition. Fluids made from single 1-hexene, 1-octene, 1-decene, 1-dodecene or 1-tetradecene usually have excellent VI and good pour point. Fluids made from two or more olefins selected from $C_3$ to $C_{18}$ alpha-olefins generally have excellent VI and superior pour points if the average carbon chain length of feed LAOs is kept within 6 to 12 carbons. A relatively much lower average chain length in the feed (much below 5.5 carbons) of the mixed LAO would result in lower VI. Too high of a average chain length in the feed (much above 12 carbons) of the mixed LAO would result in very high pour point, around room temperature. If high pour point is tolerable, such as in certain formulation when the sPAO is blended with other base stock, high average length of feed LAO can be acceptable as feed.

The syndiotactic PAO can comprise a single alpha-olefin monomer type, or may comprise two or more different alpha-olefin monomers. In one embodiment, this disclosure relates to syndiotactic polyalpha-olefins (sPAO's) comprising a molar amount of $C_6$ to $C_{24}$ alpha-olefin monomers selected from the group consisting of 55 mol % or more, 60 mol % or more, 65 mol % or more, 70 mol % or more, 75 mol % or more, 80 mol % or more, 85 mol % or more, 90 mol % or more, 95 mol % or more, 100 mol %, all based on the total moles of monomers present in the polyalpha-olefin, as measured by $^{13}C$ NMR. When two or more alpha-olefin monomers are present, it is sometimes desirable to add propylene, or butene (typically 1-butene) olefins into the feed. Use of these smaller olefins in the feed offers the advantage of lower feed cost and/or more abundant feed source. When adding $C_3$ or 1-$C_4$ olefins as one of the feed components, it is important to maintain the total average carbon chain length of the feed LAO (Linear Alpha Olefin) between 5.5 to 12.5 carbons. It is preferably to be in 6 to 12 range, or preferably to be in 8 to 11 range, or more preferably in 9 to 10.5 range.

In one or more embodiments, the sPAO comprises $C_{15}$ to $C_{1500}$, or $C_{20}$ to $C_{1000}$, or $C_{30}$ to $C_{800}$, or $C_{35}$ to $C_{400}$, or $C_{40}$ to $C_{250}$ oligomers (such as dimers, trimers, etc.) of one or more alpha-olefins (also known as 1-olefins) with carbon numbers of $C_2$ to $C_{24}$, or $C_3$ to $C_{20}$, or $C_5$ to $C_{18}$, or $C_6$ to $C_{14}$, or $C_8$ to $C_{12}$. Preferably, at least one of the alpha-olefins is a linear alpha-olefin (LAO); more preferably, all the alpha-olefins are LAOS. Suitable LAOs include ethylene, propylene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, and blends thereof. Preferably, $C_2$, $C_3$, and $C_4$ alpha-olefins (i.e., ethylene, propylene and 1-butene) are present in the PAO oligomers at an average concentration of 30 wt % or less, or 20 wt % or less, or 10 wt % or less, or 5 wt % or less; more preferably, $C_2$, $C_3$, and $C_4$ alpha-olefins are not present in the PAO oligomers.

In one or more embodiments, the PAO comprises oligomers of two or more $C_2$ to $C_{24}$, or $C_4$ to $C_{20}$ LAOS, to make 'copolymer' or 'terpolymer' or higher-order copolymer combinations. Other embodiments involve oligomerization of a mixture of LAOs selected from $C_6$ to $C_{18}$ LAOs with even carbon numbers, preferably a mixture of two or three LAOs selected from 1-hexene, 1-octene, 1-decene, 1-dodecene, and 1-tetradecene.

In one or more embodiments, the PAO comprises oligomers of a single alpha-olefin species having a total carbon count of 5 to 20, or 6 to 18, or 8 to 12, or 10. In other embodiments, the PAO comprises oligomers of mixed (i.e., two or more) alpha-olefin species, wherein each alpha-olefin species has a carbon number of 5 to 20, or 6 to 14, or 8 to 12. In other embodiments, the PAO comprises oligomers of mixed alpha-olefin species wherein the molar-average carbon number ("$C_{LAO}$") is 6 to 14, or 7 to 13, or 8 to 12, or 9 to 11.

In another embodiment this disclosure further relates to sPAO's having 4 mol % or more of rr triads, preferably 5% or more, preferably 8% or more, preferably 10% or more, preferably 12% or more, preferably, as determined by $^{13}C$ nuclear magnetic resonance (NMR) spectroscopy according to the procedure below.

In another embodiment, this disclosure is further related to sPAO's (typically hydrogenated sPAO's) having 60% mm triads or less, or 50% mm triads or less, or 40% mm triads or less, 30% or less mm triads, or 20% mm triads or less.

In one embodiment, the polyalphaolefins according to the present disclosure have a ratio of mr to rr triads of less than 9, preferably from 1 to 8 preferably from 3 to 7. In another embodiment, the preferred range is from 1.0 to 9, or from 2 to 8, or from 2 to 7, as measured by $^{13}C$ NMR. In another embodiment, the hydrogenated polyalphaolefins according to the present disclosure have a ratio of rr to mr triads of less than 1, with preferred range from 0.1 to 0.9.

NMR spectroscopy provides structural information about the synthesized polymers. Proton NMR analysis of the unhydrogenated sPAO gives a quantitative breakdown of the olefinic structure types (viz. vinyl, 1,2-disubstituted, trisubstituted, and vinylidene). As noted above, $^{13}C$ NMR is used to determine tacticity of the polyalphaolefins of the present disclosure—quantitatively in some cases, and qualitatively in others. $^{13}C$ NMR can be used to determine the concentration of the triads, denoted mm (meso, meso), mr (meso, racemic) and rr (racemic, racemic), as well as the molar composition of the sample. The concentrations of these triads define whether the polymer is isotactic, atactic or syndiotactic. Spectra for a sPAO sample are acquired in the following manner. Approximately 100-1000 mg of the sPAO sample is dissolved in 2-3 ml of chloroform-d for $^{13}C$ analysis. Approximately 10 mg/ml (solvent basis) of chromium acetylacetonate relaxation agent, Cr(acac)$_3$, is added to the sample to enhance the data acquisition rate. Analysis of the spectra is performed according to the paper by Kim, I.; Zhou, J.-M.; and Chung, H. *Journal of Polymer Science: Part A: Polymer Chemistry* 2000, 38 1687-1697, augmented by the identification and integration of end group resonances, and removal of their contributions to the peaks used in the analysis. The deconvolutions are executed with Acorn NMR Inc.'s NutsPro NMR data analysis software, using an 85/15 Lorentzian/Gaussian lineshape. The component peaks are lumped together into clusters according to the mm, mr, and rr triad assignments, and fit with a Bernoullian distribution. The adjustable parameter for these fits is $P_r$, the fraction of monomer added with racemic stereochemistry. For details of going from a set of triad measurements (such as described by Kim above) to a statistical model (such as the Bernoullian) see *Polymer Sequence Determination*, James C. Randall, Academic Press, New York, 1977.

In another embodiment, any of the polyalpha-olefins produced herein preferably have 1,2 disubstituted olefins present at 10 mole % or more, based upon the total moles of all double bonds present in the poly-alpha-olefin as measured by Proton NMR, preferably 15 mole % or more, preferably 20 mole % or more, preferably 30 mole % or more, preferably 40 mole % or more.

The proton NMR analysis (used to measure 1,2-disubstitutions and the units represented by the formula above) is performed by dissolving the sample in appropriate deuterated solvent (e.g., chloroform-d), and acquiring a pulse-acquire experiment of sufficient signal-to-noise ratio to allow integration of the olefin region (approximately 6 ppm to 4.6 ppm). The spectra are acquired at a temperature of 50° C., with the temperature chosen to ensure complete sample dissolution (if the sample is not completely dissolved at 50° C., then the temperature is raised slowly until the sample is completely dissolved). The aliphatic region of the proton spectrum comprises the signal from the saturated components, and the olefinic region from the unsaturated end of the polymer. In cases where multiple alphaolefins are copolymerized, it may be possible to determine the composition of the polymer from the branch methyl resonances of the differing alphaolefin branches. This composition determination can be executed if the methyl peaks (resonating between 1.0 and 0.6 ppm) are sufficiently resolved to allow direct integration, or spectral deconvolution.

The olefinic region can be integrated piecewise according to the chemical shift assignments tabulated below:

| Olefin type | Chemical shift range (ppm) | Number of protons |
|---|---|---|
| Vinyl - first region | 5.7-5.9 | 1 |
| Vinyl - second region | 4.8-5.3 | 2 |
| 1,2-disubstituted | 5.3-5.6 | 2 |
| Trisubstituted | 4.8-5.3 | 1 |
| Vinylidene (1,1-disubstituted) | 4.6-4.8 | 2 |

The olefin subintegrals are corrected for the proton multiplicity of the contributing species, and for overlapping contributions (e.g., both vinyl and trisubstituted olefins in the 5.3-4.8 ppm region). The integral values resulting from this correction can then be normalized to give the mole-percentage of each olefin class. Comparison of the corrected integral values with the aliphatic integral intensity (also multiplicity-corrected) can be used to determine the olefin concentrations on an absolute basis (e.g., olefins per 1000 carbons).

In another embodiment, any of the polyalpha-olefins described herein, neat from the polymerization reactor, have less than 300 ppm of any group 4 metals (preferably Ti, Hf or Zr), or less than 200 ppm, or less than 100 ppm, or less than 50 ppm, or less than 10 ppm, as measured by ASTM D5185.

In another embodiment, any of the polyalpha-olefins described herein have less than 300 ppm of any group 13 metals (preferably B or Al), or less than 200 ppm, or less than 100 ppm, or less than 50 ppm, or less than 10 ppm, as measured by ASTM D5185.

In another embodiment, any of the polyalpha-olefins described herein have less than 600 ppm of aluminum, or less than 500 ppm, or less than 600 ppm, or less than 300 ppm, or less than 300 ppm, or less than 10 ppm, or less than 50 ppm, or less than 10 ppm, as measured by ASTM D5185.

In another embodiment, any of the polyalpha-olefins described herein have an Mw of 100,000 g/mol or less, or between 200 and 80,000 g/mol, or between 250 and 60,000 g/mol, or between 280 and 50,000 g/mol, or between 336 and 40,000 g/mol. Preferred Mw's include those from 224 to 55,100 g/mol, or from 392 to 30,000 g/mol, or 800 to 24,000 g/mol, or 2,000 to 37,500 g/mol. Alternatively preferred Mw's include 224 to 6790 g/mol and 224 to 2720 g/mol.

In another embodiment, any of the polyalpha-olefins described herein preferably have an Mn of 50,000 g/mol or less, or 40,000 g/mol or less, or between 200 and 40,000 g/mol, or between 250 and 30,000 g/mol, preferably between 500 and 20,000 g/mol. Preferred Mn ranges include those from 280 to 10,000 g/mol or from 280 to 4,000 g/mol. Alternatively preferred Mn ranges are from 200 to 20,900 g/mol, or 280 to 10,000 g/mol, or 200 to 7000 g/mol, or 200 to 2000 g/mol, or 280 to 2900 g/mol, or 280 to 1700 g/mol, or 200 to 500 g/mol.

The Mw, Mn, and Mz are measured by GPC using a column for medium to low molecular weight polymers, tetrahydrofuran as solvent and polystyrene as calibration standard, correlated with the fluid viscosity according to a power equation.

This relationship of Mw vs. 100° C. kinematic viscosity in cSt for fluids prepared in this disclosure using 1-decene as feed is as follows: Mw=410.31×(100° C. vis in cSt)$^{0.60434}$ Similarly, the relationship of Mw vs. 100° C. kinematic viscosity in cSt for fluids prepared in this disclosure using 1-hexene as feed is as following: Mw=410.31×(100° C. vis in cSt)$^{0.477}$. When other alpha-olefins are used as feed, this Mw vs. 100° C. viscosity relationship may change slightly. It is expected similar type of relationship will hold. Unless otherwise indicated Mw values reported herein are GPC values and not calculated from the kinematic viscosity measured at 100° C.

In a preferred embodiment of this disclosure, any sPAO described herein may have a pour point of less than 0° C. (as measured by ASTM D97), preferably less than −10° C., preferably less than −20° C., preferably less than −25° C., preferably less than −30° C., preferably less than −35° C., preferably less than −50° C., preferably between −10° C. and −80° C., preferably between −15° C. and −70° C.

In another embodiment according to the present disclosure, any sPAO described herein may have a kinematic viscosity at 100° C. in any of the following ranges: from 100 to 5,000 cSt, from 175 to 3,000 cSt, from 200 cSt to 1,500 cSt, from 300 cSt to 1,000 cSt, from 100 cSt to 800 cSt, from 175 cSt to 800 cSt, from 200 cSt to 800 cSt, from 100 cSt to 650 cSt wherein all values are measured by ASTM D445.

In another embodiment according to the present disclosure any polyalpha olefin described herein may have a kinematic viscosity at 100° C. from 3 to 10 cSt and a flash point of 150° C. or more, preferably 200° C. or more (as measured by ASTM D56).

In another embodiment according to the present disclosure any polyalpha olefin described herein may have a flash point of 200° C. or more, alternatively 220° C. or more, preferably 250° C. or more.

In another embodiment according to the present disclosure any polyalpha olefin described herein may have a dielectric constant of 2.5 or less (1 kHz at 23° C. as determined by ASTM D924).

In another embodiment according to the present disclosure any polyalpha olefin described herein may have a density of 0.75 to 0.96 g/cm$^3$, preferably 0.80 to 0.94 g/cm$^3$, alternatively from 0.76 to 0.855 g/cm$^3$.

In another embodiment according to the present disclosure any polyalpha olefin described herein may have a specific gravity of 0.75 to 0.96, preferably 0.80 to 0.94, alternatively from 0.76 to 0.87.

The high viscosity sPAO's of this disclosure are desirable for use as blend stock with API Groups I to V or gas-to-liquid (GTL) derived lube base stocks for use in industrial and automotive engine or gear oil, especially certain high $KV_{100}$ grades of 40 to 1000 cSt which are especially desirable for use as blend stock with Groups I to V or GTL-derived lube base stocks for use in industrial and automotive engine or gear oil. They are also suitable for use in personal care applications, such as blends with soaps, detergents, other emollients, for use in personal care creams, lotions, sticks, shampoos, detergents, etc.

In another embodiment according to the present disclosure, any polyalpha olefin described herein has a viscosity index (VI) of 100 or more, or 120 or more, or 130 or more; alternatively, from 120 to 450, alternatively from 100 to 400, alternatively from 120 to 380, alternatively from 100 to 300, alternatively from 140 to 380, alternatively from 180 to 306, alternatively from 252 to 306, alternatively the viscosity index is at least 165, alternatively at least 187, alternatively at least 200, alternatively at least 252. Viscosity index is determined according to ASTM Method D2270-93 [1998].

One embodiment according to the present disclosure is a new class of poly-alpha-olefins, which have uniform head-to-tail connections of most of the monomers in the chain and a unique chemical feature characterized by a unique head-to-head connections at the end position of some polymer chain. This new class of poly-alpha-olefins is further characterized by a high degree of stereoselectivity, that is, they have relatively high amount of rr connection (or syndiotactic connection). The new poly-alpha-olefins when used by themselves or blended with other fluids have unique lubrication properties. The term "head-to-head connection" refers to a connection formed on at least one end of the sPAO oligomer or polymer in which the penultimate olefin inserted 1,2 and the last olefin inserted 2,1 into the oligomer or polymer chain. The term "head-to-tail connection" refers to a connection formed on at least one end of the sPAO oligomer or polymer in which the penultimate olefin inserted in 1,2 insertion and the last olefin also inserted in 1,2-insertion into the oligomer or polymer chain.

The sPAO's produced according to this disclosure are typically dimers, trimers, tetramers, or higher oligomers of one or more $C_5$ to $C_{24}$ olefin monomers, preferably one or more $C_5$ to $C_{24}$ alpha-olefin monomers, and preferably one or more $C_5$ to $C_{24}$ linear alpha-olefin monomers. Alternatively, an alpha-olefin with alkyl substitutent at least 2 carbons away from the olefinic double bond can also be used. Typically, the sPAO's produced herein are usually a mixture of many different oligomers. The smallest oligomers from these alpha-olefins have carbon number ranging from $C_{10}$ to $C_{20}$. These small oligomers are usually too light for most high performance fluids application. They are usually separated from the higher oligomers with carbon number of greater than $C_{20}$, for example $C_{24}$ and higher which are more preferred as high performance fluids. These separated $C_{10}$ to $C_{20}$ oligomer olefins or the corresponding paraffins after hydrogenation can be used in specialty applications, such as drilling fluids, solvents, paint thinner, etc with excellent biodegradability, toxicity, viscosities, etc. The unhydrogenated olefins maybe used as starting material in the production of detergents, dispersants, lube or fuel additives, alcohols, acids, functional fluids, etc. The fluid fraction in the $C_{20}$ to $C_{30}$ with low Bromine number or treated to give low Bromine number, typically has a lower viscosity making it beneficial for some applications, such as lubricants with better fuel economy, better biodegradability, better low temperature flow properties, or lower volatility. The higher viscosity product, usually has a much higher average degree of polymerization and a very low amount of $C_{20}$ to $C_{30}$ component. These high viscosity fluids are excellent blend stocks for lube application to improve the viscosity. Because of their usually narrow molecular weight distribution, they have superior shear stability. The shear stability of these fluids, in the pure form or preferably in blends with other lower viscosity base stocks, can be measured by the sonic shear test (ASTM D2603) or by Diesel injector nozzle test (ASTM D3945) or by Tapered Roller Bearing (TRB) Shear Test (CEC L-45-T-93) or other equivalent methods. The TRB test is usually the preferred test because it gives the best correlation to actual field performance. The fluids made in this disclosure usually have better shear stability than fluids made in prior art, especially those fluids made using methylalumoxane as one of the catalyst components. Also, because of their unique chemical composition with high degree of un-isomerized long-chain branches, the new fluids described here have excellent viscometrics and unexpected low traction properties.

These higher viscosity sPAO can be used as superior blend stocks. They can be blend stocks with any of the API Group I to V and GTL fluids to give the optimum viscometrics, solvency, high and low temperature lubricity, etc. When further blended with proper additives, including antioxidants, anti-wear additives, friction modifiers, dispersants, detergents, corrosion inhibitors, defoamants, extreme pressure additives, seal swell additives, and optionally viscosity modifiers, etc. Description of typical additives can be found in the book "Lubricant Additives: Chemistry and Applications," L. R. Rudnick, ed. Marcel Dekker Inc., New York, 2001.

Process

One embodiment of the present disclosure discloses an improved process to produce a new class of poly-alpha-olefins having unique chemical compositions. This improved process employs transition metal catalysts together with one or more activators (such as a non-coordinating anion). Some transition metal catalysts contain a $C_s$-symmetric active center, which favors the formation of PAO with syndiotactic stereo arrangement of the monomer. One aspect of the processes described herein also includes an optional treatment of the feed olefins to remove catalyst poisons, such as peroxides, oxygen, sulfur, nitrogen-containing organic compounds, and or acetylenic compounds. This treatment is believed to increase catalyst productivity, typically more than 5 fold, preferably more than 10 fold.

In a preferred embodiment, this disclosure relates to a process to produce a polyalpha-olefin comprising:

1) contacting at least one alpha-olefin monomer having 3 to 24 carbon atoms with a precatalyst compound (as described below) and an activator under polymerization conditions wherein hydrogen, if present, is present at a partial pressure of 200 psi (1379 kPa) or less, based upon the total pressure of the reactor, or alternatively 150 psi (1034 kPa) or less, or 100 psi (690 kPa) or less, or 50 psi (345 kPa) or less, or 25 psi (173 kPa) or less, or 10 psi (69 kPa) or less; alternatively if the hydrogen is present in the reactor, it is present in amounts of 1000 ppm or less by weight, or 750 ppm or less, or 500 ppm or less, or 250 ppm or less, or 100 ppm or less, or 50 ppm or less, or 25 ppm or less, or 10 ppm or less, or 5 ppm or less, and wherein the alpha-olefin monomer having 5 to 24 carbon atoms is present at 10 volume % or more based upon the total volume of the catalyst/activator/co-activator solutions, monomers, and any diluents or solvents present in the reaction; and 2) obtaining a polyalpha-olefin with Bromine number of less than 4, alternatively less than 3, alternatively less than 2, alternatively less than 1 for the as-polymerized PAO, optionally hydrogenating the sPAO and obtaining a sPAO comprising at least 50 mole % of a $C_3$ to $C_{24}$ alpha-olefin monomer, wherein the polyalpha-olefin has a kinematic viscosity at 100° C. of 5000 cSt or less, and the polyalpha-olefin comprises at least 8% of the polymer with mr stereo-arrangement, preferably more than 10%, more preferably more than 12%, wherein the polyalpha-olefin has mostly head-to-tail connections (i.e., greater than 50%), with some polymer also contains head-to-head connections at the end of the polymer chain.

In an alternative embodiment, this disclosure relates to a process to produce a polyalpha-olefin comprising:

1) contacting a feed stream comprising at least one alpha-olefin monomer having 2 to 24 carbon atoms with a metallocene catalyst compound and a non-coordinating anion activator and optionally an alkyl-aluminum compound, under polymerization conditions wherein the alpha-olefin monomer having 2 to 24 carbon atoms is present at 10 volume % or more based upon the total volume of the catalyst/activator/co-activator solution, monomers, and any diluents or solvents present in the reactor and where the feed alpha-olefin, diluent or solvent stream comprises less than 300 ppm of heteroatom containing compounds; and obtaining a polyalpha-olefin comprising at least 50 mole % of a $C_6$ to $C_{24}$ alpha-olefin monomer where the polyalpha-olefin has a kinematic viscosity at 100° C. of 5000 cSt or less. If hydrogen is present, it is present in the reactor at 1000 ppm or less by weight, alternatively 750 ppm or less, alternatively 500 ppm or less, alternatively 250 ppm or less, alternatively 100 ppm or less, alternatively 50 ppm or less, alternatively 25 ppm or less, alternatively 10 ppm or less, alternatively 5 ppm or less.

In an alternative embodiment, this disclosure relates to a process to produce a polyalpha-olefin comprising:

1) contacting a feed stream comprising at least one alpha-olefin monomer having 6 to 24 carbon atoms with a metallocene catalyst compound and a non-coordinating anion activator, and optionally an alkyl-aluminum compound, under polymerization conditions wherein the alpha-olefin monomer having 2 to 24 carbon atoms is present at 10 volume % or more based upon the total volume of the catalyst/activator/co-activator solution, monomers, and any diluents or solvents present in the reactor and where the feed alpha-olefin, diluent or solvent stream comprises less than 300 ppm of heteroatom containing compounds which; and obtaining a polyalpha-olefin comprising at least 50 mole % of a $C_2$ to $C_{24}$ alpha-olefin monomer where the polyalpha-olefin has a kinematic viscosity at 100° C. of 5000 cSt or less;

2) isolating the lube fraction polymers (also referred to as 'lube', 'lube fluid' or 'lube fraction') and using these polymers as lubricant base stock after distillation when the polymer has Bromine number less than 4, alternatively less than 3, alternatively less than 2 or alternatively less than 1; or alternatively, if the Bromine number is significantly higher than 2 or 3 or 4, then contacting this lube fraction with hydrogen under typical hydrogenation conditions with hydrogenation catalyst to give fluid with Bromine number below 2.

Alternatively, in any process described herein hydrogen, if present, is present in the reactor at 1000 ppm or less by weight, or 750 ppm or less, or 500 ppm or less, or 250 ppm or less, or 100 ppm or less, or 50 ppm or less, or 25 ppm or less, or 10 ppm or less, or 5 ppm or less. Alternatively, in any process described herein hydrogen, if present, is present in the feed at 1000 ppm or less by weight, or 750 ppm or less, or 500 ppm or less, or 250 ppm or less, or 100 ppm or less, or 50 ppm or less, or 25 ppm or less, or 10 ppm or less, or 5 ppm or less.

Unless otherwise stated all pressures in psi are psig.

Catalyst Compounds

For purposes of this invention and the claims thereto, the terms "hydrocarbyl radical," "hydrocarbyl," and "hydrocarbyl group" are used interchangeably throughout this document. Likewise the terms "group," "radical," and "substituent" are also used interchangeably throughout this document. For purposes of this disclosure, "hydrocarbyl radical" is defined to be a $C_1$-$C_{100}$ radical and may be linear, branched, or cyclic. When cyclic, the hydrocarbon radical may be aromatic or non-aromatic. "Hydrocarbon radical" is defined to include substituted hydrocarbyl radicals, halocarbyl radicals, substituted halocarbyl radicals, silylcarbyl radicals, and germylcarbyl radicals as these terms are defined below. Substituted hydrocarbyl radicals are radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-hydrocarbon atom or group has been inserted within the hydrocarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

Halocarbyl radicals are radicals in which one or more hydrocarbyl hydrogen atoms have been substituted with at least one halogen (e.g. F, Cl, Br, I) or halogen-containing group (e.g. $CF_3$).

Substituted halocarbyl radicals are radicals in which at least one halocarbyl hydrogen or halogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

Silylcarbyl radicals (also called silylcarbyls) are groups in which the silyl functionality is bonded directly to the indicated atom or atoms. Examples include $SiH_3$, $SiH_2R^*$, $SiHR^*_2$, $SiR^*_3$, $SiH_2(OR^*)$, $SiH(OR^*)_2$, $Si(OR^*)_3$, $SiH_2(NR^*_2)$, $SiH(NR^*_2)_2$, $Si(NR^*_2)_3$, and the like where R* is independently a hydrocarbyl or halocarbyl radical and two or more R* may join together to form a substituted or unsubstituted saturated, partially unsaturated or aromatic cyclic or polycyclic ring structure.

Germylcarbyl radicals (also called germylcarbyls) are groups in which the germyl functionality is bonded directly to the indicated atom or atoms. Examples include $GeH_3$, $GeH_2R^*$, $GeHR^*_2$, $GeR^5_3$, $GeH_2(OR^*)$, $GeH(OR^*)_2$, $Ge(OR^*)_3$, $GeH_2(NR^*_2)$, $GeH(NR^*_2)_2$, $Ge(NR^*_2)_3$, and the like where R* is independently a hydrocarbyl or halocarbyl radical and two or more R* may join together to form a substituted or unsubstituted saturated, partially unsaturated or aromatic cyclic or polycyclic ring structure.

Polar radicals or polar groups are groups in which a heteroatom functionality is bonded directly to the indicated atom or atoms. They include heteroatoms of groups 1-17 of the periodic table (except carbon and hydrogen) either alone or connected to other elements by covalent bonds or other interactions such as ionic bonds, van der Waals forces, or hydrogen bonding. Examples of functional heteroatom containing groups include carboxylic acids, acid halides, carboxylic esters, carboxylic salts, carboxylic anhydrides, aldehydes and their chalcogen (group 14) analogues, alcohols and phenols, ethers, peroxides and hydroperoxides, carboxylic amides, hydrazides and imides, amidines and other nitrogen analogues of amides, nitriles, amines and imines, azos, nitros, other nitrogen compounds, sulfur acids, selenium acids, thiols, sulfides, sulfoxides, sulfones, phosphines, phosphates, other phosphorus compounds, silanes, boranes, borates, alanes, aluminates. Functional groups may also be taken broadly to include organic polymer supports or inorganic support material such as alumina, and silica. Preferred examples of polar groups include $NR^*_2$, $OR^*$, $SeR^*$, $TeR^*$, $PR^*_2$, $AsR^*_2$, $SbR^*_2$, $SR^*$, $BR^*_2$, $SnR^*_3$, $PbR^*_3$ and the like where R* is independently a hydrocarbyl, substituted hydrocarbyl, halocarbyl or substituted halocarbyl radical as defined above and two R* may join together to form a substituted or unsubstituted saturated, partially unsaturated or aromatic cyclic or polycyclic ring structure.

In using the terms "substituted or unsubstituted cyclopentadienyl ligand", "substituted or unsubstituted indenyl ligand", and "substituted or unsubstituted tetrahydroindenyl ligand", the substitution to the aforementioned ligand may be hydrocarbyl, substituted hydrocarbyl, halocarbyl, substituted halocarbyl, silylcarbyl, or germylcarbyl. The substitution may also be within the ring giving heterocyclopentadienyl ligands, heteroindenyl ligands or heterotetrahydroindenyl ligands, each of which can additionally be substituted or unsubstituted.

In some embodiments, the hydrocarbyl radical is independently selected from methyl, ethyl, ethenyl, and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, triacontynyl, butadienyl, pentadienyl, hexadienyl, heptadienyl, octadienyl, nonadienyl, and decadienyl. Also included are isomers of saturated, partially unsaturated and aromatic cyclic and polycyclic structures wherein the radical may additionally be subjected to the types of substitutions described above. Examples include phenyl, methylphenyl, dimethylphenyl, ethylphenyl, diethylphenyl, propylphenyl, dipropylphenyl, benzyl, methylbenzyl, naphthyl, anthracenyl, cyclopentyl, cyclopentenyl, cyclohexyl, cyclohexenyl, methylcyclohexyl, cycloheptyl, cycloheptenyl, norbornyl, norbornenyl, adamantyl and the like. For this disclosure, when a radical is listed, it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

Examples of cyclopentadienyl and indenyl ligands are illustrated below as anionic ligands. The ring numbering scheme is also illustrated. When a cyclopentadienyl ligand has one bridging substituent, the bridging substituent is in the one position. When a cyclopentadienyl ligand has two bridging substituents, the bridging substituents are in the one and two positions. When a fluorenyl ligand has a bridging substituent, the bridging substituent is in the nine position. When dibenzo[b,h]fluorene has a bridging substitutent, the bridging substituent is in the twelve position.

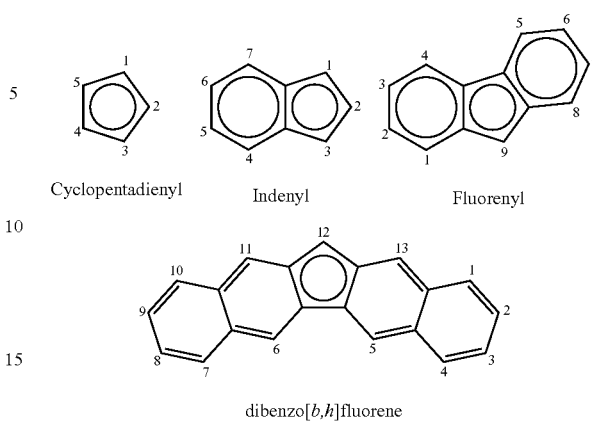

Cyclopentadienyl   Indenyl   Fluorenyl dibenzo[b,h]fluorene

A similar numbering and nomenclature scheme is used for heterocyclopentapentalenyls, heterofluorenyls, and the like, as illustrated below. Each structure illustrated is drawn as an anion.

Non-limiting examples of heterocyclopentapentalenyls include the following, where Q represents the heteroatoms O, S, Se, or Te, or heteroatom groups, NR, PR, AsR, or SbR where R** is hydrogen, or a hydrocarbyl, substituted hydrocarbyl, halocarbyl, substituted halocarbyl, silylcarbyl, or germylcarbyl substituent. When a heterocyclopentapentalenyl ligand has a bridging substituent, the bridging substituent is in the seven position.

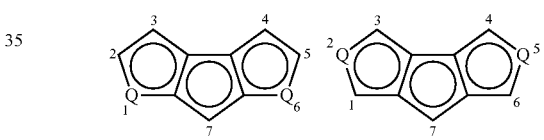

Non-limiting examples of heterofluorenyls where Z represents the heteroatoms N or P include the following. When a heterofluorenyl ligand has a bridging substituent, the bridging substituent is in the five position.

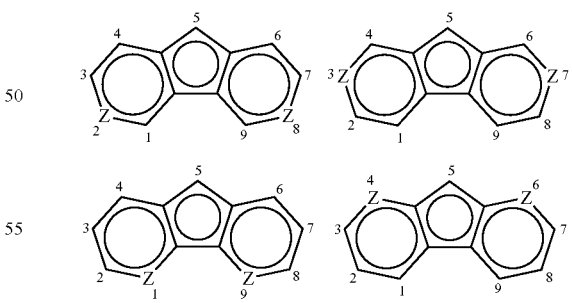

A "ring heteroatom" is a heteroatom that is within a cyclic ring structure. A "heteroatom substituent" is heteroatom containing group that is directly bonded to a ring structure through the heteroatom. A "bridging heteroatom substituent" is a heteroatom or heteroatom group that is directly bonded to two different ring structures through the heteroatom. The terms "ring heteroatom", "heteroatom substituent", and "bridging heteroatom substituent" are illustrated below where Z and R' are as defined above. It should be noted that a "heteroatom substituent" can be a "bridging heteroatom substituent" when R' is additionally defined as the ligand "A".

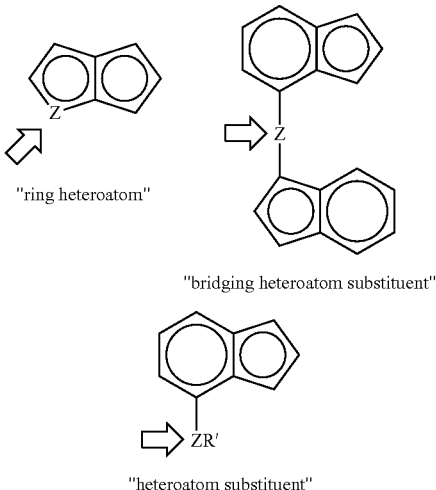

"ring heteroatom"

"bridging heteroatom substituent"

"heteroatom substituent"

A "ring carbon atom" is a carbon atom that is part of a cyclic ring structure. By this definition, an indenyl ligand has nine ring carbon atoms; a cyclopentadienyl ligand has five ring carbon atoms.

Transition metal compounds have symmetry elements and belong to symmetry groups. These elements and groups are well established and can be referenced from Chemical Applications of Group Theory (2nd Edition) by F. Albert Cotton, Wiley-Interscience, 1971. Compounds with $C_s$ symmetry possess a mirror plane. For example, the structure below has a $C_s$ symmetric plane that bisects the zirconium center, the carbon bridge and the cyclopentadienyl and fluorenyl ligands.

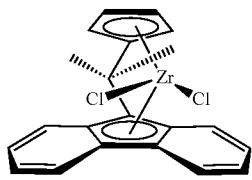

Compounds with pseudo-$C_s$ symmetry are similar with the exception that the bridging group, the labile ligands, and distant substituents of similar size on the cyclopentadienyl ligand or fluorenyl ligand are not included in determining the symmetry of the compound. These compounds, while not truly $C_s$-symmetric, are considered to have $C_s$-symmetric active sites for olefin polymerization or oligomerization. Therefore, a compound, for example having a MeEtSi or MePhSi bridging ligand, is considered to have a pseudo $C_s$-plane of symmetry given the appropriate remaining ligand structure. Likewise, a compound, for example having one Me and one Cl labile ligand, is considered to have a pseudo $C_s$-plane of symmetry given the appropriate remaining ligand structure. Non-limiting examples of pseudo $C_s$ symmetric compounds are illustrated below:

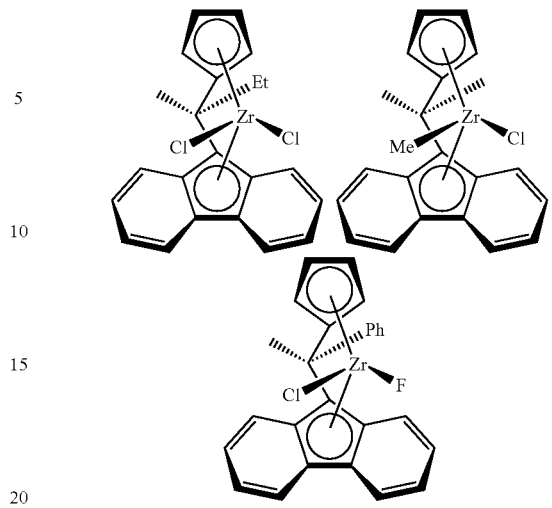

Compounds with pseudo-$C_s$ symmetry can also have unlike substituents on the non-labile ligands (i.e. cyclopentadienyl or fluorenyl ligands) if the substituents are distant from the active site. Substituents of this type, referred to as pseudo symmetric substituents, are typically adjacent to the bridging group and do not substantially differ in size from one another. Typically the size difference of these substituents is within 2 non-hydrogen atoms of each other. Thus a cyclopentadienyl substituted at the 2 and the 5 positions with methyl and ethyl, respectively, or a fluorenyl substituted at the 1 and the 8 positions with hexyl and octyl, respectively, would be considered to have pseudo-$C_s$ symmetry.

In general, those catalysts both capable of producing syndiotactic polypropylene and capable of reacting with hydrogen to terminate the growing polymer or oligomer chain, are catalysts that are useful in this invention.

In an embodiment of the invention, catalysts capable of making the inventive PAO structure(s) comprise metallocene compounds (pre-catalysts) represented by formula (1) having $C_s$ or pseudo-$C_s$ symmetry:

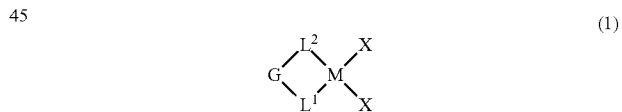

(1)

wherein:

M is the metal center, and is a group 4 metal preferably titanium, zirconium or hafnium, most preferably zirconium or hafnium;

$L^1$ is a unsubstituted fluorenyl, heterocyclopentapentalenyl, or heterofluorenyl, or a substituted fluorenyl, heterocyclopentapentalenyl, or heterofluorenyl ligand with pseudo symmetric substituents, each substituent group being, independently, a radical group which is a hydrocarbyl, substituted hydrocarbyl, halocarbyl, substituted halocarbyl, silylcarbyl or germylcarbyl, and optionally two or more adjacent substituents may join to form a substituted or unsubstituted, saturated, partially unsaturated or aromatic, cyclic or polycyclic substituent;

$L^2$ is a cyclopentadienyl ring or a substituted cyclopentadienyl ring with pseudo symmetric substituents in the 2 and 5 positions of the ring, each substituent group being, independently, a radical group which is a hydrocarbyl, substituted hydrocarbyl, halocarbyl, substituted halocarbyl, silylcarbyl or germylcarbyl;

G is a bridging group;

X are independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; both X may, independently, be a halogen, alkoxide, aryloxide, amide, phosphide or other univalent anionic ligand or both X can also be joined to form a anionic chelating ligand.

In formula (1), $L^1$ is preferably fluorenyl or substituted fluorenyl, more preferably fluorenyl, 2,7-dimethylfluorenyl, 2,7-diethylfluorenyl, 2,7-dipropylfluorenyl, 2,7-dibutylfluorenyl, 2,7-diphenylfluorenyl, 2,7-dichlorofluorenyl, 2,7-dibromofluorenyl, 3,6-dimethylfluorenyl, 3,6-diethylfluorenyl, 3,6-dipropylfluorenyl, 3,6-dibutylfluorenyl, 3,6-diphenylfluorenyl, 3,6-dichlorofluorenyl, 3,6-dibromofluorenyl or 1,1,4,4,7,7,10,10-octamethyl-octahydrodibenzofluorenyl, more preferably fluorenyl, 2,7-dimethylfluorenyl, 2,7-diethylfluorenyl, 2,7-dipropylfluorenyl, 2,7-dibutylfluorenyl, 3,6-dimethylfluorenyl, 3,6-diethylfluorenyl, 3,6-dipropylfluorenyl, 3,6-dibutylfluorenyl, or 1,1,4,4,7,7,10,10-octamethyl-octahydrodibenzofluorenyl, most preferably 2,7-di-tert-butylfluorenyl or fluorenyl; $L^2$ is preferably cyclopentadienyl; G is preferably methylene, dimethylmethylene, diphenylmethylene, dimethylsilylene, diphenylsilylene, di(4-triethylsilylphenyl)silylene, ethylene, more preferably diphenylmethylene, diphenylsilylene, dimethylsilylene and ethylene; and most preferably diphenylmethylene; X is preferably hydrocarbyl or halo, more preferably methyl, benzyl, fluoro or chloro, most preferably methyl or chloro; M is preferably zirconium or hafnium, most preferably zirconium.

In a preferred embodiment of the invention, a subset of the metallocene compounds (pre-catalysts) represented by formula (1) having $C_s$ or pseudo-$C_s$ symmetry are represented by formula (1a):

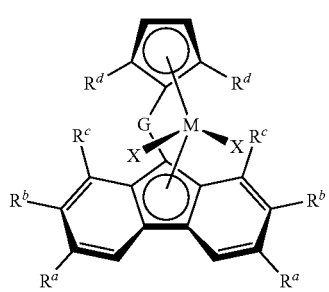

wherein M, G and X are defined as in formula (1);

each $R^a$ and $R^b$ are selected from hydrogen, halogen, hydrocarbyl, substituted hydrocarbyl, halocarbyl, substituted halocarbyl, silylcarbyl, germylcarbyl or polar radicals, and optionally two or more adjacent substituents may join to form a substituted or unsubstituted, saturated, partially unsaturated or aromatic, cyclic or polycyclic substituent, with the proviso that each $R^a$ is the same and each $R^b$ is the same and allow the compound to be $C_s$-symmetric or pseudo $C_s$-symmetric;

each $R^c$ is a pseudo symmetric substituent with respect to the other and is selected from hydrogen or a hydrocarbyl, substituted hydrocarbyl, halocarbyl, substituted halocarbyl, silylcarbyl or germylcarbyl radicals;

each $R^d$ is a pseudo symmetric substituent with respect to the other and is selected from hydrogen or a hydrocarbyl, substituted hydrocarbyl, halocarbyl, substituted halocarbyl, silylcarbyl or germylcarbyl radicals.

In some embodiments of the invention of formula (1a), each $R^d$, $R^a$ and $R^c$ are preferably hydrogen; and each $R^b$ is preferably a hydrogen, hydrocarbyl, halogen, silylcarbyl, or polar radical; more preferably, hydrogen, methyl, ethyl, propyl, butyl, phenyl, mesityl, fluoro, chloro, bromo, dimethylamido, diethylamido or methoxy; even more preferably hydrogen or butyl; still more preferably hydrogen or tert-butyl; and most preferably hydrogen.

In other embodiments of the invention of formula (1a), each $R^d$, $R^b$ and $R^c$ are preferably hydrogen, and each $R^a$ is preferably a hydrogen, hydrocarbyl, halogen, or silylcarbyl; more preferably, hydrogen, methyl, ethyl, propyl, butyl, fluoro, chloro, or bromo; even more preferably hydrogen or butyl; still more preferably hydrogen or tert-butyl; and most preferably hydrogen.

Still, in other embodiments of the invention of formula (1a), each $R^d$ and $R^c$ are preferably hydrogen, and each $R^a$ and $R^b$ are joined together to form a fused partially saturated six-membered carbon ring, each such fused ring preferably substituted with four methyl substituents. Such preferred ligand structure is illustrated in formula (1b):

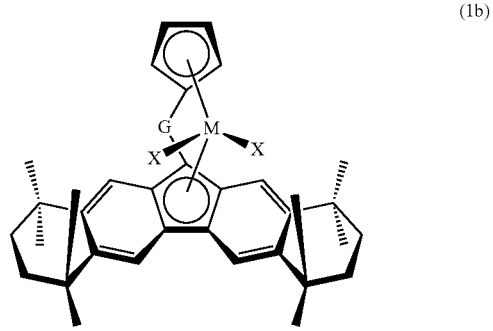

Still in other embodiments of the invention of formula (1a) $R^c$ and $R^d$ are preferably hydrogen; each $R^a$ and $R^b$ are chosen from hydrogen, bromine, chlorine, methyl, ethyl, propyl, butyl or phenyl, more preferably $R^a$ is hydrogen and $R^b$ is chosen from hydrogen, methyl, ethyl, propyl, or butyl, or $R^b$ is hydrogen and $R^a$ is chosen from hydrogen, methyl, ethyl, propyl, or butyl, even more preferably $R^a$ is hydrogen and $R^b$ is tert-butyl or hydrogen; G is preferably methylene, dimethylmethylene, diphenylmethylene, dimethylsilylene, diphenylsilylene, di(4-triethylsilylphenyl)silylene, ethylene, more preferably diphenylmethylene, diphenylsilylene, and dimethylsilylene; and most preferably diphenylmethylene; X is preferably hydrocarbyl or halo, more preferably methyl, benzyl, floro or chloro, most preferably methyl or chloro; M is preferably zirconium or hafnium, most preferably zirconium.

Preferred but non-limiting examples of pre-catalysts represented by formula (1) include: diphenylmethylene(cyclopentadienyl)(9-fluorenyl)zirconium dichloride, methylene (cyclopentadienyl)(9-fluorenyl)zirconium dichloride, dimethylmethylene(cyclopentadienyl)(9-fluorenyl)zirconium dichloride, dimethylsilylene(cyclopentadienyl)(9-fluorenyl)zirconium dichloride, diphenylsilylene(cyclopentadienyl)(9-fluorenyl)zirconium dichloride, ethylene(cyclopentadienyl)(9-fluorenyl)zirconium dichloride, diphenylmethylene(cyclopentadienyl)(9-fluorenyl)zirconium dimethyl, methylene(cyclopentadienyl)(9-fluorenyl)zirconium dimethyl, dimethylmethylene(cyclopentadienyl)(9-fluorenyl)zirconium dimethyl, dimethylsilylene(cyclopentadienyl)(9-fluorenyl)zirconium dimethyl, diphenylsilylene(cyclopentadienyl)(9-fluorenyl)zirconium dimethyl, and ethylene(cyclopentadienyl)(9-fluorenyl)zirconium dichloride. The most preferred pre-catalysts represented by formula (1) are diphenylmethylene(cyclopentadienyl)(9-fluorenyl)zirconium dichloride and diphenylmethylene(cyclopentadienyl)(9-fluorenyl)zirconium dimethyl.

In another embodiment of the invention, catalysts capable of making the inventive PAO structure(s) comprise metallocene compounds (pre-catalysts) represented by formula (2) having $C_s$ or pseudo-$C_s$ symmetry:

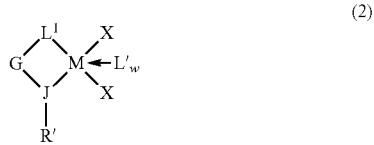

(2)

wherein:
M is the metal center, and is a group 4 metal preferably titanium, zirconium or hafnium, most preferably zirconium or hafnium, most preferably titanium;
$L^1$ is a unsubstituted fluorenyl, heterocyclopentapentalenyl, or heterofluorenyl, or a substituted fluorenyl, heterocyclopentapentalenyl, or heterofluorenyl ligand with pseudo symmetric substituents, each substituent group being, independently, a radical group which is a hydrocarbyl, substituted hydrocarbyl, halocarbyl, substituted halocarbyl, silylcarbyl or germylcarbyl, and optionally two or more adjacent substituents may join to form a substituted or unsubstituted, saturated, partially unsaturated or aromatic, cyclic or polycyclic substituent;
G is a bridging group;
J is a heteroatom from group 15, preferably N or P, most preferably N;
R' is a radical group which is a hydrocarbyl, substituted hydrocarbyl, halocarbyl, or substituted halocarbyl;
L' is a neutral Lewis base and w represents the number of L' bonded to M where w is 0, 1, or 2, and optionally any L' and any X may be bonded to one another.
X are independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; both X may, independently, be a halogen, alkoxide, aryloxide, amide, phosphide or other univalent anionic ligand or both X can also be joined to form a anionic chelating ligand.

In formula (2), $L^1$ is preferably fluorenyl or substituted fluorenyl, more preferably fluorenyl, 2,7-dimethylfluorenyl, 2,7-diethylfluorenyl, 2,7-dipropylfluorenyl, 2,7-dibutylfluorenyl, 2,7-diphenylfluorenyl, 2,7-dichlorofluorenyl, 2,7-dibromofluorenyl, 3,6-dimethylfluorenyl, 3,6-diethylfluorenyl, 3,6-dipropylfluorenyl, 3,6-dibutylfluorenyl, 3,6-diphenylfluorenyl, 3,6-dichlorofluorenyl, 3,6-dibromofluorenyl or 1,1,4,4,7,7,10,10-octamethyl-octahydrodibenzofluorenyl, more preferably fluorenyl, 2,7-dimethylfluorenyl, 2,7-diethylfluorenyl, 2,7-dipropylfluorenyl, 2,7-dibutylfluorenyl, 3,6-dimethylfluorenyl, 3,6-diethylfluorenyl, 3,6-dipropylfluorenyl, 3,6-dibutylfluorenyl, or 1,1,4,4,7,7,10,10-octamethyl-octahydrodibenzofluorenyl, most preferably 2,7-di-tert-butylfluorenyl, 3,6-di-tert-butylfluorenyl, 1,1,4,4,7,7,10,10-octamethyl-octahydrodibenzofluorenyl, or fluorenyl; G is preferably methylene, dimethylmethylene, diphenylmethylene, dimethylsilylene, methylphenylsilylene, diphenylsilylene, di(4-triethylsilylphenyl)silylene, ethylene, more preferably diphenylmethylene, diphenylsilylene, methylphenylsilylene, and dimethylsilylene; and most preferably dimethylsilylene; J is preferably nitrogen, R' is preferably hydrocarbyl or halocarbyl, more preferably $C_3$-$C_{20}$ hydrocarbyl, even more preferably all isomers (including cyclics and polycyclics) of propyl, butyl, pentyl, hexyl, heptyl, octyl, nonyl, decyl, undecyl, dodecyl, benzyl, phenyl and substituted phenyl, still more preferably tert-butyl, neopentyl, benzyl, phenyl, diisopropylphenyl, adamantyl, norbornyl, cyclohexyl, cyclooctyl, cyclodecyl, and cyclododecyl, and most preferably, tert-butyl, adamant-1-yl, norborn-2-yl, cyclohexyl, cyclooctyl, and cyclododecyl; X is preferably hydrocarbyl or halo, more preferably methyl, benzyl, floro or chloro, most preferably methyl or chloro; w is preferably zero (L' being absent); M is preferably titanium, zirconium or hafnium, most preferably titanium.

Preferred but non-limiting examples of pre-catalysts represented by formula (2) include: methylene(9-fluorenyl)(tert-butylamido)titanium dichloride, dimethylmethylene(9-fluorenyl)(tert-butylamido)titanium dichloride, diphenylmethylene(9-fluorenyl)(tert-butylamido)titanium dichloride, dimethylsilylene(9-fluorenyl)(tert-butylamido)titanium dichloride, diphenylsilylene(9-fluorenyl)(tert-butylamido)titanium dichloride, methylphenylsilylene(9-fluorenyl)(tert-butylamido)titanium dichloride, methylene(9-fluorenyl)(tert-butylamido)titanium dimethyl, dimethylmethylene(9-fluorenyl)(tert-butylamido)titanium dimethyl, diphenylmethylene(9-fluorenyl)(tert-butylamido)titanium dimethyl, dimethylsilylene(9-fluorenyl)(tert-butylamido)titanium dimethyl, diphenylsilylene(9-fluorenyl)(tert-butylamido)titanium dimethyl, methylphenylsilylene(9-fluorenyl)(tert-butylamido)titanium dichloride, methylene(9-fluorenyl)(benzylamido)titanium dichloride, dimethylmethylene(9-fluorenyl)(benzylamido)titanium dichloride, diphenylmethylene(9-fluorenyl)(benzylamido)titanium dichloride, dimethylsilylene(9-fluorenyl)(benzylamido)titanium dichloride, diphenylsilylene(9-fluorenyl)(benzylamido)titanium dichloride, methylphenylsilylene(9-fluorenyl)(benzylamido)titanium dichloride, methylene(9-fluorenyl)(benzylamido) titanium dimethyl, dimethylmethylene(9-fluorenyl)(benzylamido)titanium dimethyl, diphenylmethylene(9-fluorenyl)(benzylamido)titanium dimethyl, dimethylsilylene(9-fluorenyl)(benzylamido)titanium dimethyl, diphenylsilylene(9-fluorenyl)(benzylamido)titanium dimethyl, methylphenylsilylene(9-fluorenyl)(benzylamido)titanium dichloride, methylene(9-fluorenyl)(adamant-1-ylamido)titanium dichloride, dimethylmethylene(9-fluorenyl)(adamant-1-ylamido)titanium dichloride, diphenylmethylene(9-fluorenyl)(adamant-1-ylamido)titanium dichloride, dimethylsilylene(9-fluorenyl)(adamant-1-ylamido)titanium dichloride, diphenylsilylene(9-fluorenyl)(adamant-1-ylamido)titanium dichloride, methylphenylsilylene(9-fluorenyl)(adamant-1-ylamido)titanium dichloride, methylene(9-fluorenyl)(adamant-1-ylamido)titanium dimethyl, dimethylmethylene(9-fluorenyl)(adamant-1-ylamido)titanium dimethyl, diphenylmethylene(9-fluorenyl)(adamant-1-ylamido)titanium dimethyl, dimethylsilylene(9-fluorenyl)(adamant-1-ylamido)titanium dimethyl, diphenylsilylene(9-fluorenyl)(adamant-1-ylamido)titanium dimethyl, methylphenylsilylene(9-fluorenyl)(adamant-1-ylamido)titanium dichloride, methylene(9-fluorenyl)(cyclododecylamido)titanium dichloride, dimethylmethylene(9-fluorenyl)(cyclododecylamido)titanium dichloride, diphenylmethylene(9-fluorenyl)(cyclododecylamido)titanium dichloride, dimethylsilylene(9-fluorenyl)(cyclododecylamido)titanium dichloride, diphenylsilylene(9-fluorenyl)(cyclododecylamido)titanium dichloride, methylphenylsilylene(9-fluorenyl)(cyclododecylamido)titanium dichloride, methylene(9-fluorenyl)(cyclododecylamido)titanium dimethyl, dimethylmethylene(9-fluorenyl)(cyclododecylamido)titanium dimethyl, diphenylmethylene(9-fluorenyl)(cyclododecylamido)titanium dimethyl, dimethylsilylene(9-fluorenyl)(cyclododecylamido)titanium dimethyl, diphenylsilylene(9-fluorenyl)(cyclododecylamido)titanium dimethyl, and methylphenylsilylene(9-fluorenyl)(cyclododecylamido)titanium dichloride.

In still another embodiment of the invention, catalysts capable of making the inventive PAO structure(s) comprise metallocene compounds (pre-catalysts) represented by formula (3) having $C_s$ or pseudo-$C_s$ symmetry:

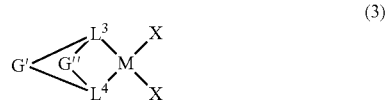

(3)

wherein:
M is the metal center, and is a group 4 metal preferably titanium, zirconium or hafnium, most preferably zirconium or hafnium;
$L^3$ is a cyclopentadienyl ring optionally substituted in the 4 position of the ring, the substituent group being chosen from a radical group which is a hydrocarbyl, substituted hydrocarbyl, halocarbyl, substituted halocarbyl, silylcarbyl or germylcarbyl;
$L^4$ is a substituted cyclopentadienyl ring with pseudo symmetric substituents in the 3 and 5 positions of the ring, each substituent group being, independently, a radical group which is a hydrocarbyl, substituted hydrocarbyl, halocarbyl, substituted halocarbyl, silylcarbyl or germylcarbyl;
G' and G" are bridging groups;
X are independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; both X may, independently, be a halogen, alkoxide, aryloxide, amide, phosphide or other univalent anionic ligand or both X can also be joined to form a anionic chelating ligand.

In formula (3), $L^3$ is preferably cyclopentadienyl, or hydrocarbyl or silylcarbyl substituted cyclopentadienyl with the substitution on the 4-position of the cyclopentadienyl ring, more preferably cyclopentadienyl, 4-methylcyclopentadienyl, 4-ethylcyclopentadienyl, 4-propylcyclopentadienyl, 4-butylcyclopentadienyl, 4-pentylcyclopentadienyl, 4-hexylcyclopentadienyl, 4-heptylcyclopentadienyl, 3-octylcyclopentadienyl, or 4-trimethylsilylcyclopentadieyl, even more preferably cyclopentadienyl, 4-isopropylcyclopentadienyl, 4-tert-butylcyclopentadienyl, 4-(2,2-dimethylpent-3-yl)cyclopentadienyl, 4-(2,2-dimethylbut-3-yl)cyclopentadienyl or 4-trimethylsilylcyclopentadienyl, and most preferably cyclopentadienyl, 4-isopropylcyclopentadienyl, or 4-trimethylsilylcyclopentadienyl; $L^4$ is preferably hydrocarbyl or silylcarbyl substituted cyclopentadienyl with the substitutions on the 3- and 5-positions of the cyclopentadienyl ring, more preferably 3,5-dimethylcyclopentadienyl, 3,5-diethylcyclopentadienyl, 3,5-dipropylcyclopentadienyl, 3,5-dibutylcyclopentadienyl, 3,5-dipentylcyclopentadienyl, 3,5-dihexylcyclopentadienyl, 3,5-dibenzylcyclopentadienyl, or 3,5-bis(trimethylsilyl)cyclopentadieyl, even more preferably 3,5-dimethylcyclopentadienyl, 3,5-diisopropylcyclopentadienyl, 3,5-di-tert-butylcyclopentadienyl, 3,5-dicyclopentylcyclopentadienyl, 3,5-dipent-3-ylcyclopentadienyl, 3,5-dicyclohexylcyclopentadienyl, 3,5-dibenzylcyclopentadienyl, or 3,5-bis(trimethylsilyl)cyclopentadienyl, and most preferably 3,5-dimethylcyclopentadienyl, 3,5-diisopropylcyclopentadienyl, 3,5-di-tert-butylcyclopentadienyl, 3,5-dibenzylcyclopentadienyl, or 3,5-bis(trimethylsilyl)cyclopentadieyl; each G' and G" are preferably methylene, dimethylmethylene, dimethylsilylene, more preferably dimethylmethylene, and dimethylsilylene; and most preferably dimethylsilylene; X is preferably hydrocarbyl or halo, more preferably methyl, benzyl, floro or chloro, most preferably methyl or chloro; M is preferably zirconium or hafnium, most preferably zirconium.

In a preferred embodiment of the invention, a subset of the metallocene compounds (pre-catalysts) represented by formula (3) having $C_s$ or pseudo-$C_s$ symmetry are represented by formula (3a):

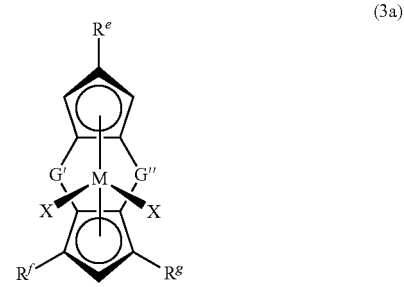

(3a)

wherein M, G', G", and X are defined as in formula (3);
$R^e$ is selected from hydrogen or a hydrocarbyl, substituted hydrocarbyl, halocarbyl, substituted halocarbyl, silylcarbyl or germylcarbyl radicals;
each $R^f$ and $R^g$ are selected from hydrocarbyl, substituted hydrocarbyl, halocarbyl, substituted halocarbyl, silylcarbyl, or germylcarbyl, with the proviso that each $R^f$ and $R^g$ are chosen to allow the compound to be $C_s$-symmetric or pseudo $C_s$-symmetric.

In some embodiments of the invention of formula (3a), each $R^f$ and $R^g$ are preferably hydrocarbyl or silylcarbyl, more preferably, methyl, ethyl, propyl, butyl, pentyl, hexyl, benzyl, or trimethylsilyl, more preferably, methyl, isopropyl, tert-butyl, cyclopentyl, pent-3-yl, cyclohexyl, benzyl, or trimethylsilyl, and most preferably methyl, isopropyl, tert-butyl, benzyl or trimethylsilyl; and $R^e$ is preferably hydrogen, hydrocarbyl or silylcarbyl, more preferably, methyl, ethyl, propyl, butyl, pentyl, hexyl, heptyl, octyl, or trimethylsilyl; even more preferably, hydrogen, isopropyl, tert-butyl, 2,2-dimethylpent-3-yl, 2,2-dimethylbut-3-yl, or trimethylsilyl, and most preferably, hydrogen, isopropyl or trimethylsilyl.

In formulas 1, 1a, 1b, 2, 3 or 3a, G, G' and G" are selected from $R*_2C$, $R*_2Si$, $R*_2Ge$, $R*_2CCR*_2$, $R*C=CR*$, $R*_2CSiR*_2$, $R*_2SiSiR*_2$, $R*B$, $R*_2C-BR*$, $R*N$, $R*P$, O, S, and Se where each $R*$ is independently selected from hydrogen, $C_1$-$C_{20}$ containing hydrocarbyl, substituted hydrocarbyl, halocarbyl, substituted halocarbyl, silylcarbyl or germylcarbyl substituent and optionally two or more adjacent $R*$ may join to form a substituted or unsubstituted, saturated, partially unsaturated, cyclic or polycyclic substituent. Preferably, G, G' and G" are selected from $R*_2C$, $R*_2Si$, $R*_2Ge$, $R*_2CCR*_2$, $R*B$, $R*N$, $R*P$, O, S, and Se where each $R*$ is as defined above. Most preferably, G, G' and G" are selected from $R*_2C$, $R*_2Si$, and $R*_2CCR*_2$.

In still another embodiment of the invention, catalysts capable of making the inventive PAO structure(s) comprise metallocene compounds (pre-catalysts) represented by formula (4) having $C_2$ symmetry:

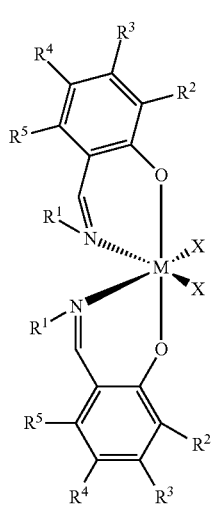

(4)

wherein:
M is the metal center, and is a group 4 metal preferably titanium, zirconium or hafnium, most preferably zirconium or hafnium, most preferably titanium;
O is oxygen;
N is nitrogen;
$R^1$ is a radical group which is a hydrocarbyl, substituted hydrocarbyl, halocarbyl, substituted halocarbyl, silylcarbyl or germylcarbyl, most preferably $R^1$ is halocarbyl;
$R^2$ is a radical group which is a hydrocarbyl, substituted hydrocarbyl, halocarbyl, substituted halocarbyl, silylcarbyl or germylcarbyl, most preferably $R^2$ is hydrocarbyl having three or more carbon atoms or silylcarbyl having three or more carbon atoms;
$R^3$, $R^4$ and $R^5$ are independently hydrogen or a radical group which is a hydrocarbyl, substituted hydrocarbyl, halocarbyl, substituted halocarbyl, silylcarbyl or germylcarbyl, most preferably $R^3$, $R^4$ and $R^5$ are hydrogen;
X are independently, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both X are joined and bound to the metal atom to form a metallacycle ring containing from about 3 to about 20 carbon atoms; or both together can be an olefin, diolefin or aryne ligand; both X may, independently, be a halogen, alkoxide, aryloxide, amide, phosphide or other univalent anionic ligand or both X can also be joined to form a anionic chelating ligand.

In some embodiments of the invention of formula (4), $R^1$ is preferably hydrocarbyl or halocarbyl radicals, more preferably, methyl, ethyl, propyl, butyl, pentyl, hexyl, benzyl, phenyl, methylphenyl, dimethylphenyl, ethylphenyl, diethylphenyl, propylphenyl, dipropylphenyl, perfluorophenyl, trifluorphenyl, difluorophenyl, or fluorophenyl, more preferably, phenyl, 2-methylphenyl, 2,6-dimethylphenyl, 2-isopropylphenyl, perfluorophenyl, 2,4,6-trifluorophenyl, 2,6-difluorophenyl, 3,5-difluorophenyl or 4-fluorophenyl, and most preferably perfluorophenyl; $R^2$ is preferably hydrocarbyl or silylcarbyl radicals, more preferably $C_3$-$C_{12}$ hydrocarbyl or $C_3$-$C_{12}$ silylcarbyl, even more preferably, propyl, butyl, pentyl, hexyl, heptyl, octyl, cumyl, or trimethylsilyl, still even more preferably, isopropyl, tert-butyl, cumyl, or trimethylsilyl, and most preferably, tert-butyl or trimethylsilyl; $R^3$, $R^4$ and $R^5$ are preferably hydrogen or hydrocarbyl radicals, most preferably hydrogen; X is preferably hydrocarbyl or halo, more preferably methyl, benzyl, floro or chloro, most preferably methyl or chloro; M is preferably titanium, zirconium or hafnium, most preferably titanium.

Preferred metallocene compounds (pre-catalysts) which, according to the present disclosure, provide catalyst systems which are specific to the production of poly-olefins typically having greater than 6% mr triads.

Activators and Catalyst Activation

The catalyst precursors, when activated by a commonly known activator form active catalysts for the polymerization or oligomerization of olefins. Lewis acid activators include triphenylboron, tris-perfluorophenylboron, tris-perfluorophenylaluminum and the like, but exclude the class of activators referred to as alumoxanes. Ionic activators include dimethylanilinium tetrakisperfluorophenylborate, triphenylcarbonium tetrakisperfluorophenylborate, dimethylanilinium tetrakisperfluorophenylaluminate, and the like. Collectively, Lewis acid activators and ionic activators are referred to as discrete activators since they can be readily characterized, whereas alumoxanes are not well characterized. Likewise, Lewis acid activators and ionic activators are referred to as stoichiometric activators since relatively low molar ratios of activator to transition metal compound are needed as compared to alumoxanes activators that require large excesses.

A co-activator is a compound capable of alkylating the transition metal complex, such that when used in combination with a discrete activator, an active catalyst is formed. Co-activators include alumoxanes such as methylalumoxane, modified alumoxanes such as modified methylalumoxane, and aluminum alkyls such trimethylaluminum, tri-isobutylaluminum, triethylaluminum, and tri-isopropylaluminum, tri-n-hexylaluminum, tri-n-octylaluminum, tri-n-decylaluminum or tri-n-dodecylaluminum. Co-activators are typically used in combination with Lewis acid activators and ionic activators when the pre-catalyst is not a dihydrocarbyl or dihydride complex. Sometimes co-activators are also used as scavengers to deactivate impurities in feed or reactors. Sometimes co-activators are also used as chain transfer or chain shuttling agents.

Particularly preferred co-activators include alkylaluminum compounds represented by the formula: $R_3Al$, where each R is, independently, a $C_1$ to $C_{18}$ alkyl group, preferably each R is, independently, selected from the group consisting of methyl, ethyl, n-propyl, iso-propyl, iso-butyl, n-butyl, t-butyl, n-pentyl, iso-pentyl, neopentyl, n-hexyl, iso-hexyl, n-heptyl, iso-heptyl, n-octyl, iso-octyl, n-nonyl, n-decyl, n-undecyl, n-dodecyl, n-tridecyl, n-tetradecyl, n-pentadecy, n-hexadecyl, n-heptadecyl, n-octadecyl, and their iso-analogs.

In the process, hydrogen is a useful chain transfer agent in the reaction. In a preferred embodiment, alternative chain transfer agents (CTA's) can be used in the processes described herein, reducing the need for hydrogen wherein hydrogen is absent or used in limited amounts. Preferred alternative chain transfer agents include diethylzinc, and trialkylaluminums such as triisobutylaluminum, tri-n-octylaluminum, triethylaluminum and the like, or mixtures thereof. Alternative CTA's are often used at transition metal compound to CTA molar ratios of from about 1:1 to 1:100, preferably from about 1:4 to 1:50, more preferably from about 1:10 to about 1:33. The molar ratio of alternative CTA to transition metal compound is preferably less than 100:1 more preferably less than 50:1, and most preferably less than 35:1.

It is within the scope of this invention to use neutral or ionic activators such as tri(n-butyl)ammonium tetrakis(pentafluorophenyl)borate, trisperfluorophenylboron, trisperfluoronaphthylboron, polyhalogenated heteroborane anions (WO 98/43983), boric acid (U.S. Pat. No. 5,942,459) or combinations thereof.

Stoichiometric activators (at times used in combination with a co-activator) may be used in the practice of this invention. Preferably, discrete ionic activators such as [Me$_2$PhNH][B(C$_6$F$_5$)$_4$], [Ph$_3$C][B(C$_6$F$_5$)$_4$], [Me$_2$PhNH][B(C$_6$H$_3$-3,5-(CF$_3$)$_2$)$_4$], [Ph$_3$C][B(C$_6$H$_3$-3,5-(CF$_3$)$_2$)$_4$], [NH$_4$][B(C$_6$H$_5$)$_4$] or Lewis acidic activators such as B(C$_6$F$_5$)$_3$ or B(C$_6$H$_5$)$_3$ can be used, where Ph is phenyl and Me is methyl.

Examples of neutral stoichiometric activators include trisubstituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared by reacting a transition metal compound with an activator, such as B(C$_6$F$_6$)$_3$, which upon reaction with the hydrolyzable ligand (X') of the transition metal compound forms an anion, such as ([B(C$_6$F$_5$)$_3$(X')]$^-$), which stabilizes the cationic transition metal species generated by the reaction. The catalysts can be, and preferably are, prepared with activator components which are ionic compounds or compositions. However preparation of activators utilizing neutral compounds is also contemplated by this invention.

Compounds useful as an activator component in the preparation of the ionic catalyst systems used in the process of this invention comprise a cation, which is preferably a Brønsted acid capable of donating a proton, and a compatible non-coordinating anion which anion is relatively large (bulky), capable of stabilizing the active catalyst species which is formed when the two compounds are combined and said anion will be sufficiently labile to be displaced by olefinic diolefinic and acetylenically unsaturated substrates or other neutral Lewis bases such as ethers, nitriles and the like. Two classes of compatible non-coordinating anions have been disclosed in EPA 277,003 and EPA 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In a preferred embodiment, the ionic stoichiometric activators include a cation and an anion component, and may be represented by the following formula: $(L^{}-H)_d^+(A^{d-})$ wherein $L^{}$ is an neutral Lewis base; H is hydrogen; $(L^{**}-H)^+$ is a Brønsted acid, and $A^{d-}$ is a non-coordinating anion having the charge d−, and d is an integer from 1 to 3.

The cation component, $(L^{**}-H)_d^+$ may include Brønsted acids such as protons or protonated Lewis bases or reducible Lewis acids capable of protonating or abstracting a moiety, such as an alkyl or aryl, from the precatalyst after alkylation.

The activating cation $(L^{}-H)_d^+$ may be a Brønsted acid, capable of donating a proton to the alkylated transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether, diethyl ether, tetrahydrofuran and dioxane, sulfoniums from thioethers, such as diethyl thioethers and tetrahydrothiophene, and mixtures thereof. The activating cation $(L^{}-H)_d^+$ may also be a moiety such as silver, tropylium, carbeniums, ferroceniums and mixtures, preferably carboniums and ferroceniums; most preferably triphenyl carbonium. The anion component $A^{d-}$ include those having the formula $[M^{k+}Q_n]^{d-}$ wherein k is an integer from 1 to 3; n is an integer from 2-6; n−k=d; M is an element selected from group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as a non-coordinating anion activator in combination with a co-activator in the preparation of the improved catalysts of this disclosure are tri-substituted ammonium salts such as: trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, and dialkyl ammonium salts such as: di-(iso-propyl)ammonium tetrakis(pentafluorophenyl)borate, and dicyclohexylammonium tetrakis(pentafluorophenyl)borate; and other salts such as tri(o-tolyl)phosphonium tetrakis(pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium)tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, and benzene(diazonium)tetrakis(3,5-bis(trifluoromethyl)phenyl)borate.

Most preferably, the non-coordinating anion activator, $(L**-H)_d^+(A^{d-})$, is N,N-dimethylanilinium tetrakis(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

The catalyst precursors can also be activated with cocatalysts or activators that comprise non-coordinating anions containing metalloid-free cyclopentadienide ions. These are described in U.S. Patent Publication 2002/0058765 A1, published on 16 May 2002, and for the instant disclosure, require the addition of a co-activator to the catalyst pre-cursor. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Preferred non-coordinating anions useful in accordance with this disclosure are those that are compatible, stabilize the transition metal complex cation in the sense of balancing its ionic charge at +1, yet retain sufficient liability to permit displacement by an ethylenically or acetylenically unsaturated monomer during polymerization. These types of cocatalysts are sometimes used with scavengers such as but not limited to tri-iso-butylaluminum, tri-n-octylaluminum, tri-n-hexylaluminum, triethylaluminum or trimethylaluminum.

Disclosure processes also can employ cocatalyst compounds or activator compounds that are initially neutral Lewis acids but form a cationic metal complex and a non-coordinating anion, or a zwitterionic complex upon reaction with the alkylated transition metal compounds. The alkylated metallocene compound is formed from the reaction of the catalyst pre-cursor and the co-activator. For example, tris(pentafluorophenyl)boron or aluminum act to abstract a hydrocarbyl ligand to yield an disclosure cationic transition metal complex and stabilizing non-coordinating anion, see EP-A-0 427 697 and EP-A-0 520 732 for illustrations of analogous group-4 metallocene compounds. Also, see the methods and compounds of EP-A-0 495 375. For formation of zwitterionic complexes using analogous group 4 compounds, see U.S. Pat. Nos. 5,624,878; 5,486,632; and 5,527,929.

Additional neutral Lewis-acids are known in the art and are suitable for abstracting formal anionic ligands. See in particular the review article by E. Y.-X. Chen and T. J. Marks, "Cocatalysts for Metal-Catalyzed Olefin Polymerization: Activators, Activation Processes, and Structure-Activity Relationships", *Chem. Rev.*, 100, 1391-1434 (2000).

When the cations of non-coordinating anion activators are Brønsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation.

When an ionic or neutral stoichiometric activator (such as an NCA) is used, the catalyst-precursor-to-activator molar ratio is from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2. The catalyst-precursor-to-co-activator molar ratio is from 1:500 to 1:1, 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

In some embodiments preferred activators and activator/co-activator combinations include dimethylanilinium tetrakis(pentafluorophenyl)borate or tris(pentafluorophenyl)boron, or mixtures of trialkyl aluminum with dimethylanilinium tetrakis(pentafluorophenyl)borate or tris(pentafluorophenyl) boron. In some embodiments, scavenging compounds are used with stoichiometric activators. Typical aluminum or boron alkyl components useful as scavengers are represented by the general formula $R^xJ'Z'_2$ where J' is aluminum or boron, $R^x$ is as previously defined above, and each Z' is independently $R^x$ or a different univalent anionic ligand such as halogen (Cl, Br, I), alkoxide ($OR^x$) and the like. Most preferred aluminum alkyls include triethylaluminum, diethylaluminum chloride, tri-iso-butylaluminum, tri-n-octylaluminum, tri-n-hexylaluminum, trimethylaluminum and the like. Preferred boron alkyls include triethylboron. Scavenging compounds may also be alumoxanes and modified alumoxanes including methylalumoxane and modified methylalumoxane.

Supported Catalysts

Supported catalysts and or supported catalyst systems may be used to prepare sPAO's. To prepare uniform supported catalysts, the catalyst precursor preferably dissolves in the chosen solvent. The term "uniform supported catalyst" means that the catalyst precursor, the activator, and or the activated catalyst approach uniform distribution upon the support's accessible surface area, including the interior pore surfaces of porous supports. Some embodiments of supported catalysts prefer uniform supported catalysts; other embodiments show no such preference.

Useful supported catalyst systems may be prepared by any method effective to support other coordination catalyst systems, effective meaning that the catalyst so prepared can be used for oligomerizing or polymerizing olefins in a heterogenous process. The catalyst precursor, activator, co-activator (if needed), suitable solvent, and support may be added in any order or simultaneously.

By one method, the activator (with or without co-activator), dissolved in an appropriate solvent such as toluene, may be stirred with the support material for 1 minute to 10 hours to prepare the supported catalyst. The total solution volume (of the catalyst solution, the activator solution or both) may be greater than the pore volume of the support, but some embodiments limit the total solution volume below that needed to form a gel or slurry (90% to 400%, preferably 100-200%, of the pore volume). The mixture is optionally heated from 30-200° C. during this time. The catalyst precursor may be added to this mixture as a solid, if a suitable solvent is employed in the previous step, or as a solution. Alternatively, the mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the supported catalyst is either filtered from the solution and vacuum dried or subjected to evaporation to remove the solvent.

Alternatively, the catalyst precursor and activator (and optional co-activator) may be combined in solvent to form a solution. The support is then added to the solution, and the resulting mixture is stirred for 1 minute to 10 hours. The total activator/catalyst-precursor solution volume may be greater than the pore volume of the support, but some embodiments limit the total solution volume below that needed to form a gel or slurry (90% to 400%, preferably 100-200% of the pore volume). After stirring, the residual solvent is removed under vacuum, typically at ambient temperature and over 10-16 hours; however, greater or lesser times and temperatures may be used.

The catalyst precursor may also be supported absent the activator; in this case, the activator (and co-activator if needed) is added to a the liquid phase of a slurry process. For example, a solution of catalyst precursor may be mixed with a support material for a period of 1 minute to 10 hours. The resulting precatalyst mixture may be filtered from the solution and dried under vacuum or treated with evaporation to remove the solvent. The total catalyst-precursor-solution volume may be greater than the support's pore volume, but some embodiments limit the total solution volume below that needed to form a gel or slurry (90% to 400%, preferably 100-200% of the pore volume).

Additionally, two or more different catalyst precursors may be placed on the same support using any of the support methods disclosed above. Likewise, two or more activators or an activator and a co-activator, may be placed on the same support.

Suitable solid particle supports are typically comprised of polymeric or refractory oxide materials, each being preferably porous. Any support material that has an average particle size greater than 10 μm is suitable for use in this disclosure. Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as an activator component. But additional activator may also be used. In some cases, a special family of solid support commonly known as MCM-41 can also be used. MCM-41 is a new class of unique crystalline support and can be prepared with tunable pore size and tunable acidity when modified with a second component. A detailed description of this class of materials and their modification can be found in U.S. Pat. No. 5,264,203.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the disclosure, see for example the descriptions in WO 95/15815 and U.S. Pat. No. 5,427,991. The methods disclosed may be used with the catalyst compounds, activators or catalyst systems of this disclosure to adsorb or absorb them on the polymeric supports, particularly if made up of porous particles, or may be chemically bound through functional groups bound to or in the polymer chains.

Useful catalyst carriers typically have a surface area of from 10-700 $m^2/g$, and or a pore volume of 0.1-4.0 cc/g and or an average particle size of 10-500 μm. Some embodiments select a surface area of 50-500 $m^2/g$, and or a pore volume of 0.5-3.5 cc/g, and or an average particle size of 20-200 μm. Other embodiments select a surface area of 100-400 $m^2/g$, and or a pore volume of 0.8-3.0 cc/g, and or an average particle size of 30-100 μm. Useful carriers typically have a pore size of 10-1000 Ångströms, alternatively 50-500 Ångströms, or 75-350 Ångströms.

The precatalyst and or the precatalyst/activator combinations are generally deposited on the support at a loading level of 10-100 micromoles of catalyst precursor per gram of solid support; alternatively 20-80 micromoles of catalyst precursor per gram of solid support; or 40-60 micromoles of catalyst precursor per gram of support. But greater or lesser values may be used provided that the total amount of solid catalyst precursor does not exceed the support's pore volume.

The precatalyst and or the precatalyst/activator combinations can be supported for gas-phase, bulk, or slurry polymerization, or otherwise as needed. Numerous support methods are known for catalysts in the olefin polymerization art, particularly alumoxane-activated catalysts; all are suitable for use herein. See, for example, U.S. Pat. Nos. 5,057,475 and 5,227,440. An example of supported ionic catalysts appears in WO 94/03056. U.S. Pat. No. 5,643,847 and WO 96/04319A which describe a particularly effective method. Both polymers and inorganic oxides may serve as supports, see U.S. Pat. Nos. 5,422,325, 5,427,991, 5,498,582 and 5,466,649, and international publications WO 93/11172 and WO 94/07928.

In another preferred embodiment, the precatalyst and or activator (with or without a support) are combined with an alkylaluminum compound, preferably a trialkylaluminum compound, prior to entering the reactor. Preferably the alkylaluminum compound is represented by the formula: $R_3Al$, where each R is independently a $C_1$ to $C_{20}$ alkyl group; preferably the R groups are independently selected from the group consisting of methyl, ethyl, propyl, isopropyl, butyl, isobutyl, n-butyl, pentyl, isopentyl, n-pentyl, hexyl, isohexyl, n-hexyl, heptyl, octyl, isooctyl, n-octyl, nonyl, isononyl, n-nonyl, decyl, isodecyl, n-decyl, undecyl, isoundecyl, n-undecyl, dodecyl, isododecyl, and n-dodecyl, preferably isobutyl, n-octyl, n-hexyl, and n-dodecyl. Preferably the alkylaluminum compound is selected from tri-isobutyl aluminum, tri n-octyl aluminum, tri-n-hexyl aluminum, and tri-n-dodecyl aluminum.

Monomers

The catalyst compounds described herein are used to polymerize or oligomerize any unsaturated monomer or monomers. Such monomers include $C_2$ to $C_{24}$ olefins, $C_6$ to $C_{24}$ olefins, $C_6$ to $C_{14}$ olefins, or $C_8$ to $C_{12}$ olefins. In some embodiments monomers include linear, branched or cyclic alpha-olefins, such as $C_6$ to $C_{20}$ linear alpha-olefins, $C_6$ to $C_{14}$ linear alpha-olefins, or $C_8$ to $C_{12}$ linear alpha-olefins. Particular olefin monomers may be one or more of 1-hexene, 1-heptene, 1-octene, 1-nonene, 1-decene, 1-undecene, 1-dodecene, 1-tridecene, 1-tetradecene, 3-methyl-1-butene, 1-tetradecene and mixtures thereof. In another embodiment, the alpha olefin is selected from the group consisting of 1-hexene, 1-octene, 1-decene, 1-dodecene, and 1-tetradecene, either singly or mixtures thereof. In another embodiment, the alpha olefin is selected from the group consisting of 1-octene, 1-decene, 1-dodecene, and 1-tetradecene, either singly or mixtures thereof. In another embodiment, the alpha olefin is selected from the group consisting of 1-decene, 1-dodecene, and 1-tetradecene, either singly or mixtures thereof.

In one embodiment, the process described herein may be used to produce homo-oligomers or co-oligomers (for the purposes of this disclosure and the claims thereto, a co-oligomer may comprise two, three, four, or more different monomer units). Oligomers produced herein include homo-oligomers or co-oligomers of any of the above monomers. In an embodiment the oligomer is a homo-oligomer of any $C_8$ to $C_{12}$ alpha-olefin. Preferably the oligomer is a homo-oligomer of 1-hexene, 1-heptene, 1-octene, 1-nonene, 1-decene, 1-undecene, or 1-dodecene. In one embodiment, the oligomer is a homo-oligomer of decene. In another embodiment the oligomer is a co-oligomer comprising decene and one or more of any of the monomers listed above.

The alpha-olefins used to make sPAOs include, but are not limited to, $C_6$ to $C_{24}$ alpha-olefins, with the $C_6$ to $C_{14}$ alpha-olefins, such as 1-hexene, 1-heptene, 1-octene, 1-nonene, 1-decene, 1-undecene, 1-dodecene, 1-tridecene and 1-tetradecene being preferred. A group of obtainable polyalpha-olefins are poly-1-hexene, poly 1-heptene, poly-1-octene, poly-1-nonene, poly-1-decene, poly 1-undencen, poly-1-dodecene, poly-1-tridecene, and poly-1-tetradecene; dimers of higher olefins in the range of $C_{12}$ to $C_{18}$ may be present in the final products. Useful sPAO's are dimers, trimers, tetramers, pentamers, and higher oligomers or polymers with carbon numbers starting from $C_{20}$ and higher made from $C_4$ to $C_{18}$ alpha-olefins in one embodiment, and oligomers or polymers with carbon number starting from $C_{20}$ and higher made from $C_6$ to $C_{14}$ alpha-olefins in another embodiment. Suitable olefins include 1-butene, 1-pentene, 1-hexene, 1-heptene, 1-octene, 1-nonene, 1-decene, 1-undodecene and 1-dodecene, 1-tridecene, 1-tetradecene. In one embodiment, the olefin is 1-decene, and the sPAO is a mixture of dimers, trimers, tetramers and pentamers (and higher) of 1-decene. In another embodiment, the olefin is 1-decene, and the sPAO is a mixture of trimers, tetramers and pentamers (and higher) of 1-decene. In another embodiment, the olefin is 1-octene, and the sPAO is a mixture of trimers, tetramers and pentamers (and higher) of 1-octene. In another embodiment, the olefin is 1-hexene, and the sPAO is a mixture of tetramers and pentamers (and higher) of 1-hexene.

In another embodiment, the sPAO comprises two or more monomers, or may comprise three or more monomers, or may comprise four or more monomers, or may comprise five or more monomers. For example, a $C_8$ and $C_{10}$ mixture, a $C_8$ and $C_{12}$ mixture, a $C_8$ and $C_{14}$ mixture, a $C_8$, $C_{10}$, $C_{12}$-linear alpha-olefin mixture, a $C_8$, $C_{10}$, $C_{14}$ mixture, a $C_6$, $C_{10}$, $C_{14}$ linear alpha-olefin mixture, a $C_6$, $C_8$, $C_{10}$, $C_{12}$ linear alpha-olefin mixture, a $C_6$, $C_8$, $C_{10}$, $C_{14}$ linear alpha-olefin mixture, a $C_6$, $C_8$, $C_{12}$, $C_{14}$ linear alpha-olefin mixture, or a $C_4$, $C_6$, $C_8$, $C_{10}$, $C_{12}$, $C_{14}$, $C_{16}$, $C_{18}$-linear alpha-olefin mixture can be used as a feed.

In an alternative embodiment, the sPAO comprises less than 50 mole % of $C_2$, $C_3$, $C_4$ and $C_5$ monomers, preferably less than 40 mole %, preferably less than 30 mole %, preferably less than 20 mole %, preferably less than 10 mole %, preferably less than 5 mole %, preferably less than 3 mole %, preferably 0%. Specifically, in an alternative embodiment, the sPAO comprises less than 50 mole % of ethylene, propylene, butene and pentene, preferably less than 40 mole %, preferably less than 30 mole %, preferably less than 20 mole %, preferably less than 10 mole %, preferably less than 5 mole %, preferably less than 3 mole %, preferably 0%. In another embodiment, the sPAO comprises less than 40 mole % of ethylene. In another embodiment, the sPAO comprises less than 40 mole % of propylene. In another embodiment, the sPAO comprises less than 40 mole % of butene. In another embodiment, the sPAO comprises less than 40 mole % of pentene. In another embodiment, the sPAO comprises less than 10 mole % of ethylene. In another embodiment, the sPAO comprises less than 10 mole % of propylene. In another embodiment, the sPAO comprises less than 10 mole % of butene. In another embodiment, the sPAO comprises less than 10 mole % of pentene. In another embodiment, the sPAO comprises less than 1 mole % of ethylene. In another embodiment, the sPAO comprises less than 1 mole % of propylene. In another embodiment, the sPAO comprises less than 1 mole % of butene. In another embodiment, the sPAO comprises less than 1 mole % of pentene.

The alpha-olefins used herein can be produced directly from ethylene growth process as practiced by several commercial production processes, or they can be produced from Fischer-Tropsch hydrocarbon synthesis from $CO/H_2$ syngas, or from metathesis of internal olefins with ethylene, or from cracking of petroleum or Fischer-Tropsch synthetic wax at high temperature, or any other alpha-olefin synthesis routes. A preferred feed for this disclosure is preferably at least 80 weight % alpha-olefin (preferably linear alpha olefin), preferably at least 90 weight % alpha-olefin (preferably linear alpha olefin), more preferably 100% alpha-olefin (preferably linear alpha olefin). However, alpha-olefin mixtures can also be used as feeds in this disclosure, especially if the other components are internal-olefins, branched olefins, paraffins, cyclic paraffins, aromatics (such as toluene and or xylenes). These components have diluent effects and are believed to not have a substantial detrimental effect on the polymerization of alpha-olefins. In other words, the process described herein can selectively convert alpha-olefins in a mixture and leave the other components unreacted. This is particularly useful when ethylene is not present in the mixture. This technology can be used to separate out alpha-olefins from a mixture by selectively reacting them with polymerization or oligomerization catalyst systems completely eliminating the need to separate alpha-olefins from the remainder of the components in a mixed feedstream. This is economically advantageous, for example, in a process utilizing Fisher-Tropsch synthesis olefin product streams containing alpha-olefins, internal-olefins and branched olefins. Such a mixture can be fed to the oligomerization technology as described herein and to selectively react away the alpha-olefin. No separate step to isolate the alpha-olefin is needed. Another example of the utility of this process involves-alpha-olefins produced by the metathesis of internal olefins with ethylene, which may contain some internal olefins. This mixed olefin base stock feed can be reacted as is in the polymerization/oligomerization process of the present disclosure, which selectively converts the alpha-olefins into lube products. Thus one can use the alpha-olefin for the base stock synthesis without having to separate the alpha-olefin from internal olefin. This can bring a significant improvement in process economics.

In a preferred embodiment, the sPAO's produced herein may contain monomers having branches at least 2, preferably at least 3 carbons away from the alpha-unsaturation, such 4-methyl-1-decene, 4-ethyl-1-decene, or 4-methyl-1-hexene, 4-methyl-1-pentene, etc. These olefins may be present in the linear alpha-olefins from the manufacturing process or they can be added deliberately. The copolymers of slightly branched alpha-olefins with completely linear alpha-olefins have improved low temperature properties.

In a preferred embodiment, any of the sPAO's described herein may comprise at least 50 mole % $C_4$ to $C_{24}$ alpha olefins and from 0.5 to 20 mole % ethylene. Preferably any of the sPAO's described herein may comprise at least 60 mole % monomers having 5 to 24 carbon atoms (preferably at least 70 mole %, preferably at least 80 mole %, preferably at least 85 mole %, preferably at least 90 mole %, preferably at least 95 mole %) and from 0.5 to 20 mole % ethylene (preferably from 1 to 15 mole %, preferably from 2 to 10 mole %, preferably form 2 to 5 mole %).

Polymerization/Oligomerization Process

In another embodiment, the present application is directed to an improved process for polymerization or oligomerization of alpha-olefins, the process comprising contacting one or more $C_4$ to $C_{24}$ alpha-olefins with
(A) a pre-catalyst as previously described above and represented by any of formulae 1, 1a, 1b, 2, 3 or 3a having $C_s$ or pseudo-$C_s$ symmetry, or by formula 2 having $C_2$ symmetry;
(B) non-coordinating anion activator,
(C) a trialkylaluminum, such as tri-isobutylaluminum, tri-n-hexylaluminum, tri-n-octylaluminum, tri-n-decylaluminum, tri-n-dodecylaluminum,
(D) optionally in the absence of hydrogen or in the presence of a limited amount of hydrogen, and in the absence of an alkylalumoxane, under reaction temperature and pressure conditions sufficient to polymerize or oligomerize said alpha-olefins. In another embodiment, the non-coordinating anion activator comprises N,N-dimethylanilinium tetra (perfluorophenyl)borate. In a further embodiment, the $C_s$ or pseudo-$C_s$ symmetric catalyst is represented by formula 1 or 1a. In another embodiment, the catalyst comprises diphenylmethylidene(cyclopentadienyl)(9-fluorenyl)zirconium dichloride (also called diphenylmethylene(cyclopentadienyl)(9-fluorenyl)zirconium dichloride.

The reaction temperature is from 30° C. to 200° C., preferably 50 to 160° C., more preferably 60 to 150° C., more preferably 70 to 140° C. and the hydrogen partial pressure in the reactor is from 5 psig to 300 psig, preferably 10 to 200 psi, preferably 20 to 200 psi, preferably 25 to 150 psi. The total reactor pressure can be from 10 psi to 1000 psi by having some inert gas, such as nitrogen or argon, in the reactor, or by having the partial pressure from the feed olefins, especially if the olefins are $C_2$ to $C_6$ olefins which have relatively high partial vapor pressure under reaction conditions. The preferred total reactor pressure can be from 10 psi to 800 psi, preferably from 15 psi to 500 psi, from 15 psi to 300 psi or from 15 psi to 200 psi.

The mole ratio of metallocene catalyst to non-coordinating anion activator is from 5 to 0.2. An alternative ratio is from 2 to 0.5, or from 1.5 to 0.7, or from 1.2 to 0.8 or from 1.1 to 0.9. The metallocene concentration is selected to be less than 1 mg per gram of olefin feed, or less than 0.1 mg per gram of olefin feed, or less than 50 microgram per gram of olefin feed, or less than 30 microgram per gram of olefin feed, or less than 20 microgram per gram of olefin feed, or less than 10 microgram per gram of olefin feed, or less than 5 microgram per gram of olefin feed, or less than 2 microgram per gram of olefin feed. Sometimes, a slightly higher amount of catalyst may be used so that the reaction is completed in a selected time, or to compensate for potential poisons that may be present in the reactor. In general, the goal is to keep the catalyst concentration at an optimum level to maintain good conversion within reasonable time and avoid shutting down the reactor due to poison.

In the polymerization process, a co-activator is optionally used. The co-activator converts the halides or salts of the metallocenes into metal alkyls. The co-activator to metallocene ratio can range from 2 to 200, or from 4 to 100 or from 4 to 20. The co-activator in the disclosed embodiments may be tri-isobutylaluminum, tri-n-octylaluminum, or tri-n-hexylaluminum.

A scavenger, usually a tri-alkylaluminum compound or other reactive chemical, may be added to scavenge all impurity in feed or solvent system. The scavenger can be the same or different from the co-activator. The molar ratio of the aluminum compound to metallocene compound can be ranged from 4 to 1000, preferably from 10 to 500, preferably from 20 to 500, preferably from 50 to 300, preferably from 75 to 300, preferably from 100 to 300, more preferably from 150 to 200. The large amount of the right scavenger significantly improves catalyst productivity.

Many polymerization/oligomerization processes and reactor types used for metallocene-catalyzed polymerizations or oligomerizations such as solution, slurry, and bulk polymerization or oligomerization processed can be used in this disclosure. In some embodiments, if a solid or supported catalyst is used, a slurry or continuous fixed bed or plug flow process is suitable. In a preferred embodiment, the monomers are contacted with the metallocene compound and the activator in the solution phase, bulk phase, or slurry phase, preferably in a continuous stirred tank reactor, continuous tubular reactor, or a batch reactor. The monomer(s), metallocene, and activator are contacted for a residence time of 1 second to 100 hours, or 30 seconds to 50 hours, or 2 minutes to 6 hours, or 1 minute to 4 hours. In another embodiment, solvent or diluent is present in the reactor and is preferably selected from the group consisting of butanes, pentanes, hexanes, heptanes, octanes, nonanes, decanes, undecanes, dodecanes, tridecanes, tetradecanes, pentadecanes, hexadecanes, toluene, o-xylene, m-xylene, p-xylene, ethylbenzene, isopropylbenzene, and n-butylbenzene; preferably toluene and or xylenes and or ethylbenzene, normal paraffins (such as Norpar solvents available for ExxonMobil Chemical Company, Houston, Tex.), or isoparaffin solvents (such as Isopar solvents available for ExxonMobil Chemical Company, Houston, Tex.). These solvents or diluents are usually pre-treated in same manners as the feed olefins.

Typically, in the processes of this disclosure, one or more transition metal compounds, one or more activators, and one or more monomers are contacted to produce polymer or oligomer. These catalysts may be supported and as such will be particularly useful in the known slurry, solution, or bulk operating modes conducted in single, series, or parallel reactors. If the catalyst, activator or co-activator is a soluble compound, the reaction can be carried out in a solution mode. Even if one of the components is not completely soluble in the reaction medium or in the feed solution, either at the beginning of the reaction or during or at the later stages of the reaction, a solution or slurry type operation is still applicable. In any instance, the catalyst components, dissolved or suspended insolvents, such as toluene or other conveniently available aromatic solvents, or in aliphatic solvent, or in the feed alpha-olefin stream, are fed into the reactor under inert atmosphere (usually nitrogen or argon blanketed atmosphere) to allow the polymerization or oligomerization to take place. The polymerization or oligomerization can be run in a batch mode, where all the components are added into a reactor and allowed to react to a pre-designed degree of conversion, either to partial conversion or full conversion. Subsequently, the catalyst is deactivated by any possible means, such as exposure to air or water, or by addition of alcohols or solvents containing deactivating agents. The polymerization or oligomerization can also be carried out in a semi-continuous operation, where feeds and catalyst system components are continuously and simultaneously added to the reactor so as to maintain a constant ratio of catalyst system components to feed olefin(s). When all feeds and catalyst components are added, the reaction is allowed to proceed to a pre-determined stage. The reaction is then discontinued by catalyst deactivation in the same manner as described for batch operation. The polymerization or oligomerization can also be carried out in a continuous operation, where feeds and catalyst system components are continuously and simultaneously added to the reactor so to maintain a constant ratio of catalyst system and feed olefins. The reaction product is continuously withdrawn from the reactor, as in a typical continuous stirred tank reactor (CSTR) operation. The residence times of the reactants are controlled by a pre-determined degree of conversion. The withdrawn product is then typically quenched in the separate reactor in a similar manner as other operation. In a preferred embodiment, any of the processes to prepare sPAO's described herein are continuous processes. Preferably the continuous process comprises the steps of a) continuously introducing a feed stream comprising at least 10 mole % of the one or more $C_6$ to $C_{24}$ alpha-olefins into a reactor, b) continuously introducing the metallocene compound, co-activator, and the activator into the reactor, and c) continuously withdrawing the polyalpha-olefin from the reactor. In another embodiment, the continuous process comprises the step of maintaining a partial pressure of hydrogen in the reactor of 200 psi (1379 kPa) or less, based upon the total pressure of the reactor, or 150 psi (1034 kPa) or less, or 100 psi (690 kPa) or less, or 50 psi (345 kPa) or less, or 25 psi (173 kPa) or less, or 10 psi (69 kPa) or less. Alternatively the hydrogen, if present, is present in the reactor at 1000 ppm or less by weight, or 750 ppm or less, or 500 ppm or less, or 250 ppm or less, or 100 ppm or less, or 50 ppm or less, or 25 ppm or less, or 10 ppm or less, or 5 ppm or less. Alternatively the hydrogen, if present, is present in the feed at 1000 ppm or less by weight, or 750 ppm or less, or 500 ppm or less, or 250 ppm or less, or 100 ppm or less, or 50 ppm or less, or 25 ppm or less, or 10 ppm or less, or 5 ppm or less.

Reactors range in size from 2 ml and up, with commercial production reactors having a volume of at least one liter. A production facility may have one single reactor or several reactors arranged in series or in parallel or in both to maximize productivity, product properties and general process efficiency. The reactors and associated equipments are usually pre-treated to ensure proper reaction rates and catalyst performance. The reaction is usually conducted under inert atmosphere, where the catalyst system and feed components will not be in contact with any catalyst deactivator or poison which is usually polar oxygen, nitrogen, sulfur or acetylenic compounds.

One or more reactors in series or in parallel may be used in the present disclosure. The transition metal compound, activator and when required, co-activator, may be delivered as a solution or slurry in a solvent or in the alpha-olefin feed stream, either separately to the reactor, activated in-line just prior to the reactor, or preactivated and pumped as an activated solution or slurry to the reactor. Polymerizations/oligomerizations are carried out in either single reactor operation, in which monomer, or several monomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the precatalyst is activated in the reactor in the presence of olefin. In another embodiment, the precatalyst such as the dichloride form of the metallocenes is pre-treated with alkylalumum reagents, especially, triisobutylaluminum, tri-n-hexylaluminum and/or tri-n-octylaluminum, followed by charging into the reactor containing other catalyst component and the feed olefins, or followed by pre-activation with the other catalyst component to give the fully activated catalyst, which is then fed into the reactor containing feed olefins. In another alternative, the pre-catalyst metallocene is mixed with the activator and/or the co-activator and this activated catalyst is then charged into reactor, together with feed olefin stream containing some scavenger or co-activator. In another alternative, the whole or part of the co-activator is pre-mixed with the feed olefins and charged into the reactor at the same time as the other catalyst solution containing metallocene and activators and/or co-activator.

In some embodiments, a small amount of poison scavenger, such as trialkylaluminum (trimethylaluminum, triethylaluminum, triisopropylaluminum, triisobutylaluminum, tri-n-hexylaluminum, tri-n-octylaluminum) or methylalumoxane is added to the feed olefin stream to further improve catalyst activity. In a preferred embodiment, the monomers are contacted with an alkylaluminum compound, preferably a trialkylaluminum compound, prior to being introduced into the reactor. In another preferred embodiment, the metallocene and or activator are combined with an alkylaluminum compound, preferably a trialkylaluminum compound, prior to entering the reactor. Preferably the alkylaluminum compound is represented by the formula: $R_3Al$, where each R is independently a $C_1$ to $C_{20}$ alkyl group, preferably the R groups are independently selected from the group consisting of methyl, ethyl, propyl, isopropyl, butyl, isobutyl, n-butyl, pentyl, isopentyl, n-pentyl, hexyl, isohexyl, n-hexyl, heptyl, octyl, isocotyl, n-octyl, nonyl, isononyl, n-nonyl, decyl, isodecyl, n-cecyl, undecyl, isoundecyl, n-undecyl, dodecyl, isododecyl, and n-dodecyl, preferably isobutyl, n-octyl, n-hexyl, and n-dodecyl. Preferably the alkylaluminum compound is selected from tri-isobutylaluminum, tri-n-octylaluminum, tri-n-hexylaluminum, and tri-n-dodecylaluminum.

In one embodiment of any of the process described herein the feed olefins and or solvents are treated to remove catalyst poisons, such as peroxides, oxygen or nitrogen-containing organic compounds or acetylenic compounds. The treatment of the linear alpha-olefin with an activated 13× molecular sieve and a de-oxygenation catalyst, i.e., a reduced copper catalyst, increased catalyst productivity more than 10-fold. Alternatively, the feed olefins and or solvents are treated with an activated molecular sieve, such as 3 A, 4 A, 8 A or 13× molecular sieve, and/or in combination with an activated alumina or an activated de-oxygenated catalyst. Such treatment will increase catalyst productivity 2- to 10-fold or more. The improved process also includes special treatment of the feed olefins to remove catalyst poisons, such as peroxides, oxygen, sulfur or nitrogen-containing organic compounds or other trace impurities. This treatment can increase catalyst productivity substantially (typically more than 10-fold). Preferably the feed olefins are contacted with a molecular sieve, activated alumina, silica gel, oxygen removing catalyst, and or purifying clays to reduce the heteroatom-containing compounds in the feed, preferably below 50 ppm, preferably below 10 ppm.

The catalyst compositions can be used individually or can be mixed with other known polymerization catalysts to prepare polymer or oligomer blends. Monomer and catalyst selection allows polymer or oligomer blend preparation under conditions analogous to those using individual catalysts. Polymers having increased MWD are available from polymers made with mixed catalyst systems and can thus be achieved. Mixed catalyst can comprise two or more catalyst precursors and or two or more activators.

Generally, when using metallocene catalysts, after pretreatment of feed olefins, solvents, diluents and after precautions to keep the catalyst component stream(s) and reactor free of impurities, the reaction should proceed well. In some embodiments, when using metallocene catalysts, particularly when they are immobilized on a support, the complete catalyst system will additionally comprise one or more scavenging compounds. Here, the term scavenging compound means a compound that removes polar impurities from the reaction environment. These impurities adversely affect catalyst activity and stability. Typically, purifying steps are usually used before introducing reaction components to a reaction vessel. But such steps will rarely allow polymerization or oligomerization without using some scavenging compounds. Normally, the polymerization process will still use at least small amounts of scavenging compounds.

Typically, the scavenging compound will be an organometallic compound such as the group 13 organometallic compounds of U.S. Pat. Nos. 5,153,157, 5,241,025 and WO-A-91/09882, WO-A-94/03506, WO-A-93/14132, and WO 95/07941. Exemplary compounds include previously disclosed trialkylaluminums. Scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. Alumoxanes also may be added in scavenging quantities with other activators, e.g., methylalumoxane, $[Me_2HNPh]^+[B(pfp)_4]^-$ or $B(pfp)_3$, where pfp is perfluorophenyl ($C_6F_5$), Me is methyl and Ph is phenyl.

In a preferred embodiment ethylene is present in the feed at 10 mole % or less, preferably 0.5 to 8 moles %, preferably 0.5 to 5 mole %, preferably from 1 to 3 mole %.

The sPAO's described herein can also be produced in homogeneous solution processes. Generally this involves polymerization or oligomerization in a continuous reactor in which the polymer formed and the starting monomer and catalyst materials supplied, are agitated to reduce or avoid concentration or temperature gradients. Temperature control in the reactor is generally obtained by balancing the heat of polymerization and with reactor cooling by reactor jackets or cooling coils or a cooled side-stream of reactant to cool the contents of the reactor, auto refrigeration, pre-chilled feeds, vaporization of liquid medium (diluent, monomers or solvent) or combinations of the above. Adiabatic reactors with pre-chilled feeds may also be used. The reactor temperature depends on the catalyst used and the product desired. Higher temperatures tend to give lower molecular weights and lower temperatures tend to give higher molecular weights, however this is not a hard and fast rule. In order to produce fluids with narrow molecular distribution, such as to promote the highest possible shear stability, it is useful to control the reaction temperature to obtain minimum of temperature fluctuation in the reactor or over the course of the reaction time. If multiple reactors are used in series or in parallel, it is useful to keep the temperature constant in a pre-determined value to minimize any broadening of molecular weight distribution. In order to produce fluids with broad molecular weight distribution, one can adjust the reaction temperature swing or fluctuation, or as in series operation, the second reactor temperature is preferably higher than the first reactor temperature. In parallel reactor operation, the temperatures of the two reactors are independent. One can also use two types of metallocene catalyst.

The reaction time or reactor residence time is usually dependent on the type of catalyst used, the amount of catalyst used, and the desired conversion level. Different metallocenes have different activities. Usually, a higher degree of alkyl substitution on the cyclopentadienyl ring, or bridging, improves catalyst productivity. Catalysts such as diphenylmethylidene(cyclopentadienyl)(9-fluorenyl)zirconium dichloride, isopropyl idene(cyclopentadienyl)(9-fluorenyl)zirconium dichloride, diphenylsilylene(cyclopentadienyl)(9-fluorenyl)zirconium dichloride, dimethylsilylene (cyclopentadienyl)(9-fluorenyl)zirconium dichloride, and ethylene(cyclopentadienyl)(9-fluorenyl)zirconium dichloride, and mixtures thereof are particularly useful herein.

The amount of catalyst components used may be determinative for reaction efficiency. High amount of catalyst loading may give high conversion at short reaction time. However, high amount of catalyst usage makes the production process uneconomical and it may be difficult to manage the reaction heat or to control the reaction temperature. Therefore, for the disclosed invention, it is useful to choose a catalyst with maximum catalyst productivity to minimize the amount of precatalyst and the amount of activator needed. When the catalyst system is a metallocene plus a Lewis acid or an ionic activator with a NCA component, the metallocene used is typically in the range of 0.01 microgram to 500 micrograms of metallocene component/gram of alpha-olefin feed. Usually the preferred range is from 0.1 microgram to 100 microgram of metallocene component per gram of alpha-olefin feed. Furthermore, the molar ratio of the NCA activator to metallocene is in the range from 0.1 to 10, preferably 0.5 to 5, preferably 0.5 to 3. If a co-activator of alkylaluminum compound is used, the molar ratio of the Al to metallocene is in the range from 1 to 1000, alternatively 2 to 500, alternatively 4 to 400, alternatively 4 to 200, alternatively 4 to 50.

Typically one prefers to have the highest possible conversion (close to 100%) of feed alpha-olefin in shortest possible reaction time. However, in CSTR operation, sometimes it is beneficial to run the reaction at an optimum conversion, which is slightly less than 100% conversion. There are also occasions, when partial conversion is more desirable when the narrowest possible MWD of the product is desirable because partial conversion can avoid a MWD broadening effect. If the reaction is conducted to less than 100% conversion of the alpha-olefin, the unreacted starting material after separation from other product and solvents/diluents can be recycled to increase the total process efficiency.

When a solid supported catalyst is used, a slurry polymerization/oligomerization process generally operates in the similar temperature, pressure and residence time range as described previously. In a slurry polymerization or oligomerization, a suspension of solid catalyst, promoters, monomer and comonomers are added. The suspension including diluent is intermittently or continuously removed from the reactor. The catalyst is then separated from the product by filtration, centrifuge or settlement. The fluid is then distilled to remove solvent, any unreacted components and light product. A portion or all of the solvent and unreacted component or light components can be recycled for reuse.

If the catalyst used is a solution catalyst (i.e. not supported), when the reaction is complete (such as in a batch mode), or when the product is withdrawn from the reactor (such as in a CSTR), the product may still contain soluble, suspended or mixed catalyst components. These components are preferably deactivated or removed. Any of the usual catalyst deactivation methods or aqueous wash methods can be used to remove the catalyst component. Typically, the reaction is deactivated by addition of stoichiometric amount or excess of air, moisture, alcohol, isopropanol, etc. The mixture is then washed with dilute sodium hydroxide or with water to remove catalyst components. The residual organic layer is then subjected to distillation to remove solvent, which can be recycled for reuse. The distillation can further remove any light reaction product from $C_{18}$ and less. These light components can be used as diluent for further reaction. Or they can be used as olefinic raw material for other chemical synthesis, as these light olefin product have vinylidene unsaturation, most suitable for further functionalization to convert in high performance fluids. Or these light olefin products can be hydrogenated to be used as high quality paraffinic solvents.

Alternatively, a different catalyst removal method is used. After the polymerization reaction is deactivated by the addition of stoichiometric amount of excess air, moisture, alcohol, isopropanol, etc., a small amount of solid sorbent, such as Celite, silica gel, alumina gel, natural clay, synthetic clay, modified clay, diatomaceous earth, activated charcoal, silica gel, alumina, aluminosilicate, zeolites, molecular sieves, cellulose material, metal oxides or metal salts, such as calcium oxides, magnesium oxides, titanium oxides, zirconium oxides, aluminum oxides, activated or treated in appropriate manners. The solid sorbent can absorb most of the catalyst components. After slurry for appropriate amount of time, the solid sorbent can be removed by filtration. The liquid product can then be subjected to similar distillation as described earlier to isolate desirable products.

In another embodiment, any of polyalphaolefins produced herein is hydrogenated. In particular the polyalpha-olefin is preferably treated to reduce heteroatom containing compounds to less than 600 ppm, and then contacted with hydrogen and a hydrogenation catalyst to produce a polyalpha-olefin having a Bromine number less than 1.8. In a preferred embodiment, the treated polyalpha-olefin comprises 100 ppm of heteroatom containing compounds or less, preferably 10 ppm of heteroatom containing compounds or less. (A heteroatom containing compound is a compound containing at least one atom other than carbon and hydrogen.) Preferably the hydrogenation catalyst is selected from the group consisting of supported group 7, 8, 9, and 10 metals, preferably the hydrogenation catalyst selected from the group consisting of one or more of Ni, Pd, Pt, Co, Rh, Fe, Ru, Os, Cr, Mo, and W, supported on silica, alumina, clay, titania, zirconia, or mixed metal oxide supports. A preferred hydrogenation catalyst is nickel supported on Kieselguhr, or platinum or palladium supported on alumina, or cobalt-molydenum supported on alumina. Usually, a high nickel content catalyst, such as 60% Ni on Kieselguhr catalyst is used, or a supported catalyst with high amount of Co—Mo loading. Alternatively, the hydrogenation catalyst is nickel supported on Kieselguhr, silica, alumina, clay or silica-alumina.

In one embodiment the polyalpha-olefin is contacted with hydrogen and a hydrogenation catalyst at a temperature from 25 to 350° C., preferably 100 to 300° C. In another embodiment the polyalpha-olefin is contacted with hydrogen and a hydrogenation catalyst for a time period from 5 minutes to 100 hours, preferably from 5 minutes to 24 hours. In another embodiment the polyalpha-olefin is contacted with hydrogen and a hydrogenation catalyst at a hydrogen pressure of from 25 psi to 2500 psi, preferably from 100 to 2000 psi. In another embodiment the hydrogenation process reduces the number of mm triad groups in a polyalpha-olefin by 1 to 80%. Preferably the sPAO has 10 to 80% less mm triad groups than the polyalpha-olefin prior to contact with the hydrogen and hydrogenation catalyst. For further information on hydrogenation of sPAO's please see U.S. Pat. No. 5,573,657 and "Lubricant Base Oil Hydrogen Refining Processes" (page 119 to 152 of Lubricant Base Oil and Wax Processing, by Avilino Sequeira, Jr., Marcel Dekker, Inc., NY, 1994).

This hydrogenation process can be accomplished in a slurry reactor in a batch operation or in a continuous stirred tank reactor (CSTR), where the catalyst in 0.001 wt % to 20 wt % of the sPAO feed or preferably 0.01 to 10 wt %, hydrogen and the polyalpha-olefins are continuously added to the reactor to allow for certain residence time, usually 5 minutes to 10 hours to allow complete hydrogenation of the unsaturated olefins and to allow proper conversion of the mm diads. The amount of catalyst added is usually very small just to compensate for the catalyst deactivation. The catalyst and hydrogenated sPAO are continuously withdrawn from the reactor. The product mixture was then filtered, centrifuged or settled to remove the solid hydrogenation catalyst. The catalyst can be regenerated and reused. The hydrogenated sPAO can be used as is or further distilled or fractionated to the right component if necessary. In some cases, when the hydrogenation catalyst show no catalyst deactivation over long term operation, the stir tank hydrogenation process can be carried out in a manner where a fixed amount of catalyst is maintained in the reactor, usually 0.1 wt % to 10 wt % of the total reactant, and only hydrogen and sPAO feed are continuously added at certain feed rate and only hydrogenated sPAO was withdrawn from the reactor.

The hydrogenation process can also be accomplished by a fixed bed process, in which the solid catalyst is packed inside a tubular reactor and heated to reactor temperature. Hydrogen and sPAO feed can be fed through the reactor simultaneously from the top or bottom or countercurrently to maximize the contact between hydrogen, sPAO and catalyst and to allow best heat management. The feed rate of the sPAO and hydrogen are adjusted to give proper residence to allow complete hydrogenation of the unsaturated olefins in the feed and to allow desirable conversion of mm triads in the process. The hydrogenated sPAO fluid can be used as is or further distilled or fractionated to give the right component, if necessary. Usually, the finished hydrocarbon sPAO fluids have Bromine number less than 2 and have reduced amount of mm triads than the unhydrogenated sPAO.

The new poly-alpha-olefins, when used alone or blended with other fluid, have unique lubrication properties.

In another embodiment, a novel lubricant of the present disclosure comprises the sPAO's produced in this disclosure, together with one or more other base stocks, including Group I to Group V base stocks with viscosity range from 1.5 to 100 cSt at 100° C. to formulate suitable viscosity grades. In addition, additives of one or more of: thickeners, VI improvers, antioxidants, anti-wear additives, detergent/dispersant/inhibitor (DDI) packages, and/or anti-rust additives may be added. In a preferred embodiment the sPAO's produced herein are combined with one or more of dispersants, detergents, friction modifiers, traction improving additives, demulsifiers, defoamants, chromophores (dyes), and/or haze inhibitors. These fully formulated lubricants can be used in automotive crank case oil (engine oil), industrial oil, grease, or gas turbine engine oil. These are examples of additives used in finished lubricant formulations. Additional information on the use of sPAO's in the formulations of full synthetic, semi-synthetic or part synthetic lubricant or functional fluids can be found in "Synthetic Lubricants and High-Performance Functional Fluids," 2nd Ed. L. Rudnick, ed. Marcel Dekker, Inc., N.Y. (1999). Additional information on additives used in product formulation can be found in "Lubricants and Lubrications," T. Mang and W. Dresel, eds., Wiley-VCH GmbH, Weinheim 2001.

The sPAO's produced in this disclosure can be used in the formulation of automotive engine lubricants, industrial lubricants, greases, hydraulic lubricants, etc. with improved viscometrics, superior low temperature properties, leading to improved fuel economy or energy efficiency, or significantly improved wear protection and cleanliness. For example, the sPAO can be used in typical automotive engine lubricant formulation to improve VI, alone or used together with other traditional VI improver (OCP (olefin-copolymer) or polymethacrylates). In the engine oil formulation, the other suitable base stocks used in the blend include API Groups I to V, low viscosity fluids, in proper portions. In addition, additives are added to the formulation. Typical additives include antioxidants, anti-wear agents, dispersants, detergents, extreme-pressure additives, corrosion inhibitors, defoamant agents, etc. Examples of automotive engine lubricant formulations and additives can be found in U.S. Pat. No. 6,713,438.

The sPAOs produced herein may provide high viscoelastic properties as indicated by its unexpectedly high first normal stress difference. This polymer component in the lubricant provides unexpectedly high film thickness and unexpectedly good wear protection under conditions where high molecular weight polymers, such conventional VI improver, lose some or all of their thickening power, for example, at high shear rates in lubrication contact zones. The use of the sPAO with highly viscoelastic property enables the production of very widely cross-graded engine oils, especially oils with a low temperature grading of 0W or better. Oils with cross gradings of 0W-20, 0W-30, 0W-40 or even more widely cross-graded, for example 0W-70 or higher may be achieved. Engine oils, cross-graded such as 0W-70 and 25W-70, may achieve excellent wear performance even under conditions of high levels of fuel dilution, indicating that the use of the low molecular weight highly viscoelastic component in combination with the high molecular weight polymer component is capable of countering the deleterious oil film thinning effects of fuel dilution on low viscosity base oils. Another particular achievement of this disclosure is in formulating very low viscosity highly fuel efficient oils with a 0W low temperature rating, which have a cross-grading of 0W-20 or wider, such as 0W-30, which are capable of passing the ASTM Sequence VE wear test, in which high levels of fuel, water, and blow-by contaminants accumulate in the oil during the 12-day, low-temperature test. Although it has previously been possible to pass the high-temperature Sequence III E wear test with a very low-viscosity 0W-20 or 0W-30 oil, passing the very demanding Sequence V E test had so far been highly elusive. The new sPAO produced herein may provide such opportunities. These are possible unique applications for these new sPAOs in automotive lubricant formulations.

The PAO disclosed in this disclosure can be used in industrial lubricant formulations. In industrial lube formulations, 1 to 99 wt % or 1 to 90 wt %, or 50 to 99 wt %, or 55 to 90 wt %, or 5 wt % to 45 wt %, or 5 to 60 wt %, or 5 to 45 wt % or 20% to 60% of one, or more than one, viscosity grade of the sPAO in this disclosure is blended with one or more of the API Group I to V basestocks to give the base oil for the industrial lube formulation. Often, one or multiple of these other base stocks are chosen to blend with sPAOs to obtain the optimized viscometrics and the performance. Further, preferred embodiments relate to the viscosity index of the base stocks usable as blending components in this disclosure, where in some instances the viscosity index is preferably 80 or greater, more preferably 100 or greater, and even more preferably 120 or greater. Additionally, in certain particular instances, viscosity index of these sPAOs may be preferably 130 or greater, more preferably 135 or greater, and even more preferably 140 or greater. In addition to these sPAOs described above, in a preferred embodiment a second class of fluids, selected to be different from the fluids discussed above, and preferably having a higher polarity is also added to the formulation. The polarity of a fluid may be determined by one of ordinary skill in the art, such as by aniline points as measured by ASTM D611 method. Usually fluids with higher polarity will have lower aniline points. Fluids with lower polarity will have higher aniline points. Most polar fluids will have aniline points of less than 100° C. In preferred embodiments, such fluids are selected from the API Group V base stocks. Examples of these Group V fluids include alkylbenzenes (such as those described in U.S. Pat. Nos. 6,429,345, 4,658,072), and alkylnaphthalenes (e.g., U.S. Pat. Nos. 4,604,491, and 5,602,086). Other alkylated aromatics are described in "Synthetic Lubricants and High Performance Functional Fluids", M. M Wu, Chapter 7, (L. R. Rudnick and R. L. Shubkin, eds.), Marcel Dekker, NY, 1999.

The viscosity grade of the final product is adjusted by suitable blending of base stock components of differing viscosities. In many conventional industrial lubricant formulations, thickeners are used to increase viscosity. One particular advantage of the present disclosure is that thickeners are not necessary and in preferred embodiments no thickeners are used. sPAO fluids of different viscosity grades are most suitably used to achieve wide finished viscosity grades with significant performance advantages. Usually, differing amounts of the various basestock components (primary hydrocarbon base stocks, secondary base stock and any additional base stock components) of different viscosities, may be suitably blended together to obtain a base stock blend with a viscosity appropriate for blending with the other components (such as described below) of the finished lubricant. This may be determined by one of ordinary skill in the art in possession of the present disclosure without undue experimentation. The viscosity grades for the final product are preferably in the range of ISO 2 to ISO 1000 or even higher for industrial gear lubricant applications, for example, up to about ISO 46,000. For the lower viscosity grades, typically from ISO 2 to ISO 13,100, the viscosity of the combined base stocks will be slightly higher than that of the finished product, typically from ISO 2 to about ISO 220 but in the more viscous grades up to ISO 46,000, the additives will frequently decrease the viscosity of the base stock blend to a slightly lower value. With an ISO 680 grade lubricant, for example, the base stock blend might be 780-800 cSt (at 40° C.) depending on the nature and concentration(s) of the additives.

In addition to base stocks, many additives are used in industrial lubricant formulation. Examples of these additives include antioxidants, anti-wear additives, extreme pressure additives, dispersants, detergents, corrosion inhibitors, defoamants, etc.

Shear stability is important for many industrial oil operations. Higher shear stability means the oil does not lose its viscosity at high shear. Such shear-stable oil can offer better protection under more severe operation conditions. The oil compositions described in this disclosure have superior shear stability for industrial oil applications. The formulated oil containing sPAOs usually have excellent viscometrics, high VI, low temperature Brookfield viscosities, all these contributing to the energy efficiency for the lubricants.

Similarly, the sPAO can be used in automotive gear oil formulation, in grease and hydraulic oil formulation.

This disclosure relates to:
1. A liquid syndiotactic polyalphaolefin, sPAO, comprising one or more $C_4$ to $C_{24}$ monomers, said sPAO having:
    a) a rr triad content of 5 to 50% as measured by $^{13}C$ NMR;
    b) a mr triad content of 25 to 60% as measured by $^{13}C$ NMR, where the mr to mm triad ratio is at least 1.0;
    c) a pour point of Z ° C. or less, where Z=0.0648X-51.2, where X=kinematic viscosity at 100° C. as reported in centistokes (cSt);
    d) a kinematic viscosity at 100° C. of 50 cSt or more (alternatively 200 cSt or more);
    e) a ratio of mr triads to rr triad (as determined by $^{13}C$ NMR) of less than 9;
    f) a ratio of vinylidene to 1,2 disubstituted olefins (as determined by $^1H$ NMR) of less than 8;
    g) a viscosity index of 120 or more; and
    h) an Mn of 40,000 or less.
2. The sPAO of paragraph 1, wherein the kinematic viscosity at 100° C. is 100 cSt or more.
3. The sPAO of paragraph 1 or 2, where the monomers are $C_6$ to $C_{24}$ monomers.
4. The sPAO of any of paragraphs 1 to 3, or any combination thereof, wherein the sPAO has a Bromine number of less than 2.
5. The sPAO of any of paragraphs 1 to 3, or any combination thereof, wherein the sPAO has an as-polymerized Bromine number of less than 2.
6. The sPAO of any of paragraphs 1 to 5, or any combination thereof, wherein the sPAO has an Mw/Mn of 2.0 or less.
7. The sPAO of any of paragraphs 1 to 6, or any combination thereof, wherein the sPAO has 40 to 60 mole % of rr triads as determined by $^{13}C$ NMR.
8. The sPAO of any of paragraphs 1 to 7, or any combination thereof, wherein the sPAO has a Brookfield viscosity of 50,000 cP or less at −40° C. and a Brookfield viscosity of 50,000 cP or less at −55° C., where the Brookfield viscosity at −40° C. is at least 5,000 cP lower than the Brookfield viscosity at −55° C.
9. The sPAO of any of paragraphs 1 to 8, or any combination thereof, wherein the sPAO comprises more than 50 mole % of one or more $C_6$ to $C_{18}$ alpha-olefin monomers.
10. The sPAO of any of paragraphs 1 to 9, or any combination thereof, wherein the sPAO has a flash point of 200° C. or more.
11. The sPAO of any of paragraphs 1 to 10, or any combination thereof, wherein the monomers are alpha olefins selected from the group consisting of hexene, heptene, octene, nonene, decene, dodecene, 3-methyl-1-butene, and tetradecene.
12. The sPAO of any of paragraphs 1 to 10, or any combination thereof, wherein the monomers are alpha olefins selected from the group consisting of 1-octene, 1-nonene, 1-decene, 1-dodecene, 1-tetradecene and mixtures thereof.
13. The sPAO of any of paragraphs 1 to 10 or any combination thereof, wherein the monomers are a mixture of 1-octene, 1-decene, and 1-dodecene.

14. The sPAO of any of paragraphs 1 to 10, or any combination thereof, wherein the monomer is 1-decene.
15. The sPAO of any of paragraphs 1 to 10, or any combination thereof, wherein the monomer is a mixture of 1-hexene, 1-decene and 1-tetradecene.
16. A process to produce the sPAO of any of the above claims, or any combination thereof comprising contacting a feed stream comprising at least one alpha-olefin monomer having 4 to 24 carbon atoms with a catalyst system comprising a precatalyst, the precatalyst optionally having a $C_s$ symmetry and a non-coordinating anion activator, and optionally an alkyl-aluminum compound, under polymerization conditions where hydrogen, if present, is present at a partial pressure of 1379 kPa or less, based upon the total pressure of the reactor, and the alpha-olefin monomer having 4 to 24 carbon atoms is present at 10 volume % or more (based upon the total volume of the catalyst, monomers, and any diluents or solvents present) in the reactor and obtaining an sPAO.
17. The process of paragraph 16, wherein the precatalyst has a structure as described in the present application, and specifically set forth in paragraphs [00118] to [00135].
18. The process of claim 16, further comprising:
    1) optionally treating the sPAO to reduce heteroatom containing compounds to less than 600 ppm, and or
    2) optionally separating the sPAO from solvents or diluents; and or
    3) contacting the sPAO with hydrogen and a hydrogenation catalyst; and or
    4) obtaining a sPAO having a Bromine number less than 1.8.
19. The process of paragraph 16, 17, or 18, wherein the activator comprises one or more of N,N-dimethylanilinium tetra(pentafluorophenyl)borate, N,N-dialkylphenylanilinium tetra(pentafluorophenyl)borate (where the alkyl is a $C_1$ to $C_{18}$ alkyl group), trityl tetra(pentafluorophenyl)borate, tris(pentafluorophenyl)boron, tri-alkylammonium tetra(pentafluorophenyl)borate (where the alkyl is a $C_1$ to $C_{18}$ alkyl group), tetra-alkylammonium tetra(pentafluorophenyl)borate (where the alkyl is a $C_1$ to $C_{18}$ alkyl group).
20. The process of any of paragraphs 16 to 19, or any combination thereof, where an alkylaluminum compound is present and the alkylaluminum compound is represented by the formula: $R_3Al$, where each R is, independently, selected from the group consisting of methyl, ethyle, n-propyl, iso-propyl, iso-butyl, n-butyl, t-butyl, n-pentyl, iso-pentyl, neopentyl, n-hexyl, iso-hexyl, n-heptyl, iso-heptyl, n-octyl, iso-octyl, n-nonyl, n-decyl, n-undecyl, n-dodecyl, n-tridecyl, n-tetradecyl, n-pentadecy, n-hexadecyl, n-heptadecyl, n-octadecyl, and their iso-analogs.
21. The process of any one of paragraphs 16 to 20, or any combination thereof, where the process is a continuous process.
22. The process of any of paragraphs 16 to 21, or any combination thereof, where the process is a continuous process comprising:
    a) continuously introducing a feed stream comprising at least 10 mole % of the one or more $C_4$ to $C_{24}$ alpha-olefins into a reactor;
    b) continuously introducing the precatalyst and the activator into the reactor;
    c) optionally continuously introducing co-activator into the reactor; and
    d) continuously withdrawing the sPAO from the reactor.
23. The process of any of paragraphs 16 to 22, or any combination thereof, wherein the temperature in the reactor is from −10° C. to 250° C.
24. The process of any of paragraphs 16 to 23, or any combination thereof, wherein the temperature is from 30° C. to 220° C.
25. The process of any of paragraphs 16 to 24, or any combination thereof, wherein the pressure in the reactor is from 0.1 to 100 atmospheres.
26. The process of any of paragraphs 16 to 25, or any combination thereof, wherein the monomers, precatalyst, and activator are contacted for a residence time of 1 second to 100 hours.
27. The process of paragraph 16 to 26, or any combination thereof, wherein the precatalyst comprises diphenylmethylidene(cyclopentadienyl)(9-fluorenyl)zirconium dichloride.
28. The process of any of paragraphs 16 to 27, or any combination thereof, wherein solvent or diluent is present and is selected from the group consisting of butanes, pentanes, hexanes, heptanes, octanes, nonanes, decanes, undecanes, dodecanes, tridecanes, tetradecanes, pentadecanes, hexadecanes, benzene, toluene, o-xylenes, m-xylenes, p-xylenes, ethylbenzene, isopropylbenzene, and n-butylbenzene.
29. The process of any of paragraphs 16 to 28, or any combination thereof, wherein the monomers are contacted with the precatalyst compound and the activator in a reactor and the reactor is a continuous stirred tank reactor.
30. The process of any of paragraphs 16 to 29, or any combination thereof, wherein the monomers are contacted with the precatalyst compound and the activator in a reactor and the reactor is a continuous tubular reactor.
31. The process of any of paragraphs 16 to 30, or any combination thereof, wherein the monomers are contacted with the precatalyst compound and the activator in a reactor and the reactor is a batch reactor.
32. The process of any of paragraphs 16 to 31, or any combination thereof, where the monomers are contacted with the precatalyst compound and the activator in the solution phase.
33. The process of any of paragraphs 16 to 32, or any combination thereof, where the monomers are contacted with the precatalyst compound and the activator in the slurry phase.
34. The process of any of paragraphs 16 to 33, or any combination thereof, where the productivity is greater than 200 kg/g of precatalyst compound.
35. The process of any of paragraphs 16 to 34, or any combination thereof, where the productivity is greater than 10 kg/g of activator.
36. The process of any of paragraphs 16 to 35, or any combination thereof, where the catalyst system comprises a chain transfer agent.
37. The process of any one of paragraph 16 to 36, or any combination thereof, wherein the reaction temperature is from 90° C. to 120° C. and the reaction pressure is from 30 psig to 150 psig.
38. A lubricant made by the process of any one of paragraphs 16 to 37, or any combination thereof.
39. A lubricant comprising a conventional base stock and either an sPAO comprising the composition of any one of paragraphs 1 to 15, or any combination thereof or an sPAO made by the process of any one of paragraphs 16 to 37, or any combination thereof.
40. The lubricant according to paragraph 39, wherein the conventional base stock is selected from a Group I, Group II, Group III, Group IV, Group V or Fischer-Tropsch-derived lube base stock and mixtures thereof.

41. The lubricant according to paragraph 39 or 40, further comprising one or more of: thickeners, antioxidants, inhibitor packages, anti-rust additives, dispersants, detergents, friction modifiers, traction improving additives, demulsifiers, defoamants, chromophores (dyes), viscosity index improvers, pour point depressants, anti-wear additives, extreme-pressure additives, and/or haze inhibitors.

42. The lubricant according to paragraph 39, 40, or 41, where the sPAO's are present in the lubricant at from 0.01 wt % to 95 wt %, based upon the weight of the lubricant.

EXAMPLES

Experimental Section

The following examples are for purposes of illustration only and are non-limiting examples.

The 1-decene used for all of the experiments was purified by mixing 1 liter of untreated raw material with 20 grams of activated 13× molecular sieve, (which was activated by calcining at 200° C. for at least four hours under a stream of purging dry nitrogen gas), and 10 grams of Oxi-Clear catalyst (purchased from Altech Associates, Inc. of Deerfield, Ill. 60115) for at least two days inside a glove box under a dry, inert atmosphere of nitrogen. The molecular sieve and de-oxygenation catalyst were then removed by filtration in the glove box to provide purified 1-decene. Alternatively, the feeds were purified by passing through a bed of activated 13× molecular sieve alone under nitrogen atmosphere.

The polymerization/oligomerization reaction was carried out under nitrogen ($N_2$) inert atmosphere or argon inert atmosphere. All solutions were prepared using purified toluene as solvent.

In the examples, the following abbreviations are used:
Metallocene A=diphenylmethylidene(cyclopentadienyl)(9-fluorenyl)zirconium dichloride, also called diphenylmethylene(cyclopentadienyl)(9-fluorenyl)zirconium dichloride;
Activator A=N,N-dimethylanilinium tetra(perfluorophenyl)borate;
MAO=methylaluminoxane; and
TIBA=tri-isobutylaluminum.

Example 1

A solution of 100 g of purified 1-decene, 1.301 g of a TIBA stock solution (20 mg TIBA/g toluene solution) and 0.445 g of Metallocene A stock solution (1 mg Metallocene A/g toluene solution) was charged into a clean 600 ml autoclave equipped with an agitator, at room temperature. The reactor was then pressurized with 30 psig hydrogen. The mixture was then heated to 90° C. with stirring. A second solution made by adding a) 0.641 g of Activator A stock solution (1 mg Activator A/g toluene solution) and b) 20 g toluene solvent and was added and the reaction temperature was maintained at 90° C. overnight, then cooled down to room temperature, and any reactor pressure was vented. The liquid product was diluted with 50 ml heptane, stirred with 5 g activated alumina for half an hour and filtered to remove solids. The filtrate was analyzed by gas chromatography using an internal standard to obtain the wt % of normal-decane (n-$C_{10}$) formation from 1-decene hydrogenation, wt % conversion to lubes and wt % lube yield. The lube product was then isolated by flashing the light ends (solvents, unreacted $C_{10}$ fraction, and any fractions lighter than $C_{30}$) and distilled at 180° C. under high vacuum (1 millitorr) for two hours to isolate the lube product.

Examples 2-6

Examples 2-6 were conducted in a similar manner to Example 1, except that reaction temperatures, hydrogen pressures and metallocene amounts were varied to demonstrate that lubes with wide viscosity ranges were obtained using this method. Example 6 used no hydrogen in the reactor; the lube viscosity is very high and the catalyst had very low productivity as compared to Examples 1-5, when small amounts of hydrogen were present in the reactor.

The results and properties are summarized in Table 1 below.

TABLE 1

| | Example No. | | | | | |
|---|---|---|---|---|---|---|
| | 1 | 2 | 3 | 4 | 5 | 6 |
| Rxn. Temp. (° C.) | 90 | 110 | 110 | 130 | 120 | 110 |
| $H_2$ press. (psig) | 30 | 30 | 100 | 100 | 150 | 0 |
| $H_2$/1-$C_{10}$ (mole ratio) | 0.056 | 0.053 | 0.177 | 0.168 | 0.259 | 0.000 |
| μg Metallocene/g 1-$C_{10}$ | 4.45 | 2.23 | 2.23 | 2.23 | 4.45 | 4.45 |
| Wt % conversion | 85 | 84 | 83 | 56 | 67 | 61 |
| Wt % product selectivity | | | | | | |
| $C_{20}$ | 0 | 0.2 | 0.4 | 0.4 | 0.7 | 0.8 |
| Lube | 100 | 99.8 | 99.6 | 99.6 | 99.3 | 99.2 |
| Wt % lube yield | 85.4 | 83.5 | 82.2 | 55.4 | 66.6 | 59.5 |
| Lube Properties | | | | | | |
| Kv100 (cSt) | 730.7 | 513.4 | 276.6 | 214.6 | 176.1 | 1719.9 |
| Kv40 (cSt) | 8469.7 | 5746.8 | 2923.7 | 2197.0 | 1764.4 | 20643.6 |
| VI | 283 | 265 | 234 | 233 | 215 | 332 |
| Bromine No. | 0.2 | 0.9 | 0.8 | 1 | 1.4 | 1 |
| Pour Point (° C.) | −26 | −34 | −39 | nm | nm | nm |
| Mn | 11,708 | 9,841 | 6,797 | 5,912 | 5,305 | 16,862 |
| Mw/Mn | 1.93 | 1.80 | 1.77 | 1.73 | 1.76 | 2.14 |
| Kg lube/g metallocene | 192.0 | 375.5 | 369.3 | 249.1 | 149.6 | 13.4 |
| Kg lube/g activator | 133.3 | 260.7 | 256.4 | 172.9 | 103.9 | 9.3 |
| Wt % 1-$C_{10}$ hydrogenated | 0.2 | 0.0 | 1.7 | 0.0 | 3.8 | 2.7 | nm = not measured

The results set forth in Table 1 indicate several advantages of the improved process, e.g., high olefin conversion and lube yields, up to 85% for both. Additionally, high catalyst productivity is demonstrated by the ratio of kilograms of lube produced per gram of metallocene, or per gram of activator.

A wide range of viscosities ($Kv_{100}$), from 176 cSt to 730 cSt was achieved by adjusting reaction temperatures and hydrogen pressures. The lube products had Bromine numbers less than 2 directly from polymerization, without a separate hydrogenation step.

The calculated amount of 1-decene hydrogenation is very low in the presence of up to 150 psig hydrogen pressure, ranging from 0 to 3.8%. This is especially unexpected when one considers that the Bromine number of the lube product is very low. These results showed the unexpected selective hydrogenation of polymer product, without corresponding hydrogenation of the feed olefins.

The improved process is desirable in that it is more simpler to produce lubes of low Bromine number with high lube yields and high catalyst productivity.

The lube products had very narrow molecular weight distributions (Mw/Mn), as indicated by an Mw/Mn of less than 2, indicating that the presence of hydrogen did not negatively impact the Mw/Mn. Narrow Mw/Mn is critical for good shear stability of a lubricant basestock.

Comparative Examples A and B

Comparative Examples A and B were run using catalyst systems (with methylaluminoxane activators) described in U.S. Pat. No. 6,858,767 B1. In Comparative Example A, 100 g of purified 1-decene was charged into a 600 ml autoclave. The reactor was pressurized with 30 psig hydrogen and then heated to 110° C. with stirring. Then a catalyst solution containing 20 g of toluene solvent, 1.414 g MAO activator solution (10 wt % MAO/toluene) and 0.2225 g Metallocene A stock solution (1 mg Metallocene A/g toluene solution) was added to the autoclave under pressure. The autoclave temperature was maintained at 110° C. After stirring overnight, the reactor was cooled down and vented to atmospheric pressure. Then 5 g of activated alumina was charged to the reaction product and stirred for half an hour. The solids were removed by filtration and the product was analyzed and isolated similarly to Example 1. Comparative Example B was run in a similar manner to Comparative Example A, except that hydrogen pressure was raised to 100 psig. The results and product properties are summarized in Table 2 below.

TABLE 2

| Comp. Ex. | A | B |
|---|---|---|
| Rxn. Temp. (° C.) | 110 | 110 |
| H$_2$ press. (psig) | 30 | 100 |
| H$_2$/1-C$_{10}$ (mole ratio) | 0.053 | 0.177 |
| μg Metallocene/g 1-C$_{10}$ | 2.23 | 2.23 |
| Wt % conversion | 41.7 | 45.6 |
| Wt % product selectivity | | |
| C$_{20}$ | 10.6 | 14.9 |
| Lube | 89.4 | 85.1 |
| Wt % lube yield | — | — |
| Lube Properties | | |
| Kv$_{100}$ (cSt) | 374.9 | 285.4 |
| Kv$_{40}$ (cSt) | 3714.3 | 2707.1 |
| VI | 260 | 249 |
| Bromine No. | 3.8 | 3.4 |
| Pour Point (° C.) | −27 | −32 |
| Mn g/mol | 7,563 | 6,953 |

TABLE 2-continued

| Comp. Ex. | A | B |
|---|---|---|
| Mw/Mn | 2.51 | 2.33 |
| Kg lube/g Metallocene | 167.6 | 174.3 |
| Kg lube/g MAO | 2.6 | 2.7 |
| Wt % 1-C$_{10}$ hydrogenated | 4.9 | 17.6 |

The as-polymerized lubes of the Comparative Examples have Bromine numbers of 3.8 and 3.4 respectively, well above the Bromine number of 2 which is required for use in lube basestocks. A separate hydrogenation step would be necessary to reduce the Bromine numbers of the Comparative Examples to acceptable levels, which adds complexity and expense to the overall process.

The lube conversions of Comparative Examples A and B were below 50%, in contrast to Examples 1-5 of the improved process, which were all above 50%. Likewise, catalyst productivities, as measured by kilograms lube produced per gram metallocene or gram of MAO activator, were generally lower for the Comparative Examples.

Example 2 and Comparative Example A were run at the same temperatures and hydrogen pressures. Likewise, Example 3 and Comparative Example B were run at the same temperatures and hydrogen pressures. In both instances the amount of undesirable 1-decene hydrogenation during the polymerization process was significantly less according to the improved process of the present disclosure.

The lube products produced by the Comparative Examples had an Mw/Mn of greater than 2; in contrast, the products of the presently improved process, using the NCA activator had an Mw/Mn of less than 2.0. As stated above, narrower molecular weight distribution generally translates to much improved shear stability when used as a lubricant basestock or as a blend stock.

Examples 7-10

In Examples 7-10, other α-olefins were tested to determine whether they could be used as feed to produce high quality basestocks with high VI and low pour points. The polymerization process and analysis of product produced were conducted in a manner similar to that in Example 1. Results are set forth in Table 3 below.

TABLE 3

| Example No. | 7 | 8 | 9 | 10 |
|---|---|---|---|---|
| Feed | 1-hexene | 1-octene | 1-dodecene | 1-C$_6$, 1-C$_{10}$, 1-C$_{14}$ |
| Rxn. Temp. (° C.) | 110 | 110 | 110 | 110 |
| H$_2$ press. (psig) | 100 | 100 | 100 | 100 |
| H$_2$/1-C$_{10}$ (mol) | 0.177 | 0.177 | 0.177 | 0.177 |
| μg Metallocene/g 1-C$_{10}$ | 4.45 | 4.45 | 4.45 | 4.45 |
| Wt % conversion | 85 | 93.8 | 88.5 | 93.7 |
| Wt % lube yield | 85.4 | 92.8 | 88.0 | 93.0 |
| Lube Properties | | | | |
| Kv$_{100}$ (cSt) | 533.8 | 364.0 | 198.7 | 231.8 |
| Kv$_{40}$ (cSt) | 14401.2 | 4685.6 | 1916.0 | 2665.8 |
| VI | 180 | 228 | 226 | 214 |
| Bromine No. | 1.6 | 1 | 0.3 | 1.3 |
| Pour Point (° C.) | −12 | −26 | — | — |
| Mn | 4050 | 5454 | 6228 | 5329 |
| Mw/Mn | 2.02 | 1.98 | 1.89 | 2.07 |
| Kg lube/g Metallocene | 192.0 | 208.4 | 197.7 | 208.9 |
| Kg lube/g Activator | 133.3 | 144.7 | 137.3 | 145.0 |

Even with alternative α-olefin feedstocks, the improved process of the present disclosure results in high lube productivity per gram of metallocene or activator, high conversion rates and high lube yields. The lube product from the polymerization reaction all have Bromine numbers below 2.0 and narrow molecular weight distribution, close to or less than 2.0.

Comparative Example C

In this set of examples, run similarly to Comparative Example B, during the polymerization reaction samples were taken at different reaction time intervals as shown in Table 4 and analyzed by gas chromatography to quantify the amount of 1-decene hydrogenation as compared to the amount of polymerization reaction. The polymerization conditions were run similarly to those in U.S. Pat. No. 6,858,767. The results are summarized in Table 4 below. Reaction conditions were: 110° C., 100 prig $H_2$, 0.2223 mg metallocene/g 1-decene, MAO activator, MAO to metallocene molar ratio 500/1.

TABLE 4

| Comp. Ex. | C-1 | C-2 | C-3 | C-4 |
|---|---|---|---|---|
| Rxn time (hr) | 1 | 3 | 6 | 16 |
| Wt % Conversion | 40.5 | 53.4 | 59.7 | 50.4 |
| Wt % product distribution | | | | |
| 1-decene | 48.7 | 30.4 | 23.4 | 31.6 |
| Other $C_{10}$ isomers | 4.1 | 4.0 | 4.0 | 4.3 |
| n-decane (n-$C_{10}$) | 6.7 | 12.2 | 12.9 | 13.8 |
| $C_{20}$ | 0.8 | 3.1 | 3.0 | 5.9 |
| Lube | 39.7 | 50.3 | 56.7 | 44.5 |
| Lube/n-$C_{10}$ ratio | 5.9 | 4.1 | 4.4 | 3.2 |

Other C10 isomers include internal decenes and branched decene and decanes.

Example 11

Conditions similar to Example 3 were used, except that reaction samples were taken at different reaction times as shown in Table 5 for analysis by gas chromatography to quantify the amount of 1-decene hydrogenation as compared to the amount of polymerization reaction. Results are summarized in Table 5 below.

TABLE 5

| Example | 11-1 | 11-2 | 11-3 | 11-4 |
|---|---|---|---|---|
| Rxn time (hr) | 1 | 3 | 6 | 16 |
| Wt % Conversion | 82 | 92.0 | 93.9 | 97.3 |

TABLE 5-continued

| Example | 11-1 | 11-2 | 11-3 | 11-4 |
|---|---|---|---|---|
| Wt % product distribution | | | | |
| 1-decene | 11.6 | 2.2 | 1.2 | 0.3 |
| Other $C_{10}$ isomers | 4.9 | 4.1 | 4.0 | 3.0 |
| n-decane (n-$C_{10}$) | 1.1 | 1.7 | 1.0 | 0.1 |
| $C_{20}$ | 0.1 | 0.8 | 0.9 | 3.7 |
| Lube | 82.2 | 91.2 | 93.0 | 93.6 |
| Lube/n-$C_{10}$ ratio | 76.4 | 52.4 | 96.2 | 936.2 |

Comparing the data in Tables 4 and 5, it is clearly demonstrated that Example 11, according to the present disclosure, had higher 1-decene conversion to lube, very high lube yields, very low amount of hydrogenation of 1-decene to n-decane and low levels of dimer ($C_{20}$) formation, which is undesirable as lube basestock, throughout the reaction time period.

Examples 12-16, Comparative Ex. D and Comparative Ex. E (Blends)

Blends were prepared using the poly-1-decene produced, as follows.

For Example 12, a HVI-sPAO was prepared similar to Example 1, except that the reaction temperature was 130° C. and the hydrogen pressure was 100 psig.

For Example 13, a HVI-sPAO was prepared similar to Example 1, except that the reaction temperature was 110° C. and the hydrogen pressure was 100 psig.

For Example 14, a HVI-sPAO was prepared similar to Example 1, except that the reaction temperature was 110° C. and the hydrogen pressure was 30 psig.

For Examples 15 and 16, the HVI-sPAO of Example 6 was used.

For Comparative Example D, a PAO was prepared similar to Example 1, except that the metallocene was dimethylsilyl-bis(indenyl)zirconium dichloride, the reaction temperature was 55° C. and no hydrogen was added. Preparation of this example can be found in WO 2007011459 A 1.

For Comparative Example E, a HVI-sPAO was prepared similar to Example 1, except that the metallocene was dimethylsilylbis(tetrahydro-indenyl)zirconium dichloride, the reaction temperature was 70° C. and no hydrogen was added. Preparation of this example can be found in WO 2007011459 A1. The PAO formed had a high degree of isotacticity as determined by NMR spectra.

In these blend experiments, the low viscosity ester fluid used is prepared from the typical ester synthesis reaction from a simple acid and alcohol. It has the viscometric properties as following: 100° C. Kv=1.3 cSt and 40° C. Kv=3.19 cSt. The low viscosity PAO used in the blends is available from ExxonMobil Chemical Co. It has the following properties: 100° C. Kv=1.71 cSt and 40° C. Kv=5.14 cSt. The blending results are set forth in Table 6 below.

TABLE 6

| | Example No. | | | | | | |
|---|---|---|---|---|---|---|---|
| | 12 | 13 | 14 | 15 | 16 | Comp. D | Comp. E |
| HVI-sPAO Properties | | | | | | | |
| $Kv_{100}$ (cSt) | 152.2 | 282.7 | 1096.0 | 1719.9 | 1719.9 | 679.4 | 155.4 |
| $Kv_{40}$ (cSt) | 1479.3 | 2873.8 | 12643.6 | 20643.6 | 20643.6 | 7318.6 | 1440.5 |
| VI | 210 | 233 | 308 | 332 | 332 | 287 | 217 |
| Blend composition | | | | | | | |
| Wt % HVI-PAO | 42.8 | 37.5 | 29.6 | 27.6 | 20 | 33 | 44 |
| Wt % low vis ester | 20 | 20 | 20 | 20 | 20 | 47 | 25.9 |
| Wt % low vis PAO | 37.2 | 42.5 | 50.4 | 52.4 | 60 | 20 | 20 |

TABLE 6-continued

| | Example No. | | | | | | |
|---|---|---|---|---|---|---|---|
| | 12 | 13 | 14 | 15 | 16 | Comp. D | Comp. E |
| Blend Properties | | | | | | | |
| Kv$_{100}$ (cSt) | 9.0 | 9.7 | 14.4 | 16.5 | 9.6 | 12.2 | 11.6 |
| Kv$_{40}$ (cSt) | 37.0 | 38.6 | 54.8 | 62.7 | 33.7 | 48.7 | 52.3 |
| VI | 237 | 251 | 276 | 280 | 291 | 246 | 224 |
| Pour point (° C.) | <−61.1 | <−60.9 | <−60.9 | <−60.9 | <−60.9 | −36 | <−60 |
| Brookfield Vis @ −40° C. (cP) | 3389 | 3189 | 3989 | 4219 | 1889 | >400,000 | >400,000 |
| Brookfield Vis @ −55° C. (cP) | 22995 | 20046 | 23545 | 24945 | 10598 | N.M.* | >999,999 |

*not measurable

As demonstrated in Table 6, the samples prepared using the HVI-sPAO of the present disclosure all had much lower Brookfield viscosities as compared to the Comparative Examples, which is advantageous in lubricant applications.

Certain samples produced above were analyzed by $^1$H and $^{13}$C NMR to determine the unique chemical compositions made by syndiotactic polymer-forming metallocene and non-coordinating anion activators. The $^{13}$C NMR characterization of tacticity and the $^1$H NMR analysis of olefin termination structures are summarized in Tables A and B below.

These data show that novel lube fluids made in Examples 1 to 11 have a low mr/rr ratio of 3.2 to 6.1. The lube fluids made in comparative Examples A to C (according to the method as described in U.S. Pat. No. 6,858,761), have a higher mr/rr ratio (typically greater than 10). The lower mr/rr ratio of the novel materials of this disclosure indicates a higher content of the preferentially desired syndiotactic rr triad. Without wising to be bound by theory, it is believed that the higher syndiotactic content may increase the entanglement length of the polymer, improving the low-temperature viscometric behavior, blending capability and lubricating film performance. FIG. 1 compares the pour points of inventive 1-decene-based lube fluids made in examples 1-3. As FIG. 1 shows, Examples 1, 2, and 3 have lower pour points than comparative Examples A and B. At any given viscosity, our inventive products have lower pour points than prior art examples and lube products made with methyl alumoxane as activator.

The data in Tables A and B also show that Examples 1 to 11 have lower ratios of vinylidene/1,2-disubstituted olefins, ranging from 0.6 to 3.4. In comparison, Comparative Example A to C fluids have high ratios of vinylidene/1,2-disubstituted olefins, ranging from 9.1 to 14.2. Vinylidene and 1,2-disubstituted olefins are the major olefinic components in lube fluids. Fluids with high vinylidene contents usually have poorer oxidative stability, due to the higher reactivity of the vinylidene olefins with peroxides or radicals, in comparison with 1,2-disubstituted olefins. Therefore, the lower ratio of vinylidene/di-substituted suggests better oxidative stability.

In summary, the fluids made in our inventive examples have different chemical compositions from prior art compositions. The inventive compositions have atactic contents—as defined by mr/rr ratios—of less than 10, preferably less than 7, most preferably between 3 to 7. The inventive compositions have olefin compositions—as defined by the ratios of vinylidene/1,2-disubstituted olefins—of less than 9, preferably less than 7, more preferably less than 5, most preferably less than 4.

TABLE A

NMR data of inventive Examples 1 to 11

| | Example No. | | | | | | | | | | |
|---|---|---|---|---|---|---|---|---|---|---|---|
| | 1 | 2 | 3 | 4 | 5 | 6 | 7 | 8 | 9 | 10 | 11 |
| Feed Olefins | 1-C$_{10}$ | 1-C$_{10}$ | 1-C$_{10}$ | 1-C$_{10}$ | 1-C$_{10}$ | 1-C$_{10}$ | 1-C$_6$ | 1-C$_8$ | 1-C$_{12}$ | 1-C$_{6,10,14}$ | 1-C$_{10}$ |
| KV100° C., cSt | 730.7 | 513.4 | 276.6 | 214.6 | 176.1 | 1719.9 | 533.8 | 364.0 | 198.7 | 231.8 | 282.82 |
| Triad content by $^{13}$C NMR | | | | | | | | | | | |
| mm | 0.25 | 0.29 | 0.31 | 0.31 | 0.32 | 0.23 | 0.62 | 0.34 | 0.33 | na | 0.33 |
| mr | 0.64 | 0.59 | 0.56 | 0.56 | 0.56 | 0.64 | 0.33 | 0.52 | 0.51 | | 0.56 |
| rr | 0.11 | 0.13 | 0.13 | 0.13 | 0.12 | 0.13 | 0.05 | 0.13 | 0.16 | | 0.11 |
| ratio of mr/rr | 6.1 | 4.6 | 4.3 | 4.4 | 4.6 | 5.1 | 5.9 | 4.0 | 3.2 | | 5.0 |
| $^1$H Olefin Type by NMR | | | | | | | | | | | |
| vinyl olefin | 5.2 | 10.0 | 12.0 | 15.6 | 14.3 | 8.0 | 6.0 | 4.7 | 2.5 | 5.7 | 6.9 |
| 1,2-disubstituted olefin | 57.4 | 47.5 | 24.7 | 22.4 | 17.2 | 45.0 | 14.1 | 20.9 | 23.0 | 22.0 | 24.1 |
| trisubstituted olefin | .9 | 7.9 | 12.0 | 11.4 | 10.8 | 24.0 | 22.5 | 15.3 | 24.1 | 17.4 | 17.9 |
| vinylidene olefin | 36.5 | 34.6 | 51.3 | 50.5 | 57.7 | 23.0 | 57.3 | 59.1 | 50.4 | 54.9 | 51.1 |
| ratio of vinylidene/disub. | 0.64 | 0.73 | 2.08 | 2.26 | 3.35 | 0.51 | 4.05 | 2.83 | 2.19 | 2.50 | 2.12 |

TABLE B

NMR data of comparative Examples

| Comparative Example | A | B | C |
|---|---|---|---|
| Feedstock | 1-$C_{10}$ | 1-$C_{10}$ | 1-$C_{10}$ |
| KV100° C., cSt | 374.9 | 285.4 | 256.74 |
| Triad content by $^{13}$C NMR | | | |
| mm | 0.22 | 0.21 | 0.25 |
| mr | 0.71 | 0.72 | 0.69 |
| rr | 0.06 | 0.07 | 0.07 |
| ratio of mr/rr | 11.3 | 10.8 | 10.4 |
| vinyl olefin | .6 | 2.1 | 1.1 |
| 1,2-disubstituted olefin | 8.3 | 5.8 | 5.4 |
| trisubstituted olefin | 15.3 | 12.7 | 17.5 |
| vinylidene olefin | 75.8 | 79.5 | 76.0 |
| ratio of vinylidene/ disubstituted olefins | 9.1 | 13.7 | 14.2 |

Shear Stability Test results of Example 3 sample: The pure Example 3 sample was sent to South West Research Institute for a Tapered Roller Bearing Test (CEC L-45-T-93). The test was conducted at 60° C., 1475 rpm, 5000 N load for 20 hours. After the test, the oil showed only 1.6% 100° C. Kv loss. This is excellent shear stability. In similar test, the samples made in the Comparative Examples A to C will have a much higher amount of viscosity loss. Our inventive Examples all have very low molecular weight distribution values which leads to very shear stable products in comparison to the high molecular weight distribution of the Comparative Examples which leads to poor shear stability. These results demonstrated that the samples made in this disclosure have outstanding shear stability, which is important for many high performance lubricant applications.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. Likewise, the term "comprising" is considered synonymous with the term "including" for purposes of Australian law.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains. The invention has been described above with reference to numerous embodiments and specific examples. Many variations will suggest themselves to those skilled in this art in light of the above detailed description. All such obvious variations are within the full intended scope of the appended claims.

What is claimed is:

1. A liquid polyalphaolefin, PAO, comprising one or more $C_4$ to $C_{24}$ monomers, said PAO having:
    a) a mm triad content of at least 23%, as measured by $^{13}$C NMR;
    b) a mr triad content of 25 to 60%, as measured by $^{13}$C NMR, where the mr to mm triad ratio is at least 1.0;
    c) a pour point of Z ° C. or less, where Z=0.0648X-51.2, where X=kinematic viscosity at 100° C. as reported in centistokes (cSt);
    d) a kinematic viscosity at 100° C. of 100 cSt or more;
    e) a ratio of mr triads to rr triads, as determined by $^1$H NMR, of less than 9;
    f) a ratio of vinylidene to 1,2-disubstituted olefins, as determined by $^1$H NMR, of less than 8;
    g) a viscosity index of 120 or more; and
    h) a Mn of 40,000 or less.

2. The PAO of claim 1, wherein the kinematic viscosity at 100° C. is 200 cSt or more.

3. The PAO of claim 1, wherein the PAO has an Mw/Mn of 2.0 or less.

4. The PAO of claim 1, wherein the PAO has 40 to 60 mole % of rr triads as determined by $^{13}$C NMR.

5. The PAO of claim 1, wherein the PAO has an as-polymerized Bromine number of less than 2.

6. The PAO of claim 1, wherein the monomers are alpha olefins selected from the group consisting of hexene, heptene, octene, nonene, decene, dodecene, 3-methyl-1-butene, and tetradecene.

7. The PAO of claim 1, wherein the mr to mm triad ratio is 1.1 to 7.0.

8. The PAO of claim 1, wherein the mm triad content is 23 to 34%, as measured by $^{13}$C NMR.

* * * * *